(12) United States Patent
Makinoshima et al.

(10) Patent No.: US 12,134,596 B2
(45) Date of Patent: Nov. 5, 2024

(54) COMPOUND, RESIN, COMPOSITION, RESIST PATTERN FORMATION METHOD, CIRCUIT PATTERN FORMATION METHOD AND METHOD FOR PURIFYING RESIN

(71) Applicant: Mitsubishi Gas Chemical Company, Inc., Tokyo (JP)

(72) Inventors: Takashi Makinoshima, Hiratsuka (JP); Junya Horiuchi, Hiratsuka (JP); Masatoshi Echigo, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 900 days.

(21) Appl. No.: 16/966,415

(22) PCT Filed: Jan. 31, 2019

(86) PCT No.: PCT/JP2019/003400
§ 371 (c)(1),
(2) Date: Jul. 30, 2020

(87) PCT Pub. No.: WO2019/151400
PCT Pub. Date: Aug. 8, 2019

(65) Prior Publication Data
US 2020/0361843 A1 Nov. 19, 2020

(30) Foreign Application Priority Data
Jan. 31, 2018 (JP) ................................ 2018-015520

(51) Int. Cl.
| | | |
|---|---|---|
| C07C 43/295 | (2006.01) | |
| C07C 317/22 | (2006.01) | |
| C07C 321/30 | (2006.01) | |
| C08G 65/38 | (2006.01) | |
| G03F 7/022 | (2006.01) | |
| G03F 7/11 | (2006.01) | |
| G03F 7/20 | (2006.01) | |
| G03F 7/40 | (2006.01) | |

(52) U.S. Cl.
CPC .......... *C07C 43/295* (2013.01); *C07C 317/22* (2013.01); *C07C 321/30* (2013.01); *C08G 65/38* (2013.01); *G03F 7/022* (2013.01); *G03F 7/11* (2013.01); *G03F 7/20* (2013.01); *G03F 7/40* (2013.01)

(58) Field of Classification Search
CPC ... C07C 43/295; C07C 317/22; C07C 321/30; C08G 65/38; C08G 8/04; C08G 4/00; G03F 7/022; G03F 7/11; G03F 7/20; G03F 7/40; G03F 7/0397; G03F 7/0226; G03F 7/094; C09D 161/12; H01L 21/0274; H01L 21/027
See application file for complete search history.

(56) References Cited

U.S. PATENT DOCUMENTS

| | | | |
|---|---|---|---|
| 3,281,465 A | 10/1966 | Stecker | |
| 4,319,052 A | 3/1982 | Styskin et al. | |
| 2005/0255712 A1 | 11/2005 | Kato et al. | |
| 2006/0234158 A1* | 10/2006 | Hatakeyama | G03F 7/094 430/313 |
| 2008/0153031 A1 | 6/2008 | Echigo et al. | |
| 2012/0065291 A1* | 3/2012 | Matsumura | G03F 7/0397 526/248 |
| 2014/0248561 A1 | 9/2014 | Echigo et al. | |
| 2015/0090691 A1 | 4/2015 | Echigo et al. | |
| 2016/0068709 A1* | 3/2016 | Endo | G03F 7/091 524/597 |

(Continued)

FOREIGN PATENT DOCUMENTS

| | | |
|---|---|---|
| CN | 105209974 A | 12/2015 |
| CN | 107250089 A | 10/2017 |

(Continued)

OTHER PUBLICATIONS

International Search Report for PCT/JP2019/003400, mailed Apr. 23, 2019, and English Translation submitted herewith (5 pages).
Nakayama, T. et al., "A New Three-Component Photoresist Based on Calix[4]resorcinarene Derivative, a Cross-linker, and a Photo-acid Generator," Bulletin of the Chemical Society of Japan, 1998, vol. 71, No. 12, pp. 2979-2984.
Okazaki, S. et al., "New Trends of Photoresists," CMC Publishing Co., Ltd., Sep. 2009, pp. 211-259. (Cited in Specification).

(Continued)

*Primary Examiner* — Sean M DeGuire
*Assistant Examiner* — Alexander N. Lee
(74) *Attorney, Agent, or Firm* — Fitch, Even, Tabin & Fla

(57) ABSTRACT

A compound represented by the following formula (1).

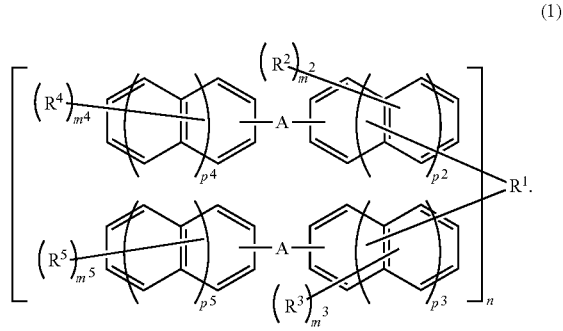

The compound can be used as a film forming material for lithography or an optical component forming material. A resin may also be obtained using this compound as a monomer, a composition, a method for forming a resist pattern, a method for forming an insulating film, a method for forming a circuit pattern, and a method for purifying the above compound or resin.

20 Claims, No Drawings

(56) References Cited

U.S. PATENT DOCUMENTS

| | | | |
|---|---|---|---|
| 2017/0001972 A1 | 1/2017 | Echigo et al. | |
| 2017/0073288 A1 | 3/2017 | Makinoshima et al. | |
| 2017/0075220 A1 | 3/2017 | Sato et al. | |
| 2017/0334837 A1 | 11/2017 | Komori et al. | |
| 2018/0029968 A1 | 2/2018 | Toida et al. | |
| 2021/0047457 A1* | 2/2021 | Echigo | C08G 10/04 |

FOREIGN PATENT DOCUMENTS

| | | | |
|---|---|---|---|
| CN | 107428935 A | 12/2017 | |
| JP | H04-344286 A | 11/1992 | |
| JP | H08-087110 A | 4/1996 | |
| JP | H08-127552 A | 5/1996 | |
| JP | 08328243 A * | 12/1996 | |
| JP | H08-328243 A | 12/1996 | |
| JP | H09-2987 A | 1/1997 | |
| JP | H09-218511 A | 8/1997 | |
| JP | H11-029621 A | 2/1999 | |
| JP | 2002-334869 A | 11/2002 | |
| JP | 2004-177668 A | 6/2004 | |
| JP | 2004-271838 A | 9/2004 | |
| JP | 2005-134434 A | 5/2005 | |
| JP | 2005-250434 A | 9/2005 | |
| JP | 2005-326838 A | 11/2005 | |
| JP | 2007-226170 A | 9/2007 | |
| JP | 2007-226204 A | 9/2007 | |
| JP | 2008-145539 A | 6/2008 | |
| JP | 2009062398 A * | 3/2009 | |
| JP | 2009-173623 A | 8/2009 | |
| JP | 2009-538943 A | 11/2009 | |
| JP | 2010-138393 A | 6/2010 | |
| JP | 2014-237602 A | 12/2014 | |
| JP | WO2015/137485 A1 | 9/2015 | |
| JP | 2015-174877 A | 10/2015 | |
| JP | 2016-199472 A | 12/2016 | |
| JP | WO2015/137486 A1 | 4/2017 | |
| WO | 1999/029706 A2 | 6/1999 | |
| WO | 2004/066377 A1 | 8/2004 | |
| WO | 2007/140941 A2 | 12/2007 | |
| WO | 2013/024778 A1 | 2/2013 | |
| WO | 2013/024779 A1 | 2/2013 | |
| WO | 2014/185335 A1 | 11/2014 | |
| WO | 2015/080240 A1 | 6/2015 | |
| WO | WO-2016158674 A1 * | 10/2016 | C07C 233/80 |
| WO | 2017/188297 A1 | 11/2017 | |
| WO | 2018/016614 A1 | 1/2018 | |
| WO | 2018/016634 A1 | 1/2018 | |
| WO | 2018/016640 A1 | 1/2018 | |
| WO | 2018/052026 A1 | 3/2018 | |
| WO | 2018/052028 A1 | 3/2018 | |
| WO | 2018/101377 A1 | 6/2018 | |

OTHER PUBLICATIONS

Sone, T. et al., "Synthesis and Properties of Sulfur-Bridged Analogs of p-tert-Butylcalix[4]arene," Tetrahedron, 1997, vol. 53, No. 31, pp. 10689-10698.

Sato et al., "Anion Binding Properties of Tris (2-hydroxyphenyl) Methanes," Journal of Inclusion Phenomena and Macrocyclic Chemistry (2013), vol. 77, pp. 385-394.

Biali, S.E. et al., "Conformation, Inversion Barrier, and Solvent-Induced Conformational Shift in Exo- and Endo/Exo-Calix[4]arenes," Journal of Organic Chemistry (1997), vol. 62, No. 24, pp. 8350-8360.

Bohmer, V. et al., "Annelated Calixarenes Composed of Calix[4]arenes with Hydroxy Groups in the Endo and Exo Position," Journal of Organic Chemistry (1996).

STN Search Records, Registry Nos. 105094-48-2 and 105094-45-9, 1986 (2 pages).

Bohmer, V. et al., "Die Synthese reiner Oligo[(hydroxy-5-nitro-1,3-phenylen)methylen]e Verbindungen mit mehreren ortho-bzw. para-Nitrophenol-bausteinen im Molekül," Die Makromolekulare Chemie, 1976, vol. 177, pp. 1745-1770.

International Search Report for PCT/JP2020/003740, mailed Apr. 28, 2020, and English Translation submitted herewith (7 pages).

* cited by examiner

COMPOUND, RESIN, COMPOSITION, RESIST PATTERN FORMATION METHOD, CIRCUIT PATTERN FORMATION METHOD AND METHOD FOR PURIFYING RESIN

CROSS-REFERENCE TO RELATED APPLICATIONS

This application is a U.S. national phase application filed under 35 U.S.C. § 371 of International Application Number PCT/JP2019/003400, filed Jan. 31, 2019, designating the United States, which claims priority from Japanese Application Number 2018-015520, filed Jan. 31, 2018.

Field of the Invention

The present invention relates to a compound, a resin, a composition, a resist pattern formation method, a circuit pattern formation method, and a method for purifying the resin.

Background of the Invention

In the production of semiconductor devices, fine processing is practiced by lithography using photoresist materials. In recent years, further miniaturization based on pattern rules has been demanded along with increase in the integration and speed of LSI (large scale integrated circuits). The light source for lithography used upon forming resist patterns has been shifted to ArF excimer laser (193 nm) having a shorter wavelength from KrF excimer laser (248 nm). The introduction of extreme ultraviolet (EUV, 13.5 nm) is also expected.

However, because conventional polymer-based resist materials have a molecular weight as large as about 10,000 to 100,000 and also wide molecular weight distribution, in lithography using such a polymer-based resist material, roughness occurs on a pattern surface; the pattern dimension becomes difficult to be controlled; and there is a limitation in miniaturization. Accordingly, various low molecular weight resist materials have been proposed so far in order to provide resist patterns having higher resolution. The low molecular weight resist materials are expected to provide resist patterns having high resolution and small roughness, because of their small molecular sizes.

Various materials are currently known as such low molecular weight resist materials. For example, an alkaline development type negative type radiation-sensitive composition (see, for example, Patent Literature 1 and Patent Literature 2) using a low molecular weight polynuclear polyphenolic compound as a main component has been suggested; and as a candidate of a low molecular weight resist material having high heat resistance, an alkaline development type negative type radiation-sensitive composition (see, for example, Patent Literature 3 and Non Patent Literature 1) using a low molecular weight cyclic polyphenolic compound as a main component has been suggested as well. Also, as a base compound of a resist material, a polyphenol compound is known to be capable of imparting high heat resistance despite a low molecular weight and useful for improving the resolution and roughness of a resist pattern (see, for example, Non Patent Literature 2).

In addition, the present inventors have proposed a resist composition containing a compound having a specific structure and an organic solvent (see Patent Literature 4) as a material that is excellent in etching resistance and is also soluble in a solvent and applicable to a wet process.

Also, as the miniaturization of resist patterns proceeds, the problem of resolution or the problem of collapse of resist patterns after development arises. Therefore, resists have been desired to have a thinner film. However, if resists merely have a thinner film, it is difficult to obtain the film thicknesses of resist patterns sufficient for substrate processing. Therefore, there has been a need for a process of preparing a resist underlayer film between a resist and a semiconductor substrate to be processed, and imparting functions as a mask for substrate processing to this resist underlayer film in addition to a resist pattern.

Various resist underlayer films for such a process are currently known. For example, as a material for realizing resist underlayer films for lithography having the selectivity of a dry etching rate close to that of resists, unlike conventional resist underlayer films having a fast etching rate, an underlayer film forming material for a multilayer resist process containing a resin component having at least a substituent that generates a sulfonic acid residue by eliminating a terminal group under application of predetermined energy, and a solvent has been suggested (see Patent Literature 5). Also, in order to realize a resist underlayer film for lithography having the selectivity of a dry etching rate smaller than that of resists, a resist underlayer film material comprising a polymer having a specific repeat unit has been suggested (see Patent Literature 6). Furthermore, in order to realize a resist underlayer film for lithography having the selectivity of a dry etching rate smaller than that of semiconductor substrates, a resist underlayer film material comprising a polymer prepared by copolymerizing a repeat unit of an acenaphthylene and a repeat unit having a substituted or unsubstituted hydroxy group has been suggested (see Patent Literature 7).

Meanwhile, as materials having high etching resistance for this kind of resist underlayer film, amorphous carbon underlayer films formed by chemical vapour deposition (CVD) using methane gas, ethane gas, acetylene gas, or the like as a raw material are well known. However, resist underlayer film materials that can form resist underlayer films by a wet process such as spin coating or screen printing have been demanded from the viewpoint of a process.

The present inventors have also proposed an underlayer film forming composition for lithography containing a compound having a specific structure and an organic solvent (see Patent Literature 8) as a material that is excellent in etching resistance, has high heat resistance, and is soluble in a solvent and applicable to a wet process.

As for methods for forming an intermediate layer used in the formation of a resist underlayer film in a three-layer process, for example, a method for forming a silicon nitride film (see Patent Literature 9) and a CVD formation method for a silicon nitride film (see Patent Literature 10) are known. Also, as intermediate layer materials for a three-layer process, materials comprising a silsesquioxane-based silicon compound are known (see Patent Literature 11 and Patent Literature 12).

Various compositions have been further proposed as optical component forming compositions. For example, Patent Literature 13 discloses an energy beam curable resin composition for optical lens sheets comprising: an ionic liquid; a compound having a predetermined polyalkylene oxide structure and a (meth)acryloyl group; a predetermined (meth)acrylate monomer; and a photopolymerization initiator. Patent Literature 14 describes that a resin composition containing: a copolymer having a specific structural unit; a specific curing catalyst; and a solvent is suitably used for microlenses or for flattening films.

CITATION LIST

Patent Literature

Patent Literature 1: Japanese Patent Laid-Open No. 2005-326838
Patent Literature 2: Japanese Patent Laid-Open No. 2008-145539
Patent Literature 3: Japanese Patent Laid-Open No. 2009-173623
Patent Literature 4: International Publication No. WO 2013/024778
Patent Literature 5: Japanese Patent Laid-Open No. 2004-177668
Patent Literature 6: Japanese Patent Laid-Open No. 2004-271838
Patent Literature 7: Japanese Patent Laid-Open No. 2005-250434
Patent Literature 8: International Publication No. WO 2013/024779
Patent Literature 9: Japanese Patent Laid-Open No. 2002-334869
Patent Literature 10: International Publication No. WO 2004/066377
Patent Literature 11: Japanese Patent Laid-Open No. 2007-226170
Patent Literature 12: Japanese Patent Laid-Open No. 2007-226204
Patent Literature 13: Japanese Patent Laid-Open No. 2010-138393
Patent Literature 14: Japanese Patent Laid-Open No. 2015-174877

Non Patent Literature

Non Patent Literature 1: T. Nakayama, M. Nomura, K. Haga, M. Ueda: Bull. Chem. Soc. Jpn., 71, 2979 (1998)
Non Patent Literature 2: Shinji Okazaki et al., "New Trends of Photoresists", CMC Publishing Co., Ltd., September 2009, pp. 211-259

SUMMARY OF INVENTION

However, it has still been required for film forming materials for lithography or optical component forming materials to have high levels of solubility in organic solvents, etching resistance and resist pattern formability at the same time.

Therefore, the present invention has an object to provide a new compound that is particularly useful as a film forming material for lithography or an optical component forming material and a resin obtained by using this new compound as a monomer, a composition, a method for forming a resist pattern, a method for forming an insulating film, a method for forming a circuit pattern, and a method for purifying the above compound or resin.

The present inventors have, as a result of devoted examinations to solve the problems described above, found out that a new compound having a specific structure is particularly useful as a film forming material for lithography or an optical component forming material, leading to completion of the present invention.

More specifically, the present invention is as follows.

[1]

A compound represented by the following formula (1):

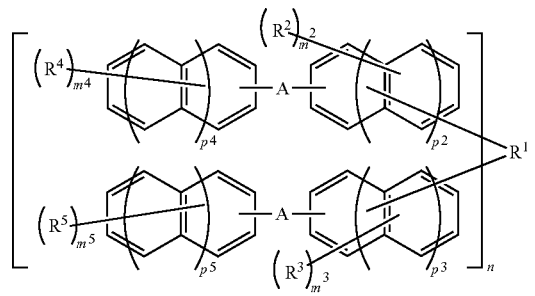

(1)

wherein A is a group containing a heteroatom; $R^1$ is a 2n-valent group having 1 to 30 carbon atoms and optionally having a substituent; $R^2$ to $R^5$ are each independently a linear, branched or cyclic alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 1 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond and at least one $R^4$ and/or at least one $R^3$ is a hydroxy group and/or a thiol group; $m^2$ and $m^3$ are each independently an integer of 0 to 8; $m^4$ and $m^3$ are each independently an integer of 0 to 9; n is an integer of 1 to 4; and $p^2$ to $p^5$ are each independently an integer of 0 to 2.

[2]

The compound according to [1], wherein, in the above formula (1), at least one $R^2$ and/or at least one $R^3$ is a hydroxy group and/or a thiol group.

[3]

The compound according to [1] or [2], wherein the compound represented by the above formula (1) is a compound represented by the following formula (1a):

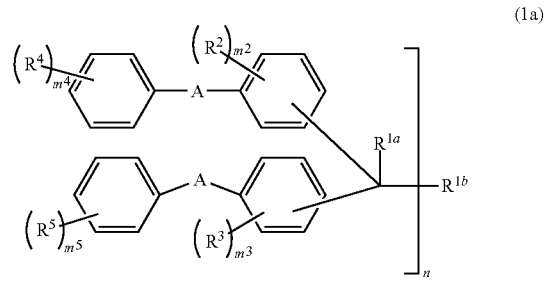

(1a)

wherein A, $R^2$ to $R^5$ and n are as defined in A, $R^2$ to $R^5$ and n in the above formula (1), respectively; $R^{1a}$ is a hydrogen atom or a monovalent group having 1 to 10 carbon atoms and optionally having a substituent; $R^{1b}$ is a 2n-valent group having 1 to 30 carbon atoms and optionally having a substituent; $m^2$ and $m^3$ are each independently an integer of 0 to 4; and $m^4$ and $m^5$ are each independently an integer of 0 to 5.

[4]

The compound according to [3], wherein the compound represented by the above formula (1a) is a compound represented by the following formula (1b):

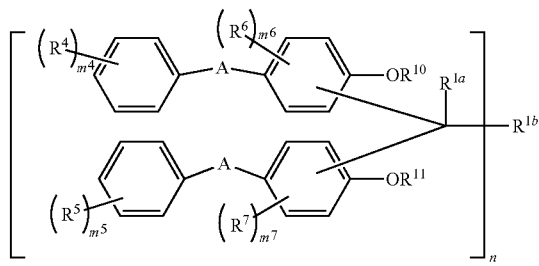

(1b)

wherein A, $R^4$, $R^5$, $R^{1a}$, $R^{1b}$, $m^4$ and $m^5$, and n are as defined in A, $R^4$, $R^5$, $R^{1a}$, $R^{1b}$, $m^4$ and $m^5$, and n in the above formula (1a), respectively; $R^6$ and $R^7$ are each independently an alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 1 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond; $m^6$ and $m^7$ are each independently an integer of 0 to 4; and $R^{10}$ and $R^{11}$ are each a hydrogen atom.

[5]

The compound according to [4], represented by the following formula (1c):

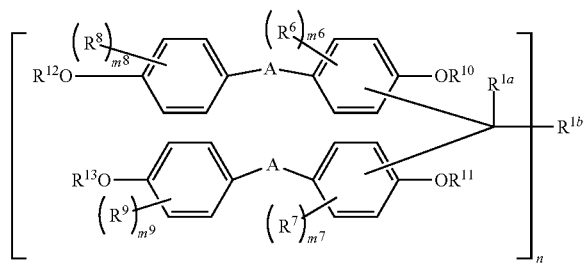

(1c)

wherein A, $R^{1a}$, $R^{1b}$, $R^6$, $R^7$, $R^{10}$, $R^{11}$, $m^6$ and $m^7$, and n are as defined in A, $R^{1a}$, $R^{1b}$, $R^6$, $R^7$, $R^{10}$, $R^{11}$, $m^6$ and $m^7$, and n in the above formula (1b), respectively; $R^8$ and $R^9$ are each independently an alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 1 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond; $R^{12}$ and $R^{13}$ are each independently a hydrogen atom; and $m^8$ and $m^9$ are each independently an integer of 0 to 4.

[6]

A resin obtained using the compound according to any of [1] to [5] as a monomer.

[7]

The resin according to [6], wherein the resin has a structure represented by the following formula (2):

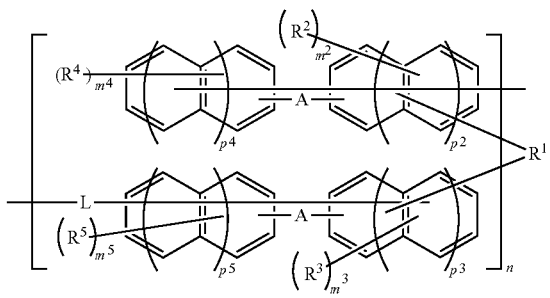

(2)

wherein A, $R^1$ to $R^5$, $m^2$ to $m^5$, n, and $p^2$ to $p^5$ are as defined in A, $R^1$ to $R^5$, $m^2$ to m, n, and $p^2$ to $p^5$ in the above formula (1), respectively; and L is a single bond or a linking group.

[8]

A composition comprising one or more selected from the group consisting of the compound according to any of [1] to [5] and the resin according to [6] or [7].

[9]

The composition according to [8], further comprising a solvent.

[10]

The composition according to [8] or [9], further comprising an acid generating agent.

[11]

The composition according to any of [8] to [10], further comprising a crosslinking agent.

[12]

The composition according to any of [8] to [11], wherein the composition is used in film formation for lithography.

[13]

The composition according to [12] used in film formation for lithography, wherein the composition is used in formation of a photoresist layer.

[14]

The composition according to [12] used in film formation for lithography, wherein the composition is used in formation of a resist underlayer film.

[15]

The composition according to any of [8] to [11], wherein the composition is used in optical component formation.

[16]

A method for forming a resist pattern, comprising the steps of:

forming a resist film on a substrate using the composition according to [13];

exposing at least a portion of the formed resist film; and developing the exposed resist film, thereby forming a resist pattern.

[17]

A radiation-sensitive composition comprising a component (A), which is one or more kinds of the compound and/or the resin according to any of the above [1] to [7], an optically active diazonaphthoquinone compound (B), and a solvent, wherein a content of the solvent is 20 to 99% by mass based on 100% by mass in total of the radiation-sensitive composition, and a content of components except for the solvent is 1 to 80% by mass based on 100% by mass in total of the radiation-sensitive composition.

[18] The radiation-sensitive composition according to [17], wherein a content ratio among the component (A), the optically active diazonaphthoquinone compound (B) and a further optional component (D) optionally contained in the radiation-sensitive composition ((A)/(B)/(D)) is 1 to 99% by mass/99 to 1% by mass/0 to 98% by mass based on 100% by mass of a solid content of the radiation-sensitive composition.

[19] A method for forming a resist pattern, comprising the steps of: forming a resist film on a substrate using the radiation-sensitive composition according to any of the above [17] and [18]; exposing at least a portion of the formed resist film; and developing the exposed resist film, thereby forming a resist pattern.

[20]

The method for forming a resist pattern according to [19], wherein the method is a method for forming a resist permanent film.

[21]

A method for forming a resist pattern, comprising: an underlayer film formation step of forming an underlayer film on a substrate using the composition according to [14];
  a photoresist layer formation step of forming at least one photoresist layer on the underlayer film formed through the underlayer film formation step; and
  a step of irradiating a predetermined region of the photoresist layer formed through the photoresist layer formation step with radiation for development.

[22]

A method for forming a circuit pattern, comprising: an underlayer film formation step of forming an underlayer film on a substrate using the composition according to [14];
  an intermediate layer film formation step of forming an intermediate layer film on the underlayer film formed through the underlayer film formation step;
  a photoresist layer formation step of forming at least one photoresist layer on the intermediate layer film formed through the intermediate layer film formation step;
  a resist pattern formation step of irradiating a predetermined region of the photoresist layer formed through the photoresist layer formation step with radiation for development, thereby forming a resist pattern;
  an intermediate layer film pattern formation step of etching the intermediate layer film with the resist pattern formed through the resist pattern formation step as a mask, thereby forming an intermediate layer film pattern;
  an underlayer film pattern formation step of etching the underlayer film with the intermediate layer film pattern formed through the intermediate layer film pattern formation step as a mask, thereby forming an underlayer film pattern; and
  a substrate pattern formation step of etching the substrate with the underlayer film pattern formed through the underlayer film pattern formation step as a mask, thereby forming a pattern on the substrate.

[23]

A method for purifying the compound according to any of [1] to [5] or the resin according to [6] or [7], comprising:
  an extraction step of bringing a solution containing the compound or the resin and an organic solvent that does not inadvertently mix with water into contact with an acidic aqueous solution, thereby carrying out extraction.

The present invention can provide a new compound that is particularly useful as a film forming material for lithography or an optical component forming material and a resin obtained by using this new compound as a monomer, a composition, a method for forming a resist pattern, a method for forming an insulating film, a method for forming a circuit pattern, and a method for purifying the above compound or resin.

DESCRIPTION OF EMBODIMENTS

Hereinafter, an embodiment of the present invention will be described (hereinafter, referred to as the "present embodiment"). The embodiment described below is given merely for illustrating the present invention. The present invention is not limited only by this embodiment.

[Compound]

A compound of the present embodiment is a compound represented by the following formula (1). The compound of the present embodiment has, for example, the following characteristics (1) to (4).

(1) The compound of the present embodiment has excellent solubility in an organic solvent (particularly, a safe solvent). Therefore, for example, when the compound of the present embodiment is used as a film forming material for lithography, films for lithography can be formed by a wet process such as spin coating or screen printing.

(2) In the compound of the present embodiment, the carbon concentration is relatively high and the oxygen concentration is relatively low. In addition, since the compound of the present embodiment has a phenolic hydroxy group and/or a phenolic thiol group in the molecule, it is useful for formation of a cured product through the reaction with a curing agent, but it can also form a cured product on its own through the crosslinking reaction of the phenolic hydroxy group and/or the phenolic thiol group upon baking at a high temperature. Due to the above, the compound of the present embodiment can exhibit high heat resistance, and when the compound of the present embodiment is used as a film forming material for lithography, degradation of the film upon baking at a high temperature is suppressed and a film for lithography excellent in etching resistance to oxygen plasma etching and the like can be formed.

(3) The compound of the present embodiment can exhibit high heat resistance and etching resistance, as described above, and also has excellent adhesiveness to a resist layer and a resist intermediate layer film material. Therefore, when the compound of the present embodiment is used as a film forming material for lithography, films for lithography excellent in resist pattern formability can be formed. The term "resist pattern formability" herein refers to a property in which there are no major defects in the resist pattern shape and both resolution and sensitivity are excellent.

(4) The compound of the present embodiment has a high refractive index due to its high aromatic ring density, and even after a heat treatment, coloration is suppressed and transparency is excellent.

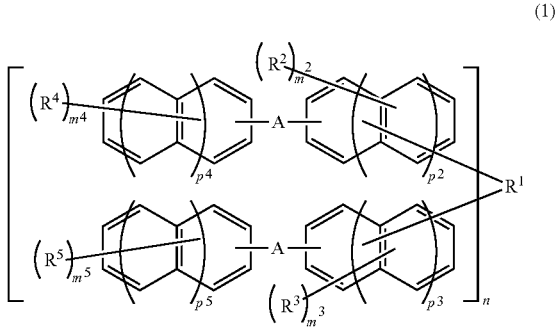

(1)

In the formula (1), A is a group containing a heteroatom; $R^1$ is a 2n-valent group having 1 to 30 carbon atoms and optionally having a substituent; $R^2$ to $R^5$ are each independently a linear, branched or cyclic alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 1 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond and at least one $R^4$ and/or at least one $R^5$ is a hydroxy group and/or a thiol group; $m^2$ and $m^3$ are each independently an integer of 0 to 8; $m^4$ and $m^5$ are each independently an integer of 0 to 9; n is an integer of 1 to 4; and $p^2$ to $p^5$ are each independently an integer of 0 to 2.

In the formula (1), A is a group containing a heteroatom, and is a divalent group containing at least one atom selected from oxygen, nitrogen, sulfur, fluorine, chlorine, bromine and iodine, other than a carbon atom and a hydrogen atom. The heteroatom contained in A is, for example, a heteroatom, the raw materials for which are easily available, and examples thereof include a sulfur atom and an oxygen atom.

In the formula (1), $R^1$ is a 2n-valent group having 1 to 30 carbon atoms, and each aromatic ring is bonded via this $R^1$. Specific examples of the 2n-valent group will be mentioned later.

In the formula (1), $R^2$ to $R^5$ are each independently a linear, branched or cyclic alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 2 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond. However, at least one $R^4$ and/or at least one $R^3$ is a hydroxy group and/or a thiol group.

In the formula (1), $m^2$ and $m^3$ are each independently an integer of 0 to 8, preferably an integer of 0 to 4, and more preferably 1 or 2. $m^4$ and $m^3$ are each independently an integer of 0 to 9, preferably an integer of 0 to 4, and more preferably 1 or 2.

In the formula (1), n is an integer of 1 to 4, and is preferably an integer of 1 to 2.

In the formula (1), $p^2$ to $p^5$ are each independently an integer of 0 to 2, preferably an integer of 0 or 1, and more preferably 0.

Examples of the 2n-valent group include a divalent hydrocarbon group having 1 to 30 carbon atoms (for example, a linear or branched hydrocarbon group or a cyclic hydrocarbon group, such as an alkylene group) when n is 1; a tetravalent hydrocarbon group having 1 to 30 carbon atoms (for example, a linear or branched hydrocarbon group or a cyclic hydrocarbon group, such as an alkanetetrayl group) when n is 2; a hexavalent hydrocarbon group having 2 to 30 carbon atoms (for example, a linear or branched hydrocarbon group or a cyclic hydrocarbon group, such as an alkanehexayl group) when n is 3; and an octavalent hydrocarbon group having 3 to 30 carbon atoms (for example, a linear or branched hydrocarbon group or a cyclic hydrocarbon group, such as an alkaneoctayl group) when n is 4. Here, the above cyclic hydrocarbon group may have a bridged cyclic hydrocarbon group or an aromatic group.

Also, the above 2n-valent group (for example, a 2n-valent hydrocarbon group) may have a double bond or may have a heteroatom.

In the formula (1), with respect to $R^2$ to $R^5$, the alkyl group having 1 to 30 carbon atoms and optionally having a substituent may be, for example, an unsubstituted methyl group, ethyl group, n-propyl group, i-propyl group, n-butyl group, i-butyl group, t-butyl group, cyclopropyl group, cyclobutyl group or the like, or alternatively, examples thereof include a methyl group, an ethyl group, a n-propyl group, an i-propyl group, a n-butyl group, an i-butyl group, a t-butyl group, a cyclopropyl group and a cyclobutyl group, having a substituent such as a halogen atom, a nitro group, an amino group, a thiol group, a hydroxy group, or a group in which a hydrogen atom of a hydroxy group is replaced with an acid dissociation group.

The aryl group having 6 to 30 carbon atoms and optionally having a substituent may be, for example, an unsubstituted phenyl group, naphthalene group, biphenyl group or the like, or alternatively, examples thereof include a phenyl group, a naphthalene group and a biphenyl group, having a substituent such as a halogen atom, a nitro group, an amino group, a thiol group, a hydroxy group, or a group in which a hydrogen atom of a hydroxy group is replaced with an acid dissociation group.

The alkenyl group having 2 to 30 carbon atoms and optionally having a substituent may be, for example, an unsubstituted propenyl group, butenyl group or the like, or alternatively, examples thereof include a propenyl group and a butenyl group, having a substituent such as a halogen atom, a nitro group, an amino group, a thiol group, a hydroxy group, or a group in which a hydrogen atom of a hydroxy group is replaced with an acid dissociation group.

The alkynyl group having 2 to 30 carbon atoms and optionally having a substituent may be, for example, an unsubstituted propynyl group, butynyl group or the like, or alternatively, examples thereof include a propynyl group and a butynyl group, having a substituent such as a halogen atom, a nitro group, an amino group, a thiol group, a hydroxy group, or a group in which a hydrogen atom of a hydroxy group is replaced with an acid dissociation group.

The alkoxy group having 1 to 30 carbon atoms and optionally having a substituent may be, for example, an unsubstituted methoxy group, ethoxy group, propoxy group, cyclohexyloxy group, phenoxy group, naphthalenoxy group, biphenyl group or the like, or alternatively, examples thereof include a methoxy group, an ethoxy group, a propoxy group, a cyclohexyloxy group, a phenoxy group and a naphthalenoxy group, having a substituent such as a halogen atom, a nitro group, an amino group, a thiol group, a hydroxy group, or a group in which a hydrogen atom of a hydroxy group is replaced with an acid dissociation group.

Here, the "dissociation group" refers to a group that is dissociated in the presence of a catalyst or without a catalyst. The acid dissociation group refers to a characteristic group that is cleaved in the presence of an acid to cause a change into an alkali soluble group or the like. Examples of the alkali soluble group include, but not particularly limited to, a group having a phenolic hydroxy group, a group having a carboxyl group, a group having a sulfonic acid group, and a group having a hexafluoroisopropanol group. Among them, a phenolic hydroxy group and a carboxyl group are preferable, and a phenolic hydroxy group is particularly preferable, from the viewpoint of the easy availability of an introduction reagent. The acid dissociation group preferably has the property of causing chained cleavage reaction in the presence of an acid, for achieving pattern formation with high sensitivity and high resolution. The acid dissociation group is not particularly limited, but can be arbitrarily selected for use from among, for example, those proposed in hydroxystyrene resins, (meth)acrylic acid resins, and the like for use in chemically amplified resist compositions for KrF or ArF.

Preferable examples of the acid dissociation group include a group selected from the group consisting of a 1-substituted ethyl group, a 1-substituted n-propyl group, a 1-branched alkyl group, a silyl group, an acyl group, a 1-substituted alkoxymethyl group, a cyclic ether group, an alkoxycarbonyl group, and an alkoxycarbonylalkyl group, which has the property of being dissociated by an acid.

The "crosslinkable group" in the present embodiment refers to a group that crosslinks in the presence of a catalyst or without a catalyst. Examples of the crosslinkable group include, but not particularly limited to, an alkoxy group having 1 to 20 carbon atoms, a group having an allyl group, a group having a (meth)acryloyl group, a group having an epoxy (meth)acryloyl group, a group having a hydroxy group, a group having a urethane (meth)acryloyl group, a group having a glycidyl group, a group having a vinyl containing phenylmethyl group, a group having various alkynyl groups, a group having a carbon-carbon double bond, a group having a carbon-carbon triple bond, and a group containing these groups. Examples of the group containing these groups suitably include an alkoxy group of the group mentioned above —OR$^X$ (R$^X$ is a group having an allyl group, a group having a (meth)acryloyl group, a group having an epoxy (meth)acryloyl group, a group having a hydroxy group, a group having a urethane (meth)acryloyl group, a group having a glycidyl group, a group having a vinyl containing phenylmethyl group, a group having various alkynyl groups, a group having a carbon-carbon double bond, a group having a carbon-carbon triple bond, and a group containing these groups).

Examples of the group having an allyl group include, but not particularly limited to, a group represented by the following formula (X-1).

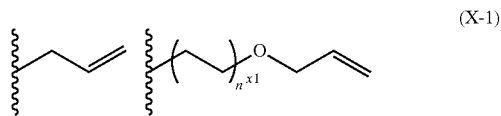

(In the formula (X-1), $n^{x1}$ is an integer of 1 to 5.)

Examples of the group having a (meth)acryloyl group include, but not particularly limited to, a group represented by the following formula (X-2).

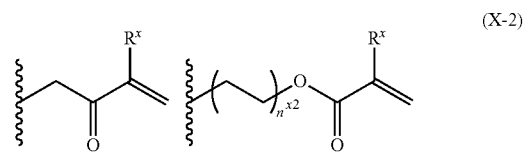

(In the formula (X-2), $n^{x2}$ is an integer of 1 to 5, and R$^X$ is a hydrogen atom or a methyl group.)

Examples of the group having an epoxy (meth)acryloyl group include, but not particularly limited to, a group represented by the following formula (X-3). Here, the epoxy (meth)acryloyl group refers to a group generated through a reaction between an epoxy (meth)acrylate and a hydroxy group.

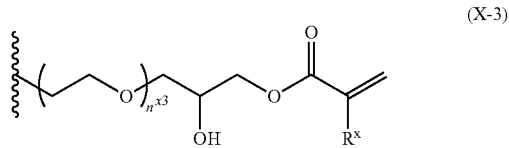

(In the formula (X-3), $n^{x3}$ is an integer of 0 to 5, and R$^X$ is a hydrogen atom or a methyl group.)

Examples of the group having a urethane (meth)acryloyl group include, but not particularly limited to, a group represented by the following formula (X-4).

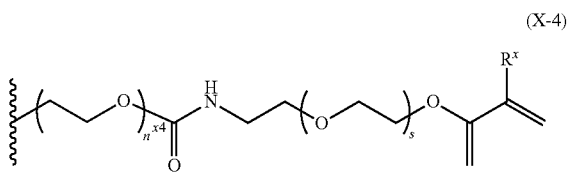

(In the general formula (X-4), $n^{x4}$ is an integer of 0 to 5, s is an integer of 0 to 3, and R$^X$ is a hydrogen atom or a methyl group.)

Examples of the group having a hydroxy group include, but not particularly limited to, a group represented by the following formula (X-5).

(X-5)

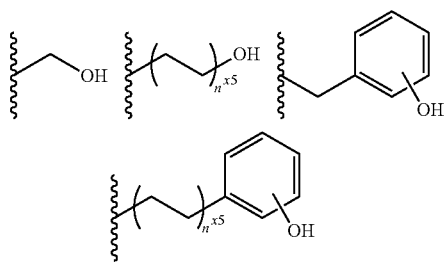

(In the general formula (X-5), $n^{x5}$ is an integer of 1 to 5.)

Examples of the group having a glycidyl group include, but not particularly limited to, a group represented by the following formula (X-6).

(X-6)

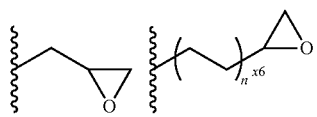

(In the formula (X-6), $n^{x6}$ is an integer of 1 to 5.)

Examples of the group having a vinyl containing phenylmethyl group include, but not particularly limited to, a group represented by the following formula (X-7).

(X-7)

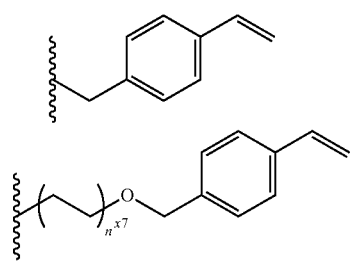

(In the formula (X-7), $n^{x7}$ is an integer of 1 to 5.)

Examples of the group having various alkynyl groups include, but not particularly limited to, a group represented by the following formula (X-8).

(X-8)

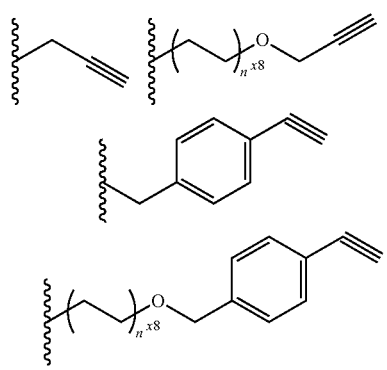

-continued

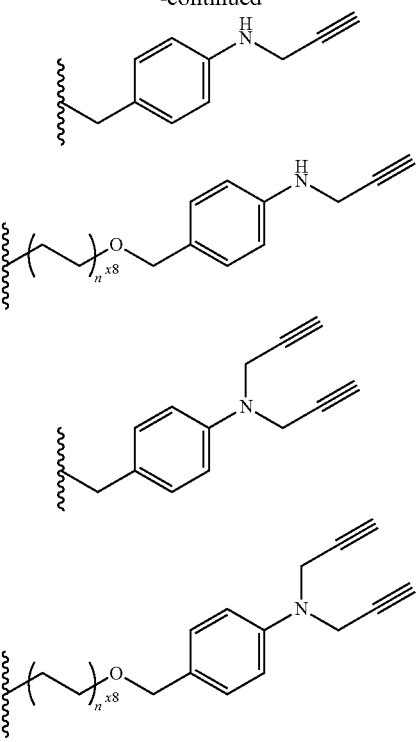

(In the formula (X-8), $n^{x8}$ is an integer of 1 to 5.)

Examples of the above carbon-carbon double bond containing group include a (meth)acryloyl group, a substituted or unsubstituted vinyl phenyl group, and a group represented by the following formula (X-9-1). In addition, examples of the above carbon-carbon triple bond containing group include a substituted or unsubstituted ethynyl group, a substituted or unsubstituted propargyl group, and a group represented by the following formula (X-9-2) or (X-9-3).

(X-9-1)

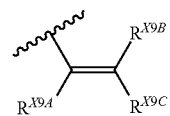

(X-9-2)

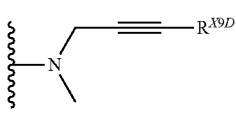

(X-9-3)

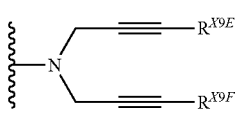

In the above formula (X-9-1), $R^{X9A}$, $R^{X9B}$ and $R^{X9C}$ are each independently a hydrogen atom or a monovalent hydrocarbon group having 1 to 20 carbon atoms. In the above formulas (X-9-2) and (X-9-3), $R^{X9D}$, $R^{X9E}$ and $R^{X9F}$ are each independently a hydrogen atom or a monovalent hydrocarbon group having 1 to 20 carbon atoms.

Among the above, from the viewpoint of ultraviolet curability, a (meth)acryloyl group, an epoxy (meth)acryloyl group, a urethane (meth)acryloyl group, a group having a glycidyl group, and a group containing a styrene group are preferable, a (meth)acryloyl group, an epoxy (meth)acryloyl group and a urethane (meth)acryloyl group are more preferable, and a (meth)acryloyl group is still more preferable. In addition, from the viewpoint of heat resistance, a group having various alkynyl groups is also preferable.

The compound represented by the above formula (1) has high heat resistance attributed to its rigid structure, in spite of its relatively low molecular weight, and can therefore be used even under high temperature baking conditions. Also, the compound represented by the above formula (1) has tertiary carbon or quaternary carbon in the molecule, which suppresses crystallization, and is thus suitably used as a film forming material for lithography.

In addition, the compound represented by the above formula (1) has high solubility in an organic solvent (particularly, a safe solvent) and has excellent heat resistance and etching resistance. For this reason, a film forming material for lithography containing the compound represented by the above formula (1) has excellent resist pattern formability. Examples of the above organic solvent include the organic solvents described in [Solvent] exemplified in the section of [Composition], which will be mentioned later.

Moreover, the compound represented by the above formula (1) has a relatively low molecular weight and a low viscosity, and therefore facilitates enhancing film smoothness while uniformly and completely filling even the steps of an uneven substrate (particularly having fine space, hole pattern, etc.). As a result, a film forming material for lithography containing the compound represented by the above formula (1) has excellent embedding properties and smoothing properties. In addition, the compound represented by the above formula (1) is a compound that has a relatively high carbon concentration, and can therefore exhibit high etching resistance, as well.

In addition, the compound represented by the above formula (1) has high refractive index ascribable to its high aromatic ring density and is prevented from being stained by heat treatment in a wide range from a low temperature to a high temperature. Therefore, the compound represented by the formula (1) is also useful as various optical component forming materials. The compound represented by the above formula (1) preferably has quaternary carbon from the viewpoint of preventing the compound from being oxidatively decomposed and stained and improving heat resistance and solvent solubility.

The above optical component may be in the form of a film or a sheet, and examples thereof include a plastic lens (for example, a prism lens, a lenticular lens, a microlens, a Fresnel lens, a viewing angle control lens, a contrast improving lens, etc.), a phase difference film, a film for electromagnetic wave shielding, a prism, an optical fiber, a solder resist for flexible printed wiring, a plating resist, an interlayer insulating film for multilayer printed circuit boards, a photosensitive optical waveguide, a liquid crystal display, an organic electroluminescent (EL) display, an optical semiconductor (LED) element, a solid state image sensing element, an organic thin film solar cell, a dye sensitized solar cell, and an organic thin film transistor (TFT). The compound represented by the formula (1) is suitably used as a material for forming an embedded film and a smoothed film on a photodiode, a smoothed film in front of or behind a color filter, a microlens, and a smoothed film and a conformal film on a microlens, all of which are members of a solid state image sensing element, to which high refractive index is demanded.

In the compound represented by the above formula (1), it is preferable that at least one $R^2$ and/or at least one $R^3$ be a hydroxy group and/or a thiol group from the viewpoint of easy crosslinking reaction and solubility in an organic solvent.

The compound represented by the above formula (1) is preferably a compound represented by the following formula (1-1) from the viewpoint of easy crosslinking and solubility in an organic solvent.

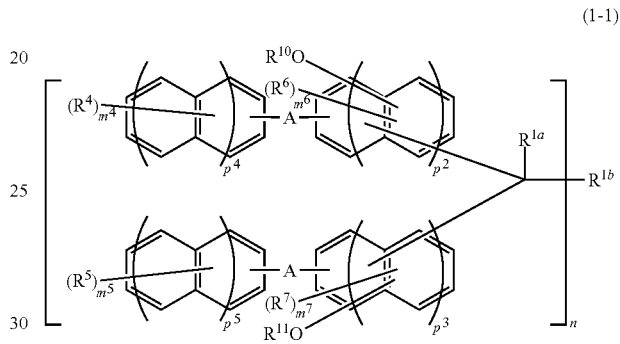

(1-1)

In the above formula (1-1), A, $R^4$, $R^5$, n, $p^2$ to $p^5$, $m^4$ and $m^5$, and n are as defined in A, $R^4$, $R^5$, n, $p^2$ to $p^5$, $m^4$ and $m^5$, and n in the formula (1), respectively; $R^{1a}$ is a hydrogen atom or a monovalent group having 1 to 10 carbon atoms; $R^{1b}$ is a 2n-valent group having 1 to 30 carbon atoms; and $R^6$ to $R^7$ are each independently an alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 2 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond. $R^{10}$ to $R^{11}$ are each a hydrogen atom, and $m^6$ and $m^7$ are each independently an integer of 0 to 7. Examples of the monovalent group having 1 to 10 carbon atoms include a monovalent hydrocarbon group having 1 to 10 carbon atoms such as a methyl group, an ethyl group, a n-propyl group, an i-propyl group, a n-butyl group, an i-butyl group, a t-butyl group, a n-pentyl group, a neopentyl group, a cyclopentyl group, a n-hexyl group, a cyclohexyl group and a phenyl group, and examples of the 2n-valent group having 1 to 30 carbon atoms include the 2n-valent groups exemplified as $R^1$ in the above formula (1).

In addition, the compound represented by the above formula (1-1) is preferably a compound represented by the following formula (1-2) from the viewpoint of easy crosslinking and solubility in an organic solvent.

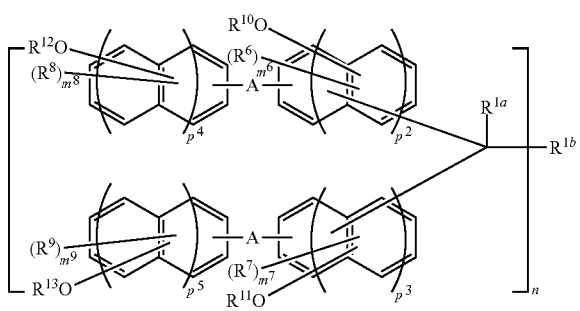

(1-2)

In the above formula (1-2), A, $R^{1a}$, $R^{1b}$, $R^6$, $R^7$, $R^{10}$, $R^{11}$, n, $p^2$ to $p^5$, $m^6$ and $m^7$ are as defined in A, $R^{1a}$, $R^{1b}$, $R^6$, $R^7$, $R^{10}$, $R^{11}$, n, $p^2$ to $p^5$, $m^6$ and $m^7$ in the formula (1-1), respectively; and $R^8$ to $R^9$ are each independently an alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 2 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond. $R^{12}$ to $R^{13}$ are each independently a hydrogen atom, and $m^8$ and $m^9$ are each independently an integer of 0 to 8.

In addition, the compound represented by the above formula (1) is preferably a compound represented by the following formula (1a) from the viewpoint of the supply of raw materials.

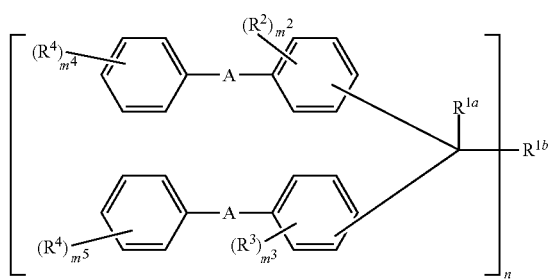

(1a)

In the above formula (1a), A, $R^2$ to $R^5$ and n are as defined in A, $R^2$ to $R^5$ and n in the above formula (1), respectively; $R^{1a}$ is a hydrogen atom or a monovalent group having 1 to 10 carbon atoms; $R^{1b}$ is a 2n-valent group having 1 to 30 carbon atoms; $m^2$ and $m^3$ are each independently an integer of 0 to 4; and $m^4$ and $m^3$ are each independently an integer of 0 to 5. Examples of the monovalent group having 1 to 10 carbon atoms include an alkyl group and an aryl group, and include a monovalent hydrocarbon group having 1 to 10 carbon atoms such as a methyl group, an ethyl group, a n-propyl group, an i-propyl group, a n-butyl group, an i-butyl group, a t-butyl group, a n-pentyl group, a neopentyl group, a cyclopentyl group, a n-hexyl group, a cyclohexyl group and a phenyl group, and examples of the 2n-valent group having 1 to 30 carbon atoms include the 2n-valent groups exemplified as $R^1$ in the above formula (1).

The compound represented by the above formula (1a) is more preferably a compound represented by the following formula (1b) from the viewpoint of solubility in an organic solvent.

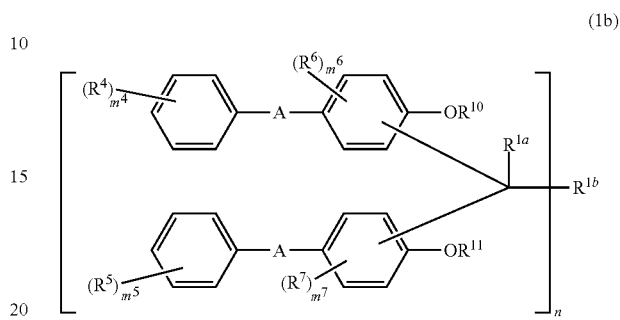

(1b)

In the above formula (1b), A, $R^4$, $R^5$, $R^{1a}$, $R^{1b}$, $m^4$ and m, and n are as defined in A, $R^4$, $R^5$, $R^{1a}$, $R^{1b}$, $m^4$ and $m^5$, and n in the above formula (1a), respectively; and $R^6$ and $R^7$ are each independently an alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 2 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond. $m^6$ and $m^7$ are each independently an integer of 0 to 4, and $R^{10}$ and $R^{11}$ are each a hydrogen atom.

The compound represented by the above formula (1b) is further preferably a compound represented by the following formula (1c) from the viewpoint of solubility in an organic solvent.

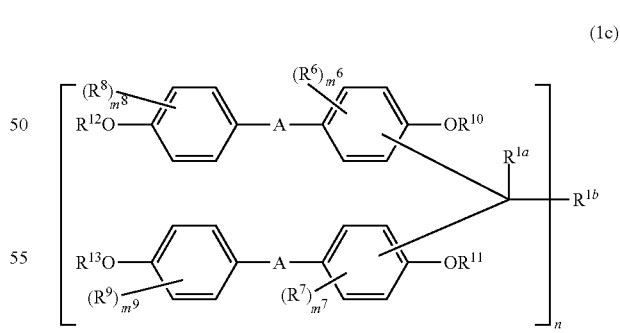

(1c)

In the above formula (1c), A, $R^{1a}$, $R^{1b}$, $R^6$, $R^7$, $R^{10}$, $R^{11}$, $m^6$ and $m^7$, and n are as defined in A, $R^{1a}$, $R^{1b}$, $R^6$, $R^7$, $R^{10}$, $R^{11}$, $m^6$ and $m^7$, and n in the above formula (1b), respectively; and $R^8$ and $R^9$ are each an alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 2 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond. $R^{12}$ and $R^{13}$ are each independently a hydrogen atom, and $m^8$ and $m^9$ are each independently an integer of 0 to 4.

The compound represented by the above formula (1c) is particularly preferably a compound represented by any of the following formulas (BisF-1) to (BisF-3) and (BiF-1) to (BiF-7) from the viewpoint of further solubility in an organic solvent.

(BisF-1)

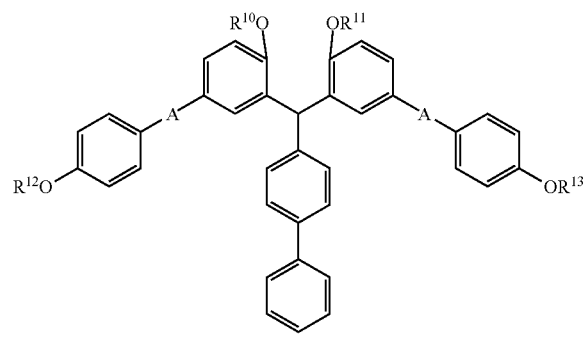

In the above (BisF-1), A and $R^{10}$ to $R^{13}$ are as defined in A and $R^{10}$ to $R^{13}$ in the above formula (1c), respectively.

(BisF-2)

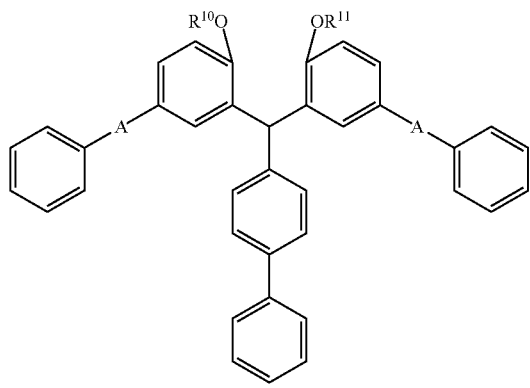

In the above (BisF-2), A and $R^{10}$ to $R^{11}$ are as defined in A and $R^{10}$ to $R^{11}$ in the above formula (1c), respectively.

(BisF-3)

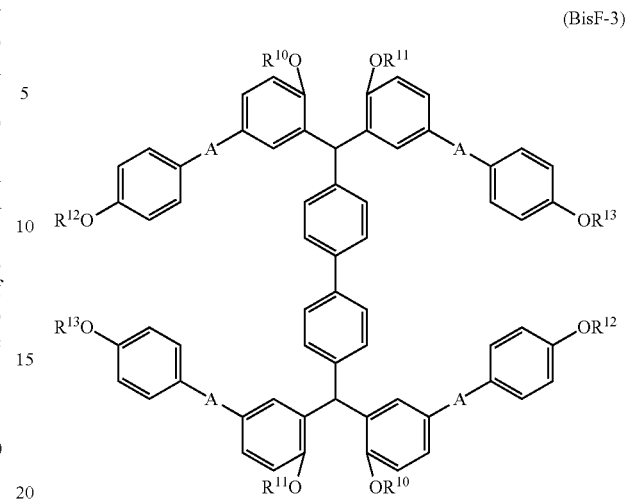

In the above (BisF-3), A and $R^{10}$ to $R^{13}$ are as defined in A and $R^{10}$ to $R^{13}$ in the above formula (1c), respectively.

(BiF-1)

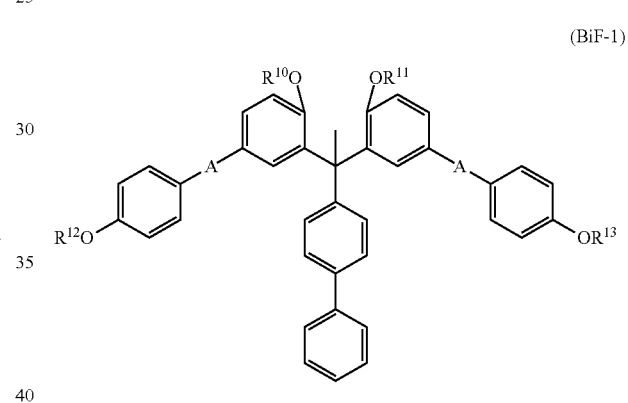

In the above (BiF-1), A and $R^{10}$ to $R^{13}$ are as defined in A and $R^{10}$ to $R^{13}$ in the above formula (1c), respectively.

(BiF-2)

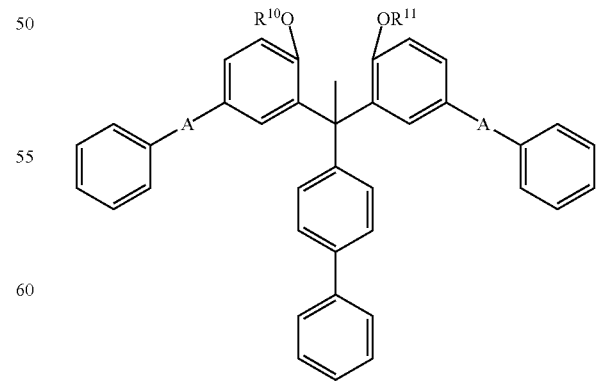

In the above (BiF-2), A and $R^{10}$ to $R^{11}$ are as defined in A and $R^{10}$ to $R^{11}$ in the above formula (1c), respectively.

(BiF-3)

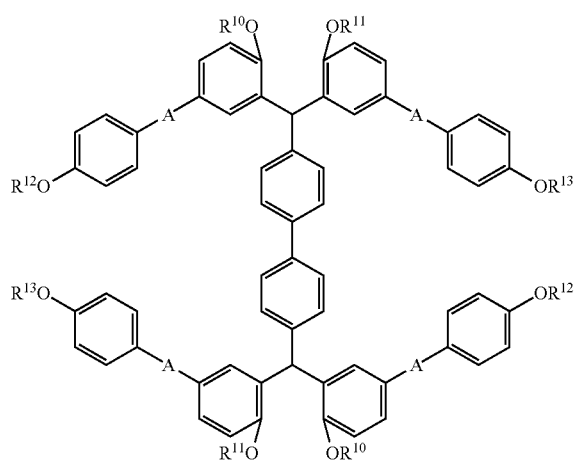

In the above (BiF-3), A and R[10] to R[13] are as defined in A and R[10] to R[13] in the above formula (1c), respectively.

(BiF-4)

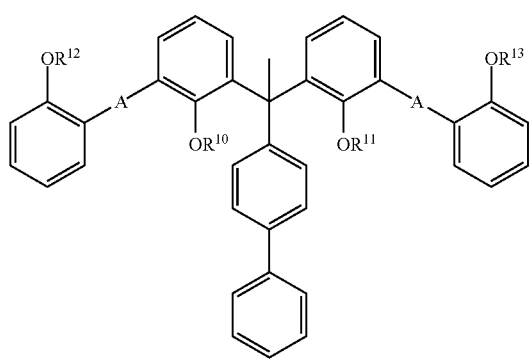

In the above (BiF-4), A and R[10] to R[13] are as defined in A and R[10] to R[13] in the above formula (1c), respectively.

(BiF-5)

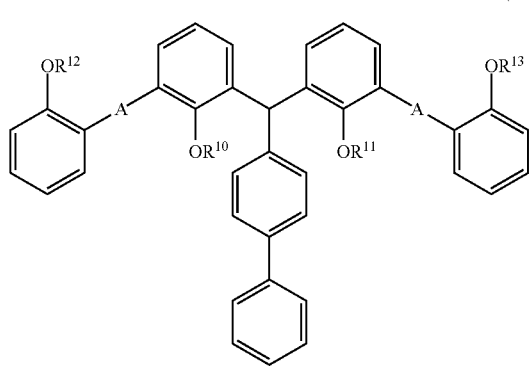

In the above (BiF-5), A and R[10] to R[13] are as defined in A and R[10] to R[13] in the above formula (1c), respectively.

(BiF-6)

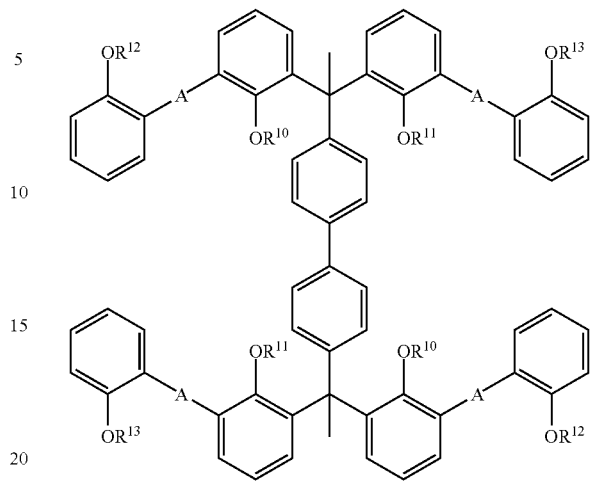

In the above (BiF-6), A and R[10] to R[13] are as defined in A and R[10] to R[13] in the above formula (1c), respectively.

(BiF-7)

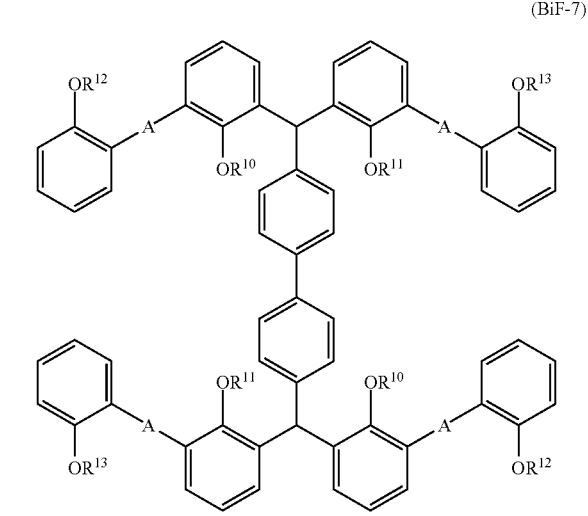

In the above (BiF-7), A and R[10] to R[13] are as defined in A and R[10] to R[13] in the above formula (1c), respectively.

The compound represented by the formula (1) is preferably a compound selected from the group represented by the following formulas from the viewpoint of heat resistance and solubility in an organic solvent.

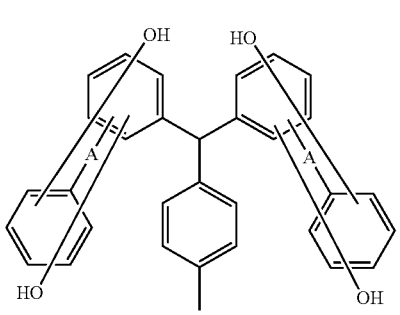

-continued
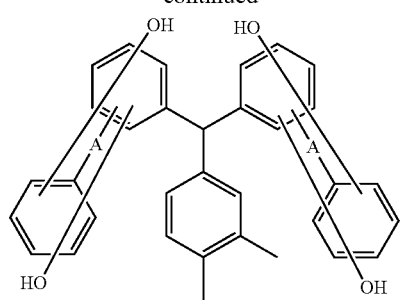
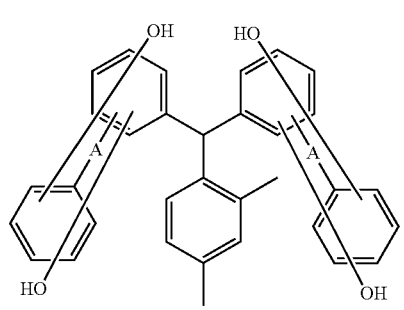
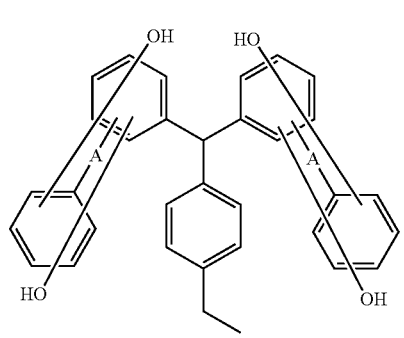
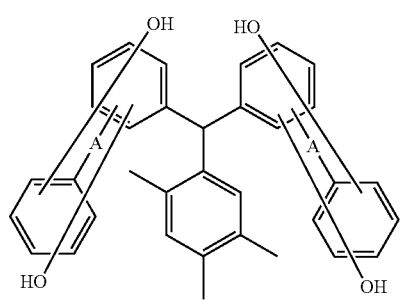
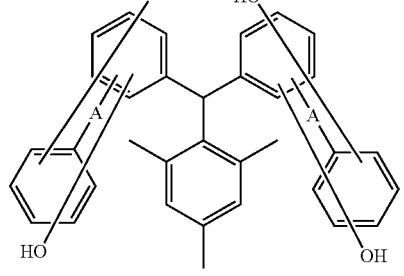
-continued
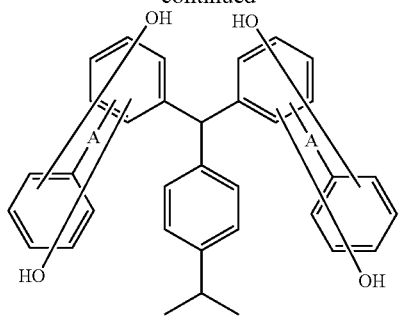
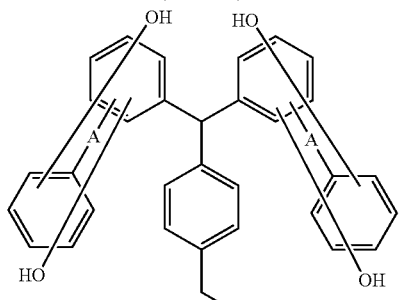
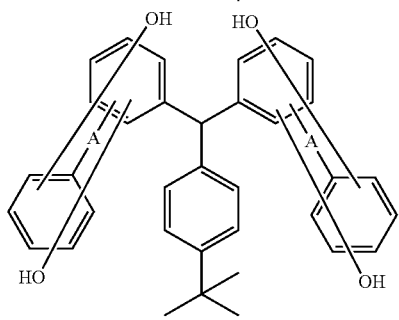
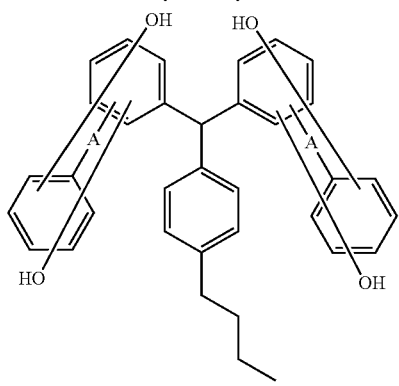
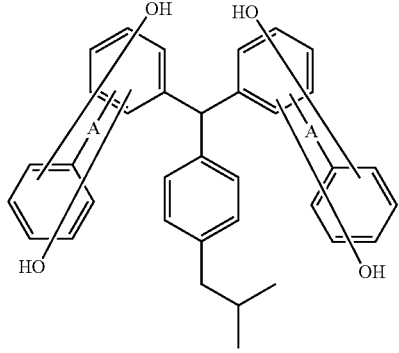

-continued
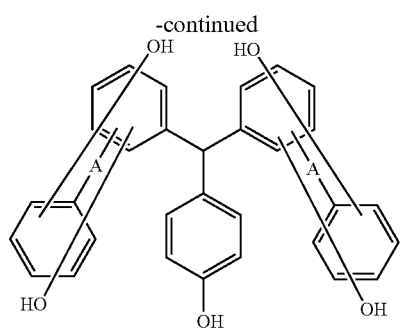
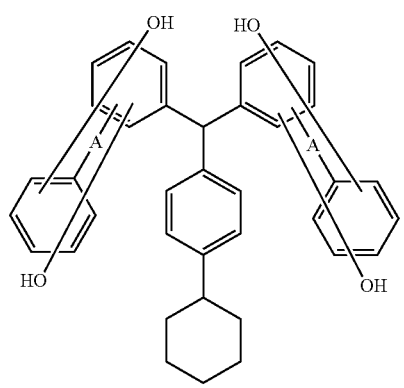
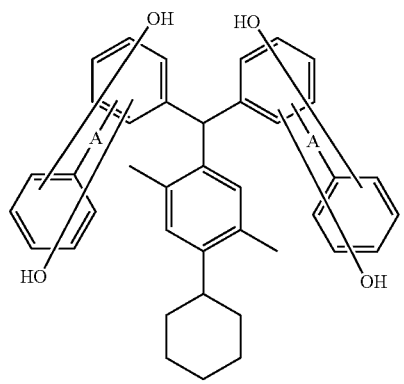
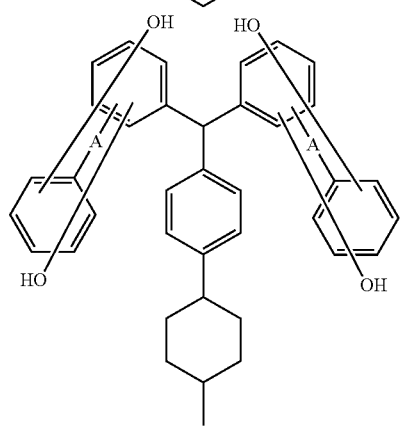
-continued
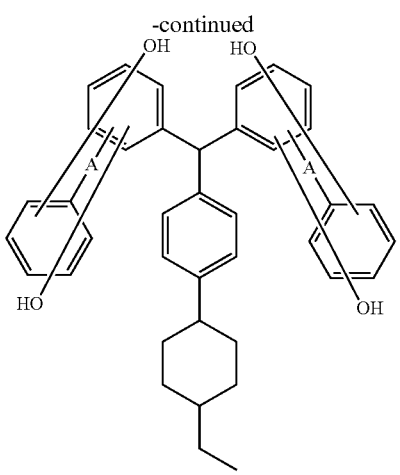
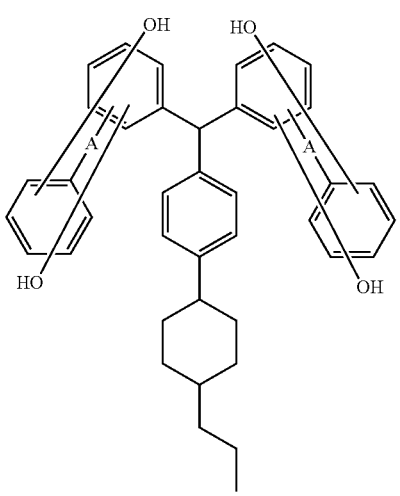
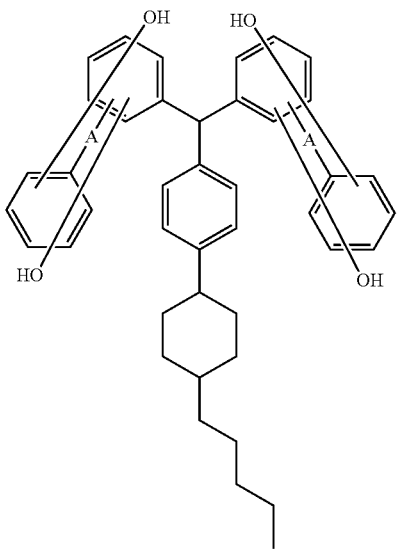

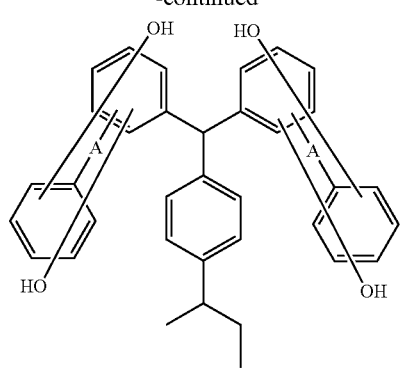
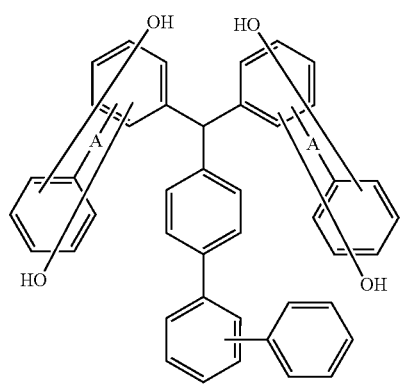
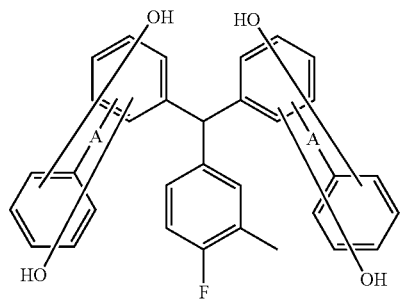
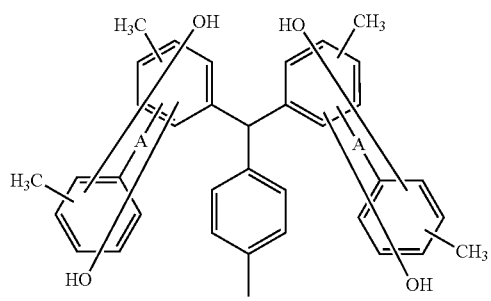
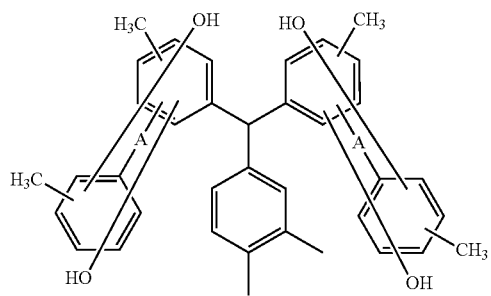
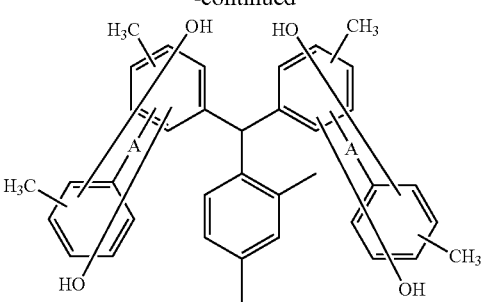
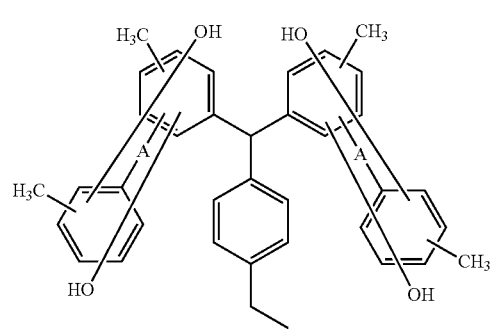
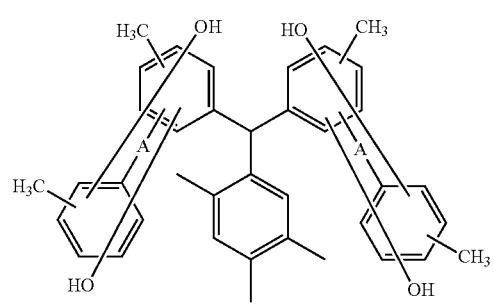
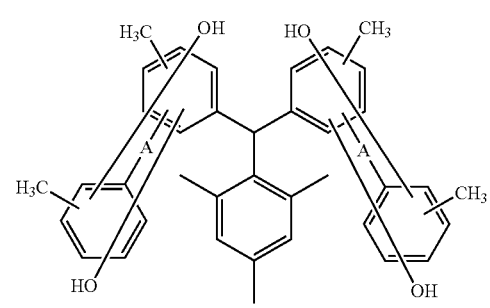
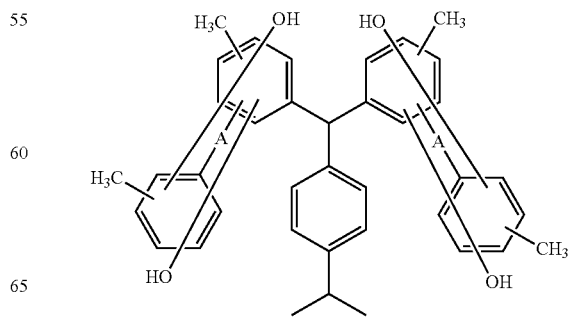

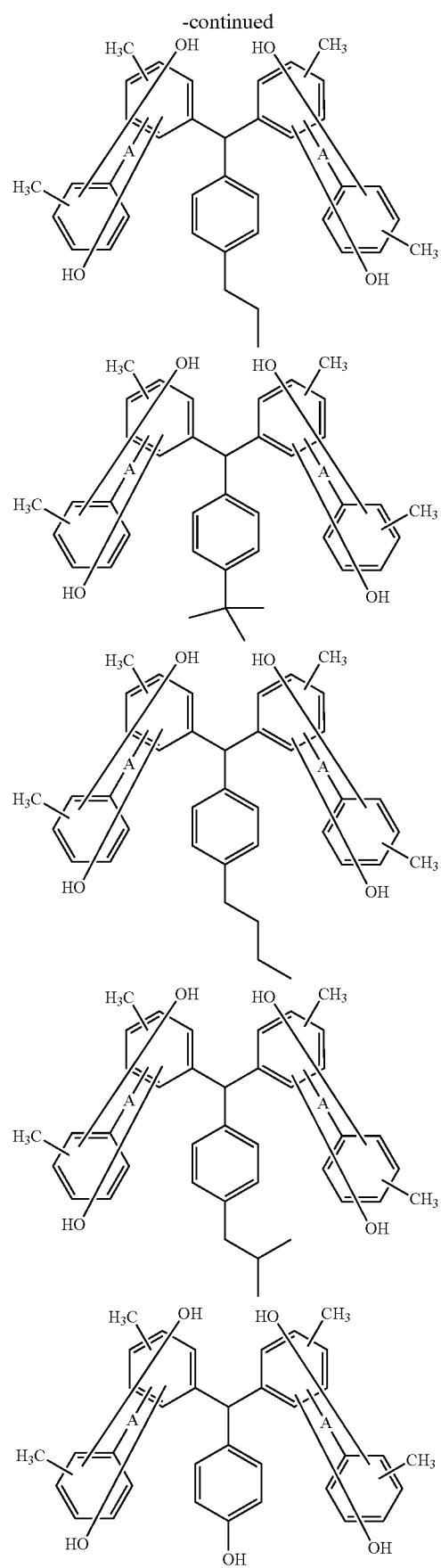
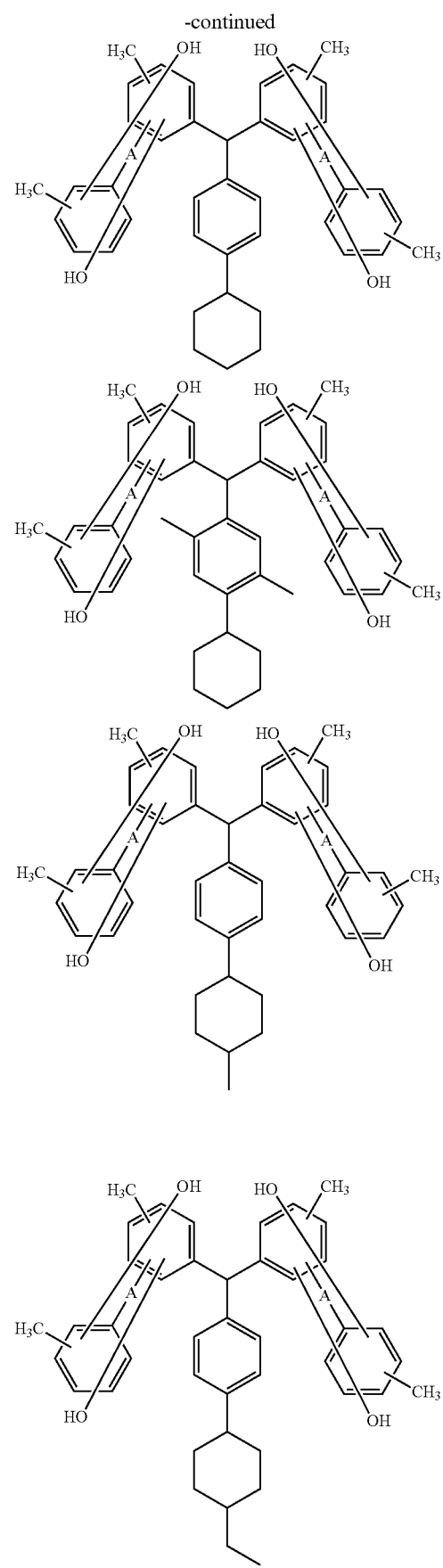

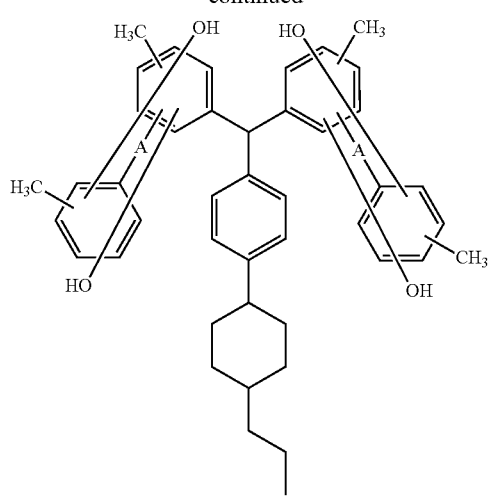
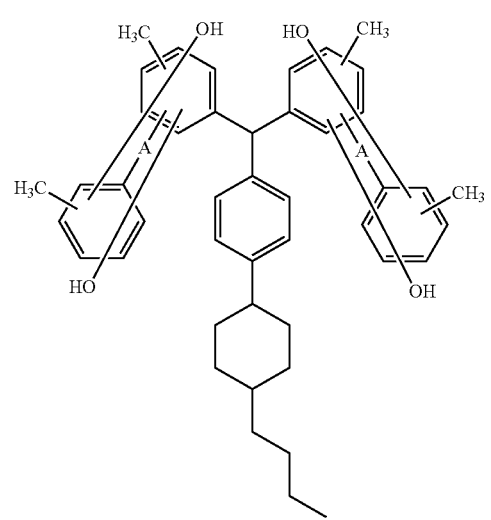
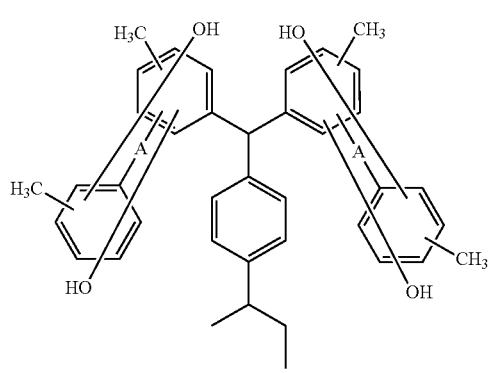
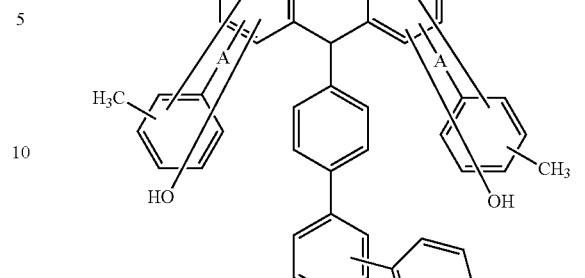
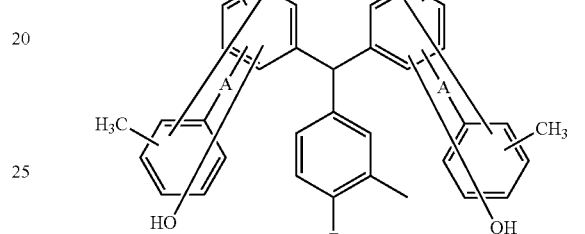
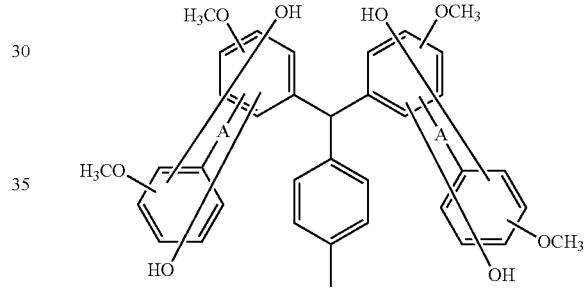
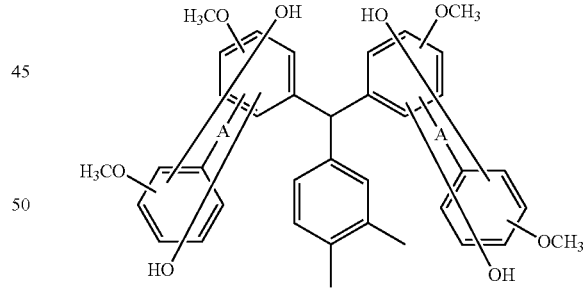
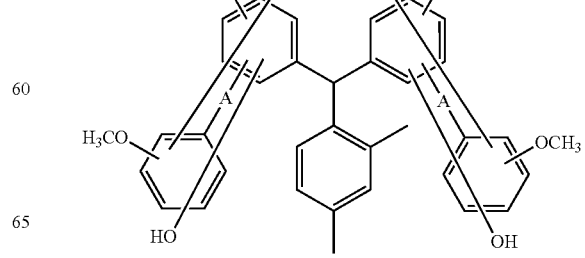

-continued
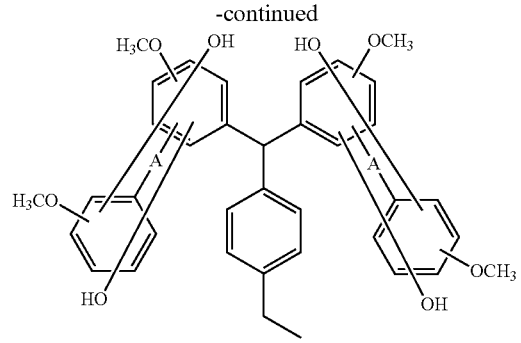
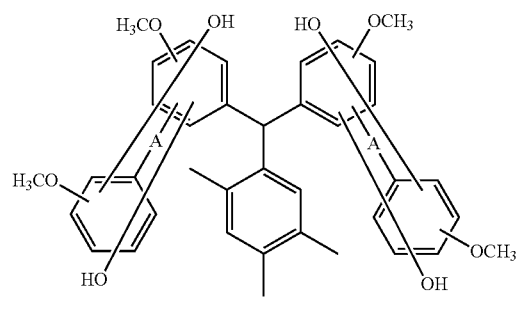
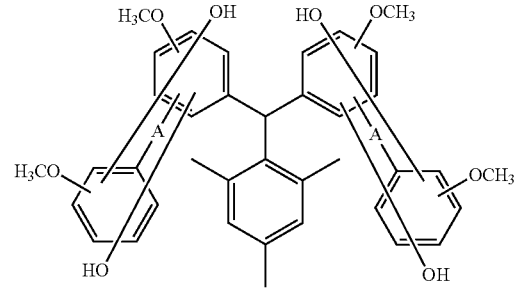
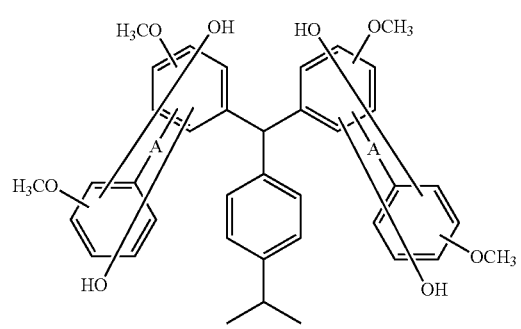
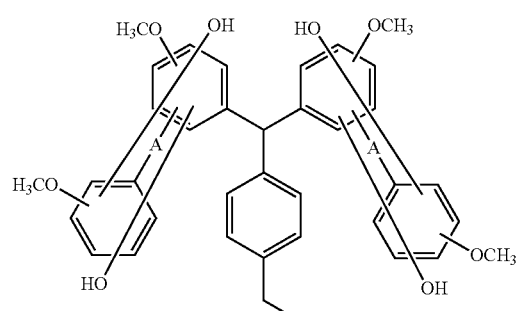
-continued
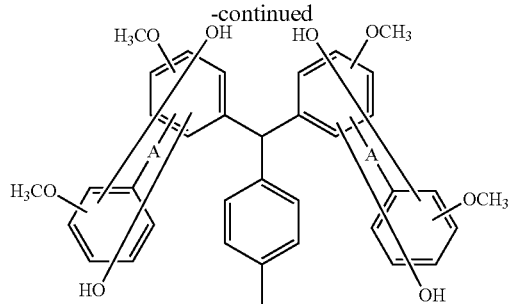
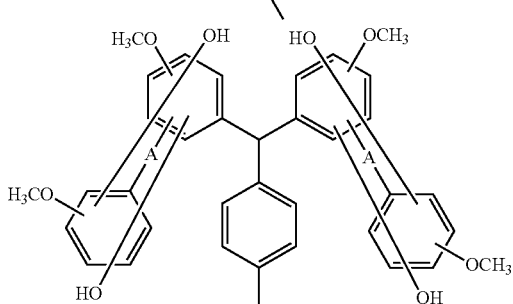
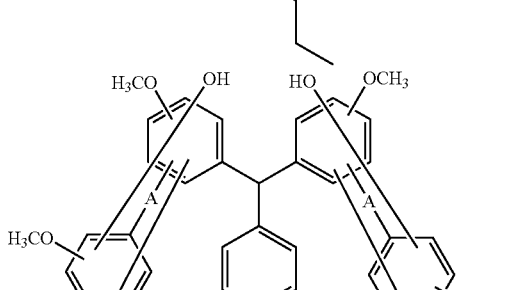
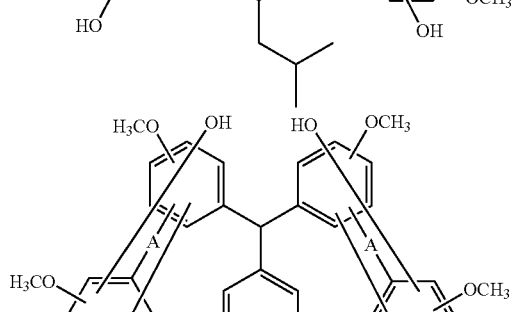
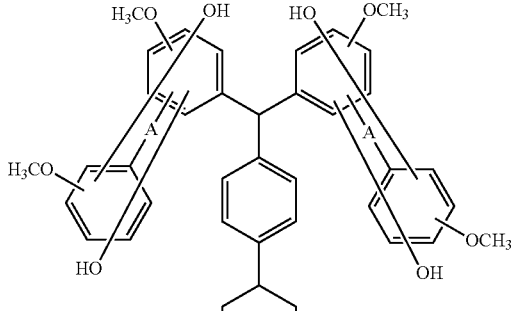

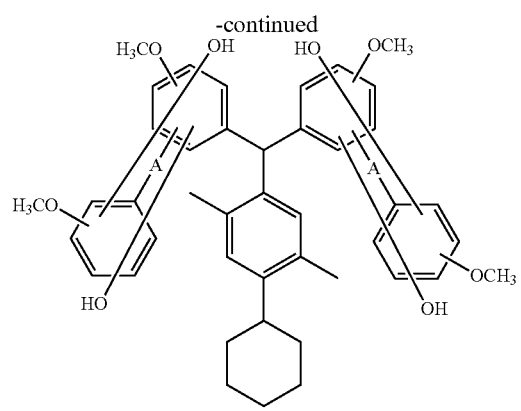
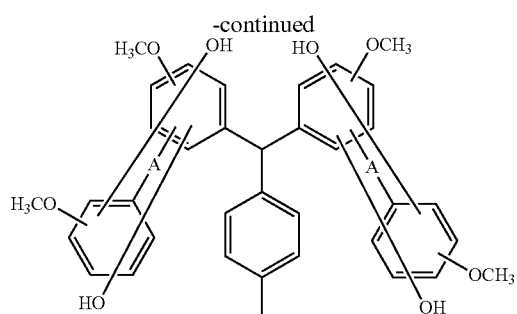
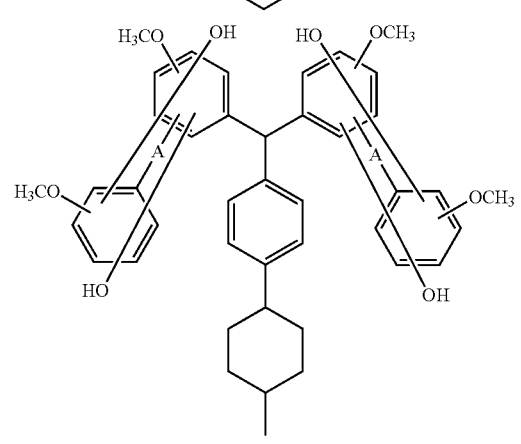
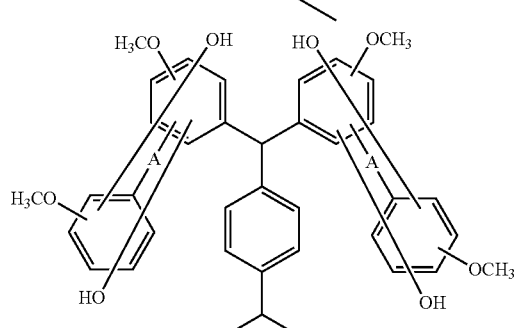
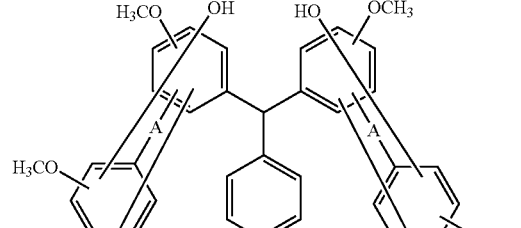
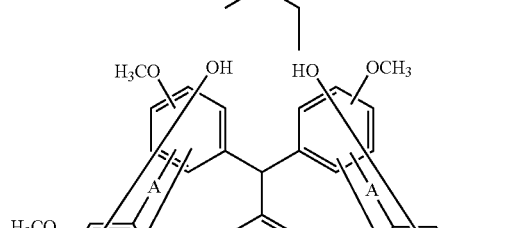
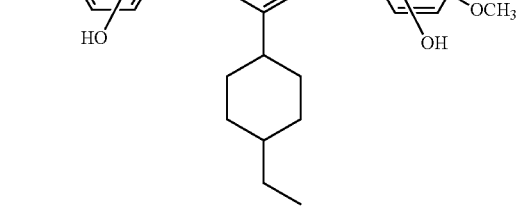
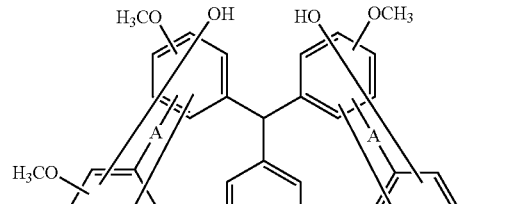
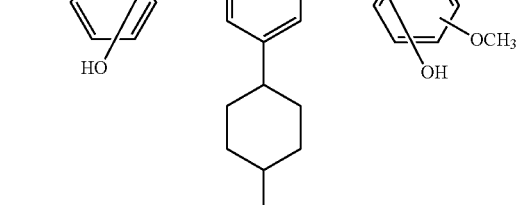
In each of the above formulas, A is as defined in A in the above formula (1).
Specific examples of the compound represented by the above formula (1) include compounds represented by the following formulas. However, the compound represented by the above formula (1) is not limited to the compounds represented by the following formulas.
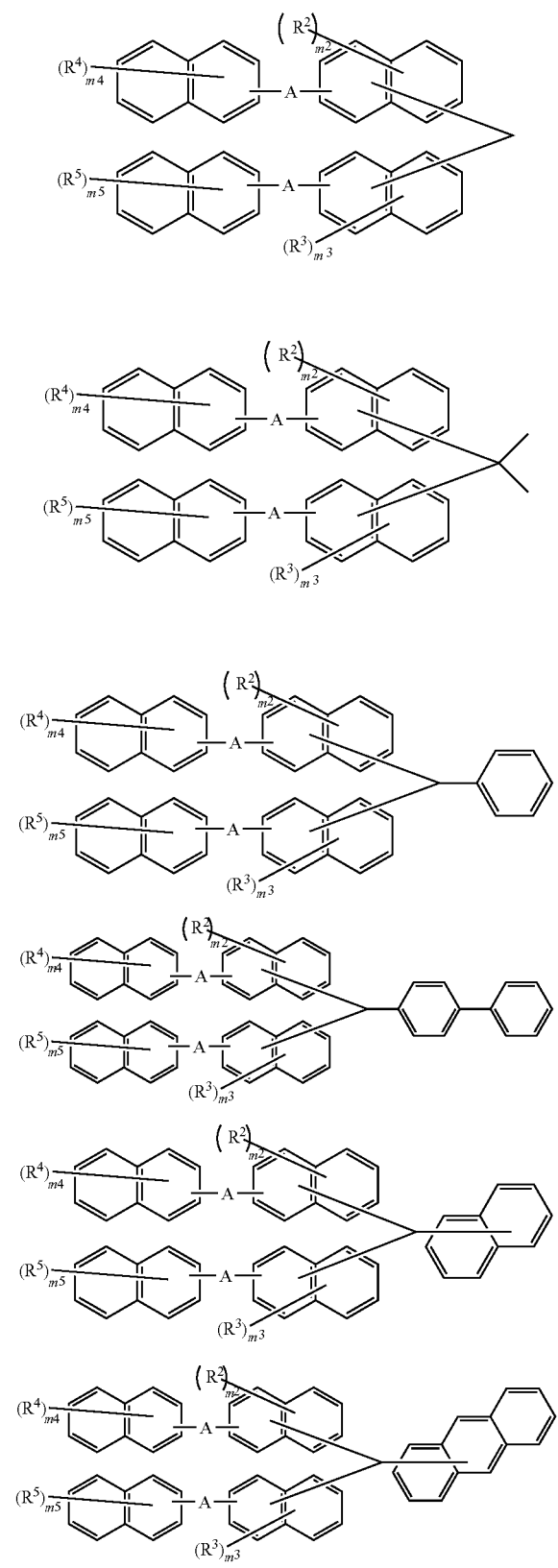
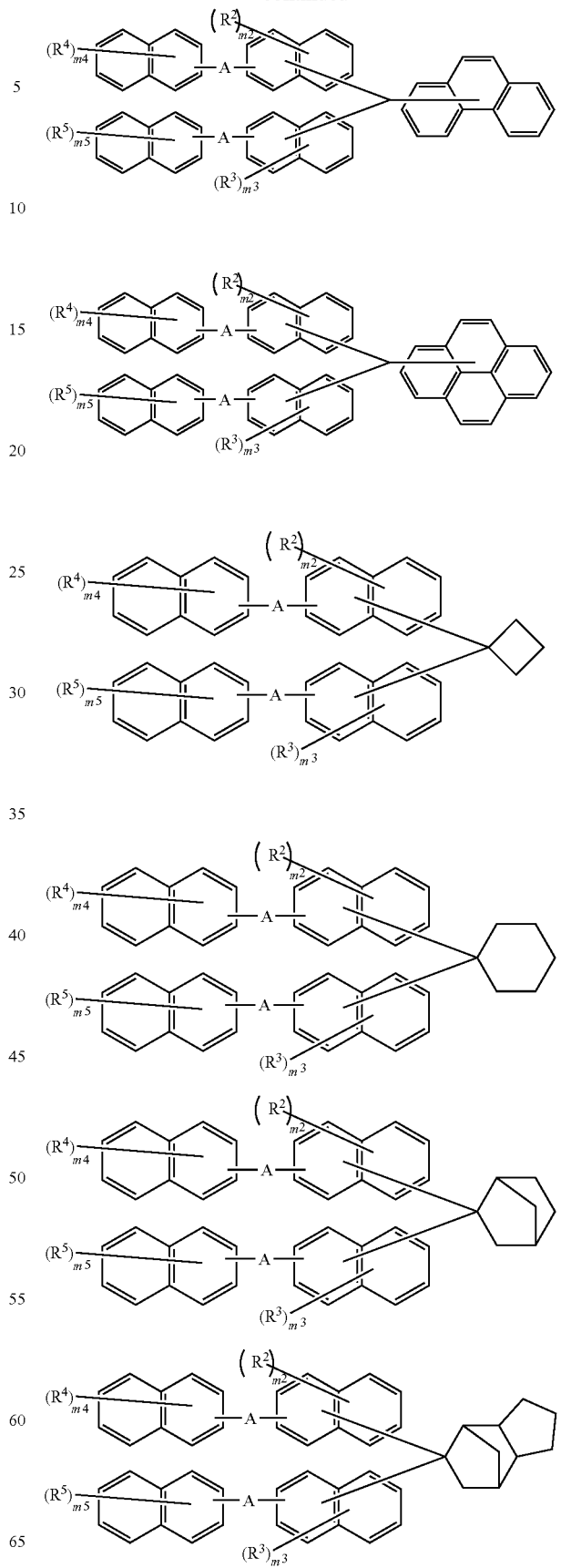

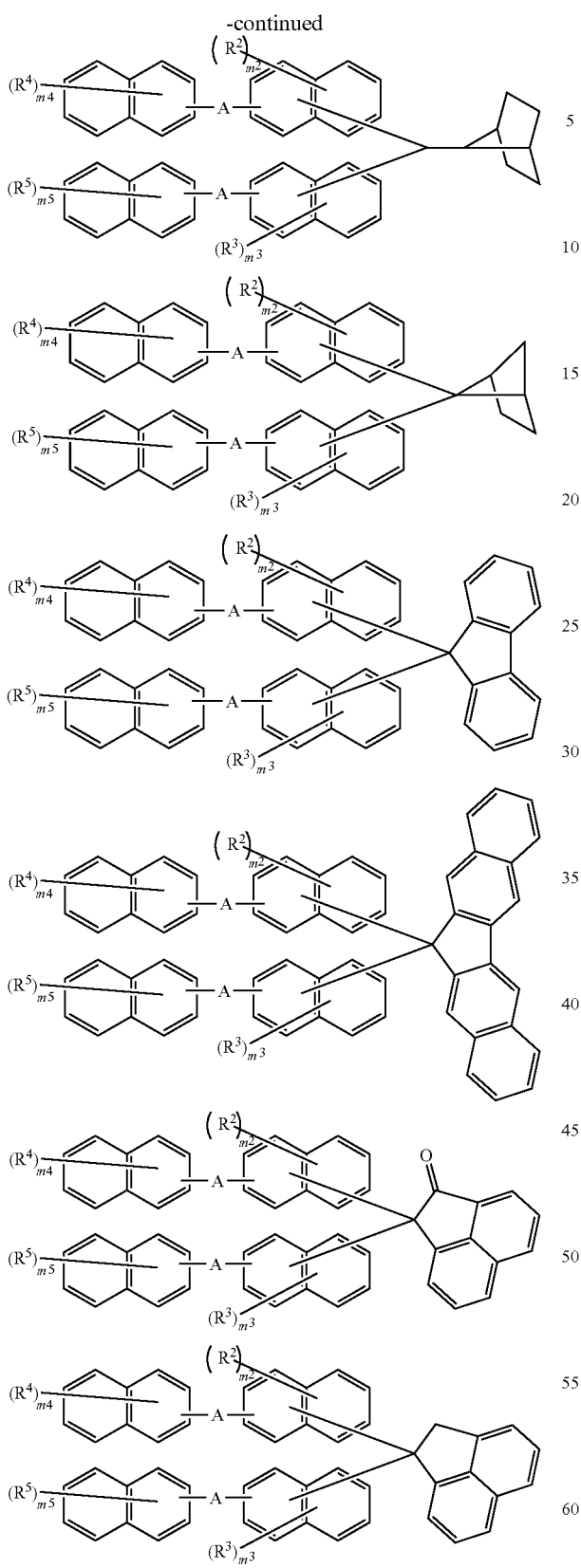
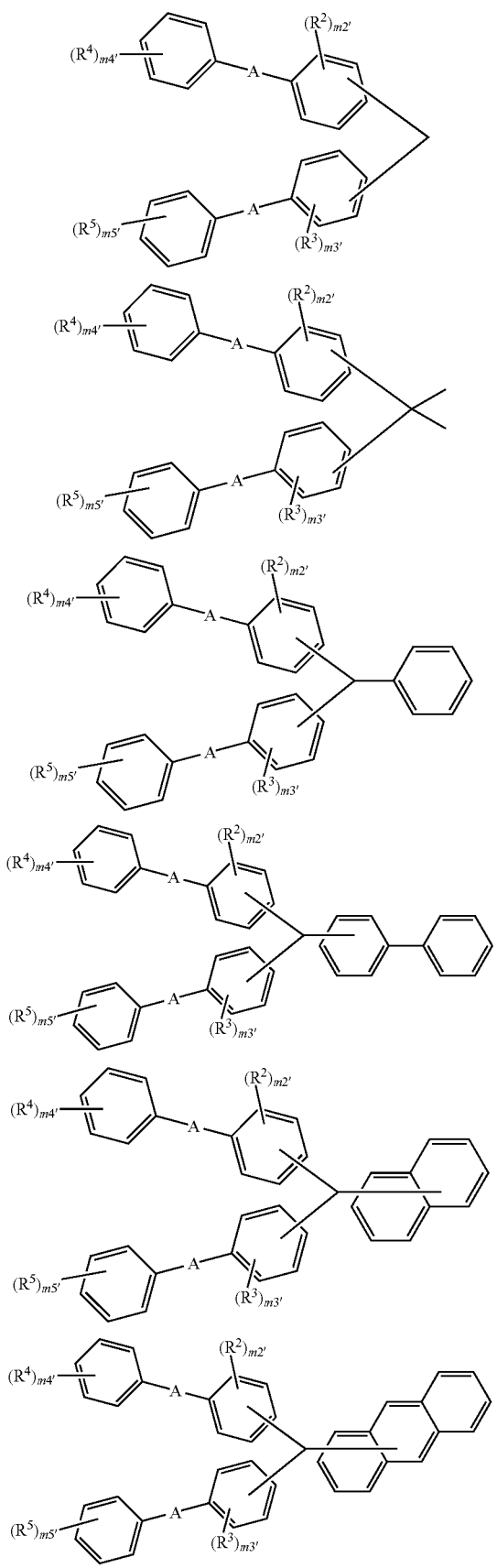
In each of the above formulas, A, $R^2$ to $R^5$, and $m^2$ to $m^5$ are as defined in A, $R^2$ to $R^5$, and $m^2$ to $m^5$ in the above formula (1), respectively.

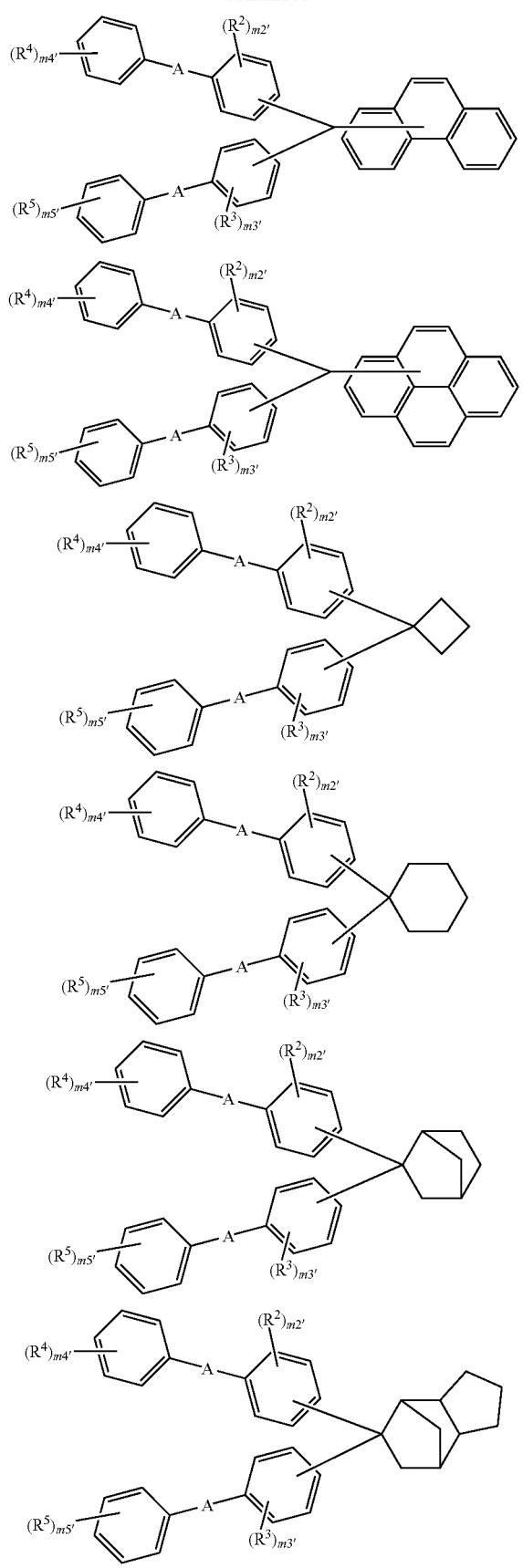
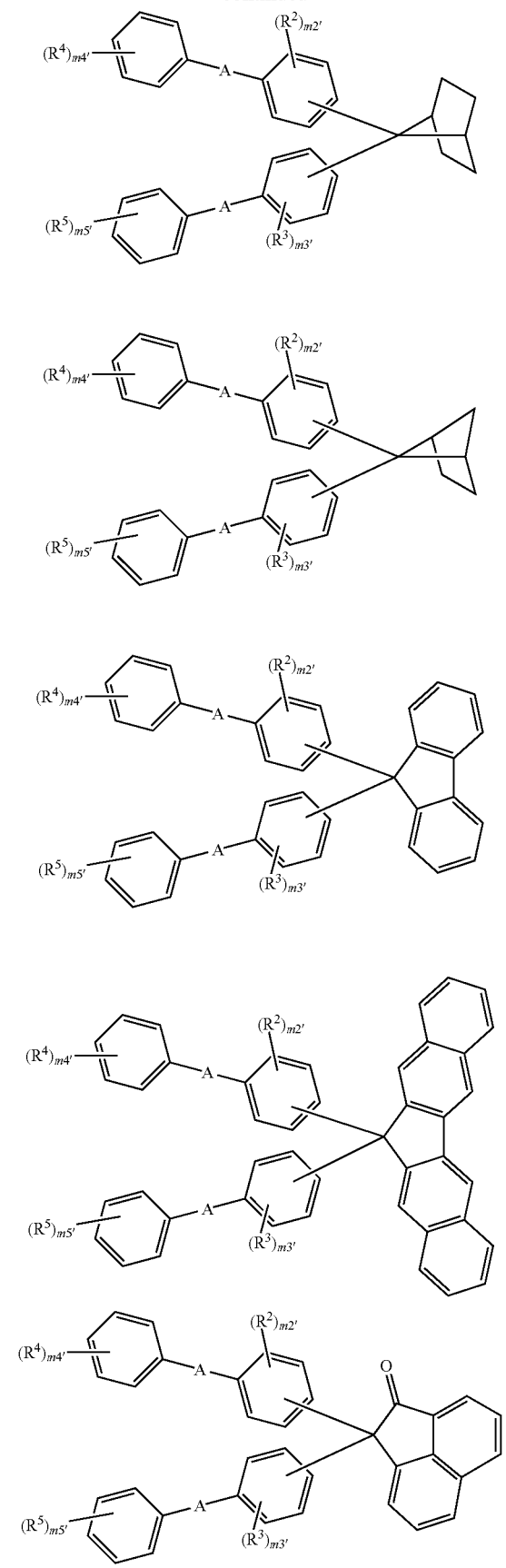

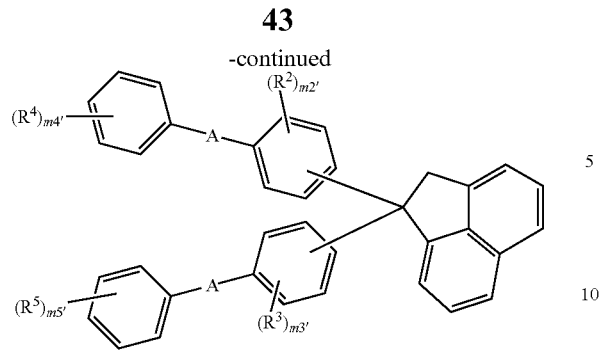
In each of the above formulas, A and $R^2$ to $R^5$ are as defined in A and $R^2$ to $R^5$ in the above formula (1), respectively. $m^{2\prime}$ and $m^{3\prime}$ are each independently an integer of 0 to 4, and $m^{4\prime}$ and $m^{5\prime}$ are each independently an integer of 0 to 5.
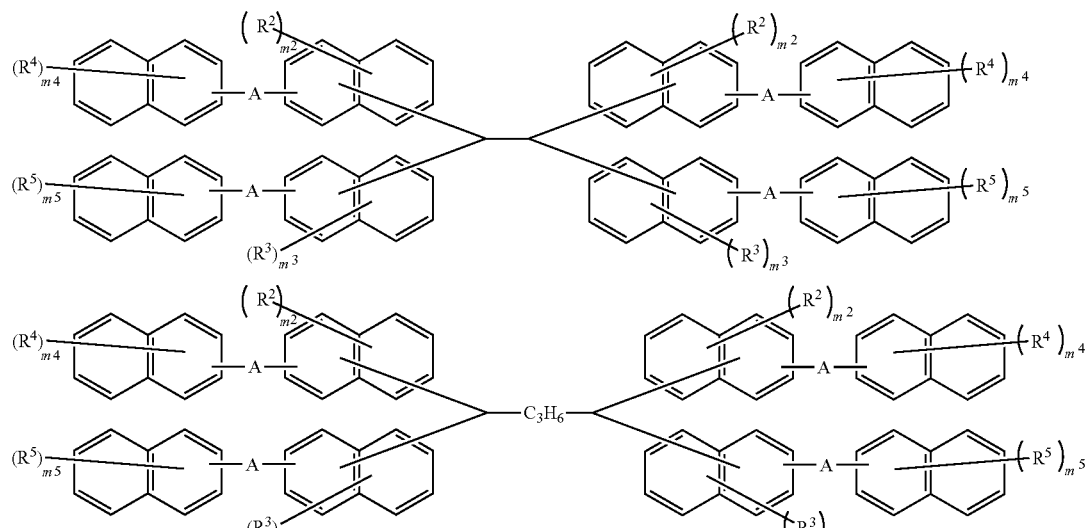
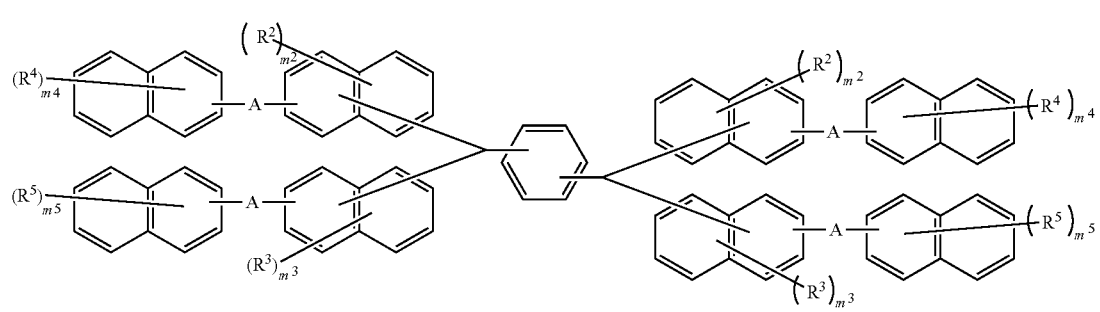
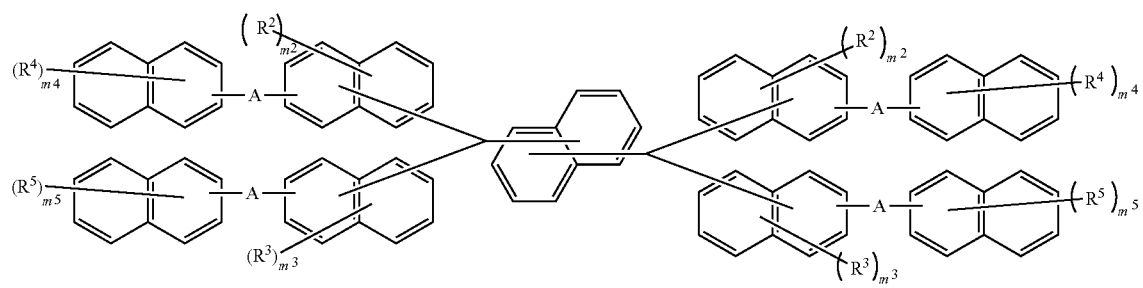

-continued
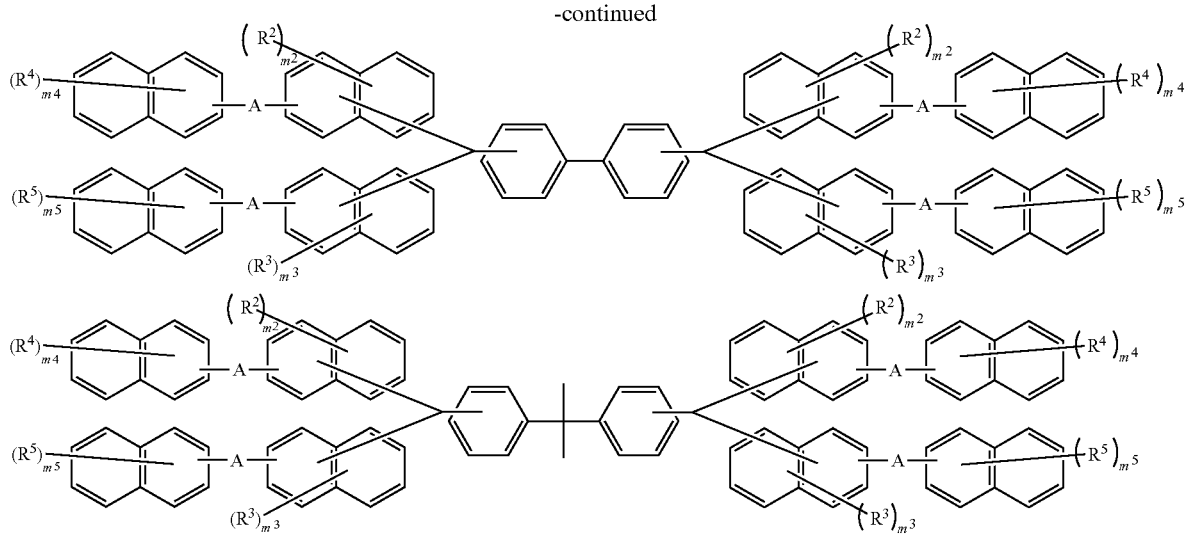
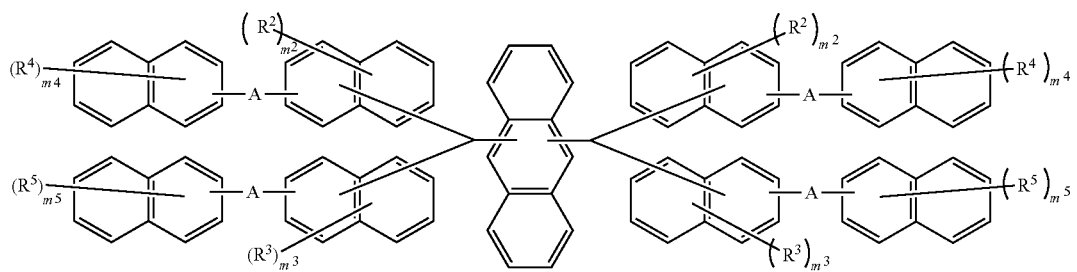
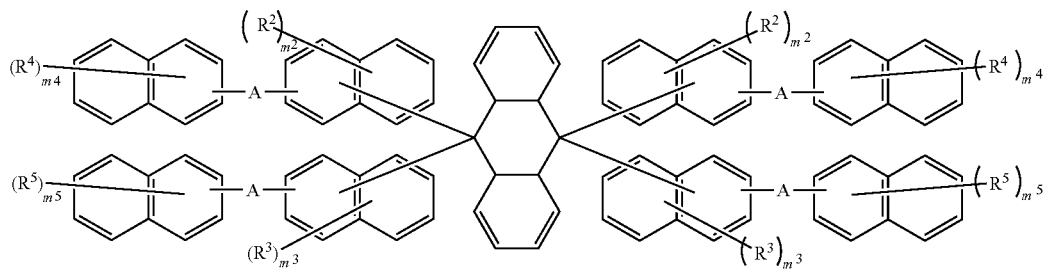
In the above formulas, A, $R^2$ to $R^5$, and $m^2$ to $m^5$ are as defined in A, $R^2$ to $R^5$, and $m^2$ to $m^5$ in the above formula (1), respectively.
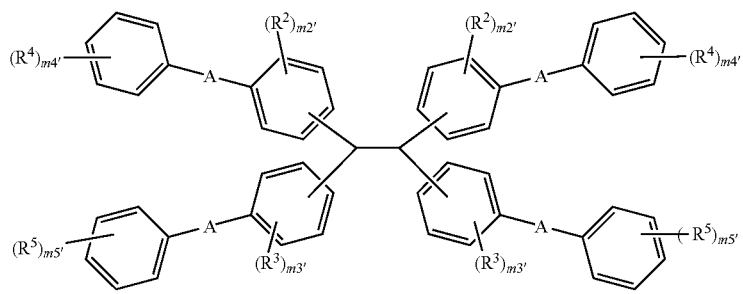

-continued
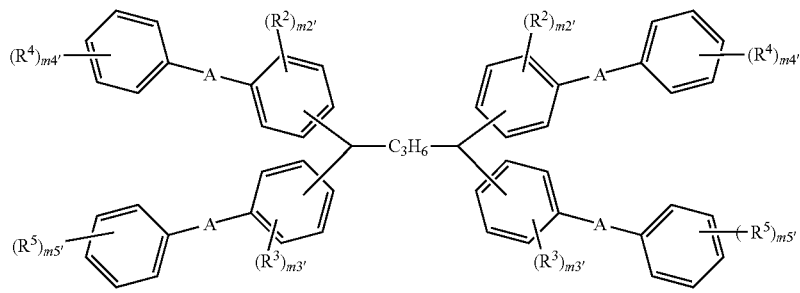
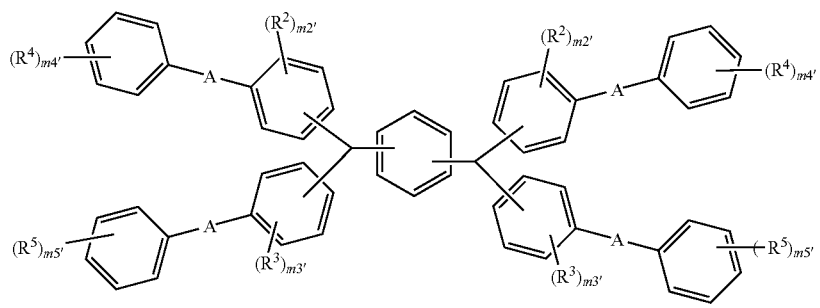
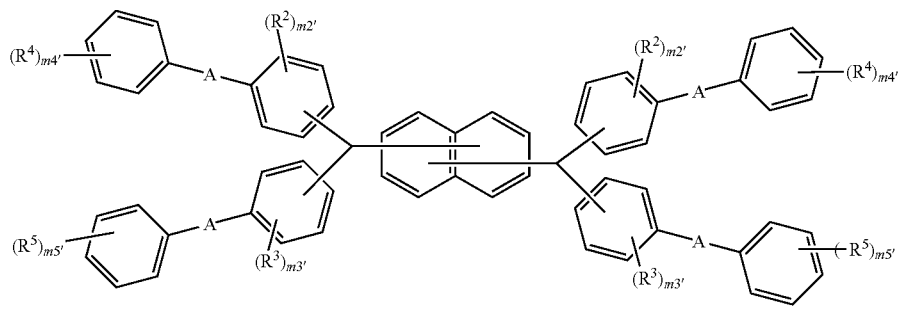
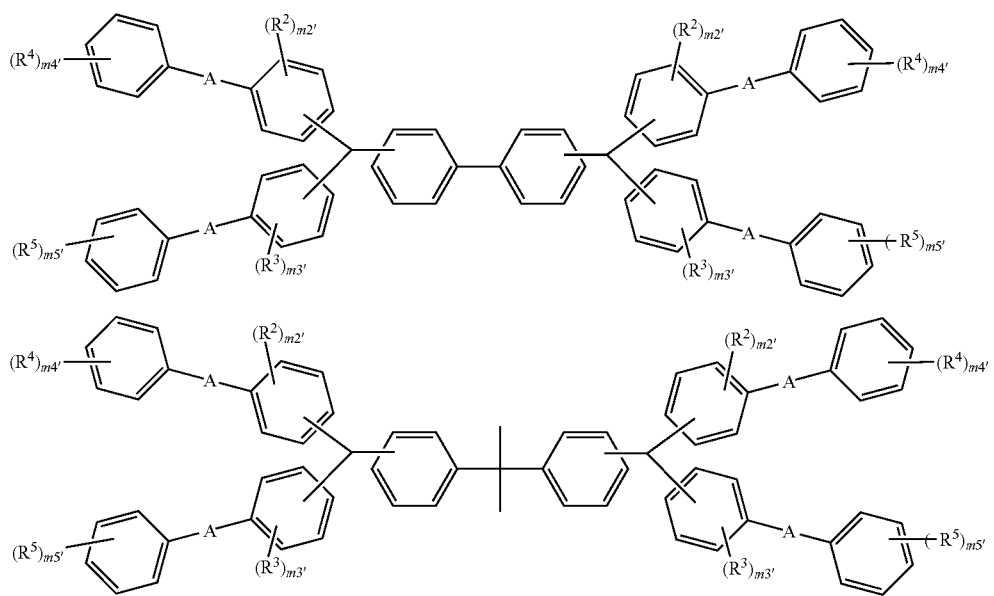

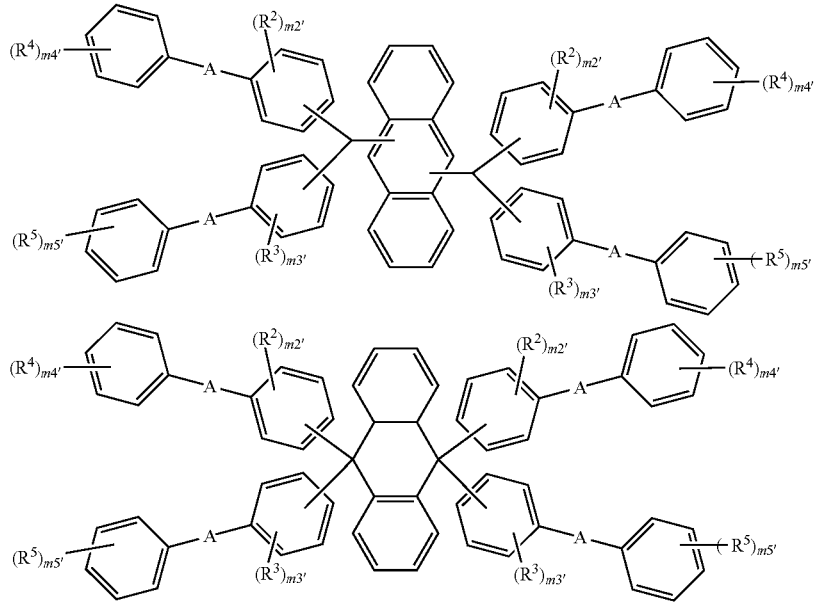
In each of the above formulas, A and $R^2$ to $R^5$ are as defined in A and $R^2$ to $R^5$ in the above formula (1), respectively. $m^{2\prime}$ and $m^{3\prime}$ are each independently an integer of 0 to 4, and $m^{4\prime}$ and $m^{5\prime}$ are each independently an integer of 0 to 5.
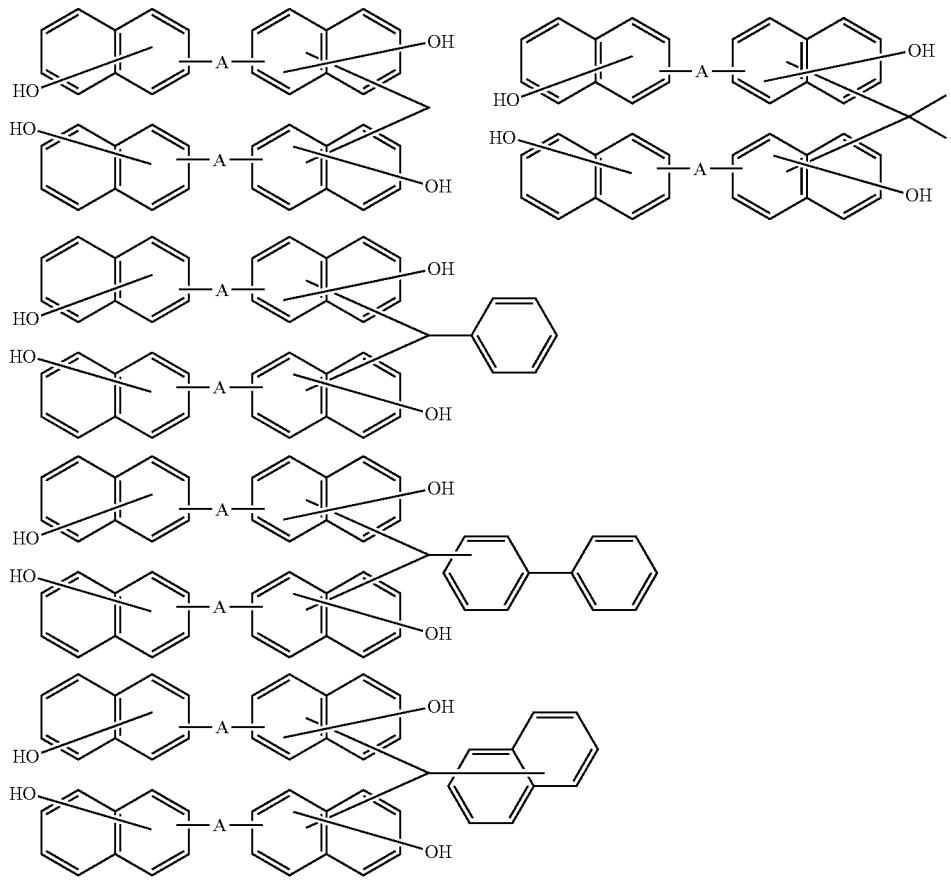

-continued
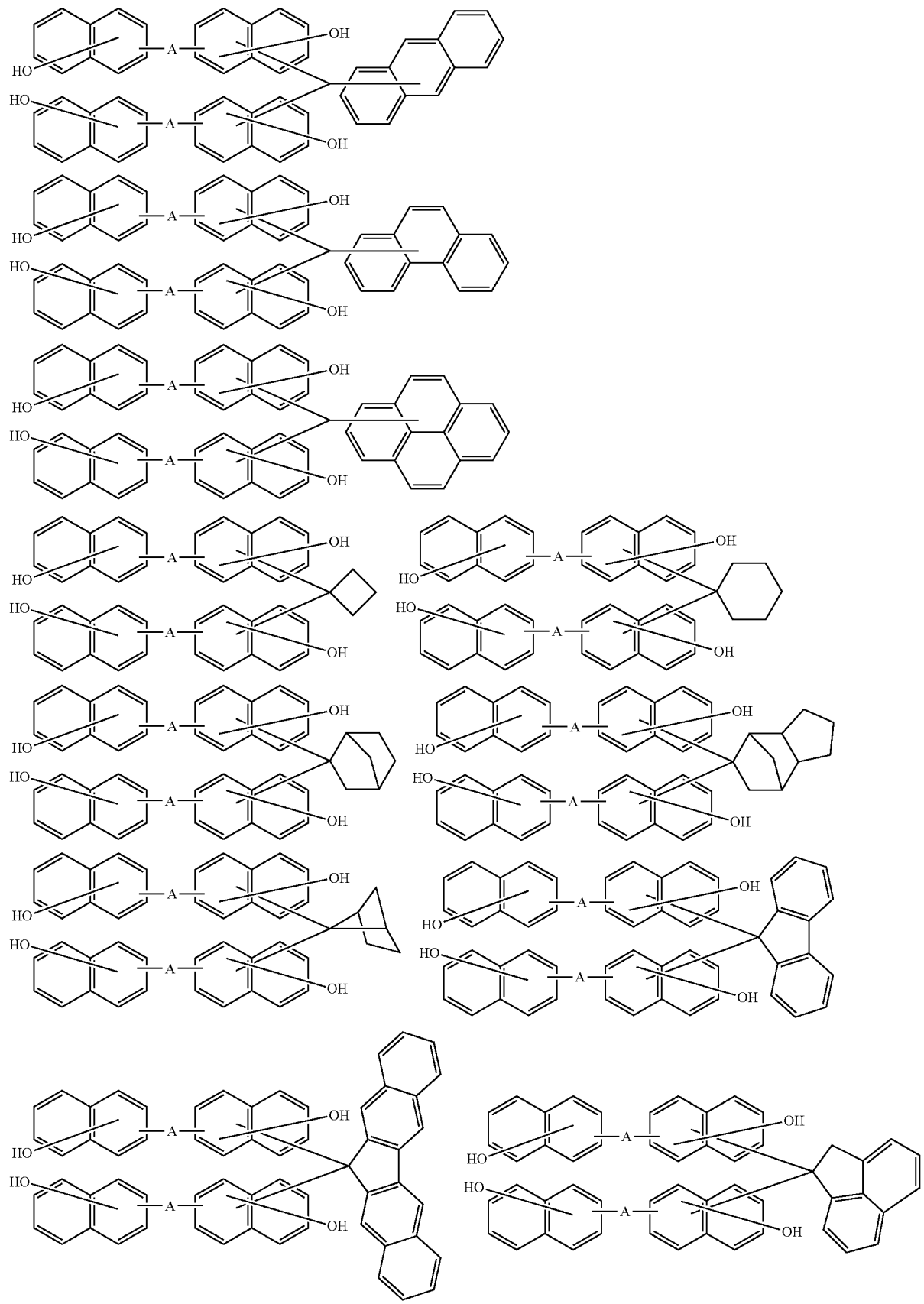

-continued
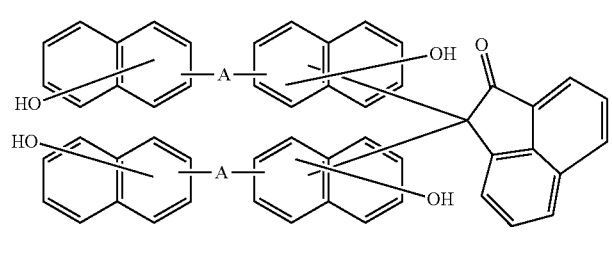
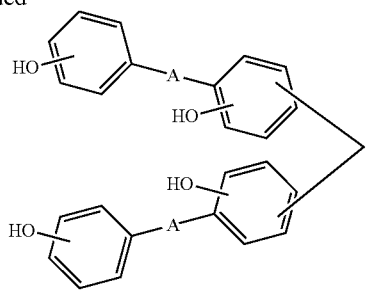
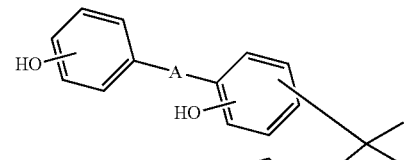
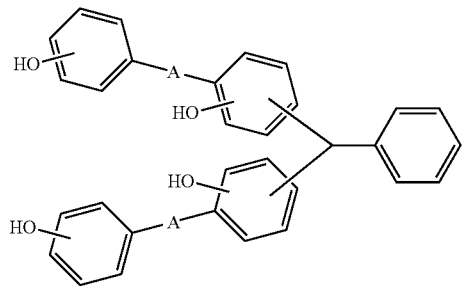
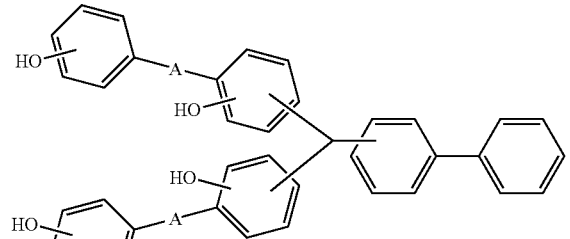
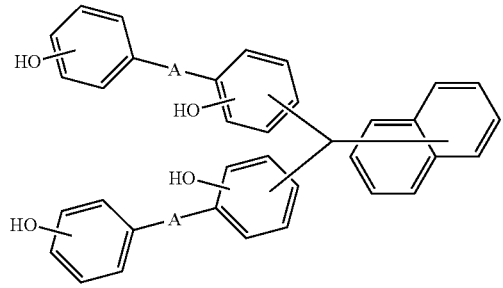
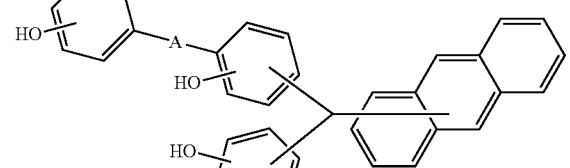
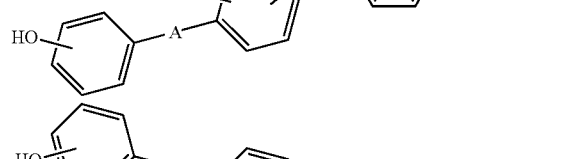
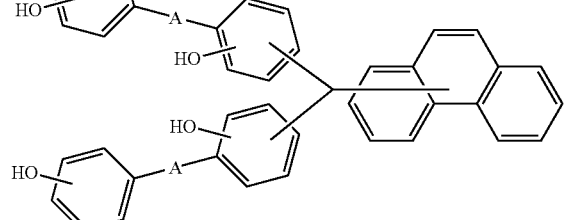
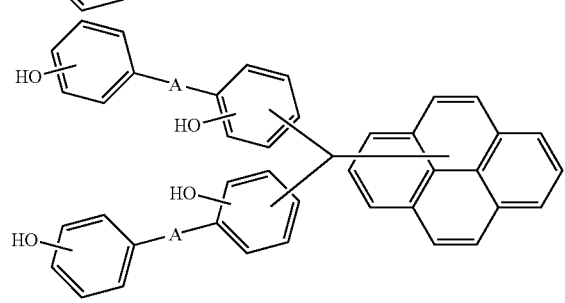
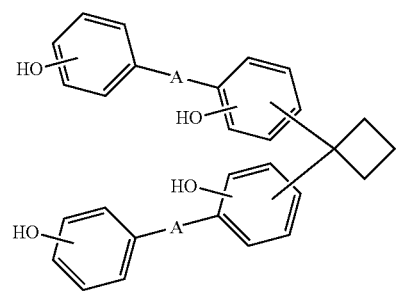

-continued
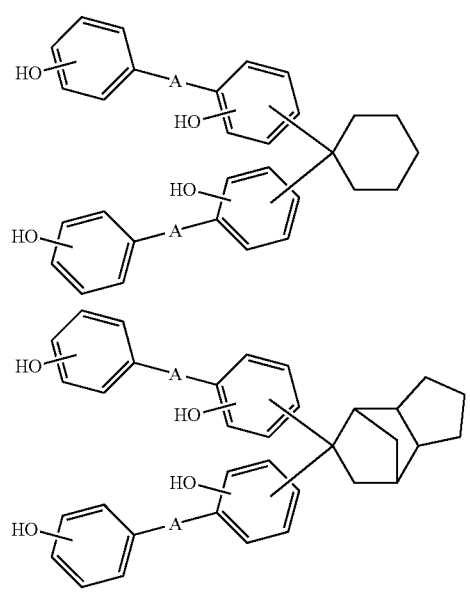
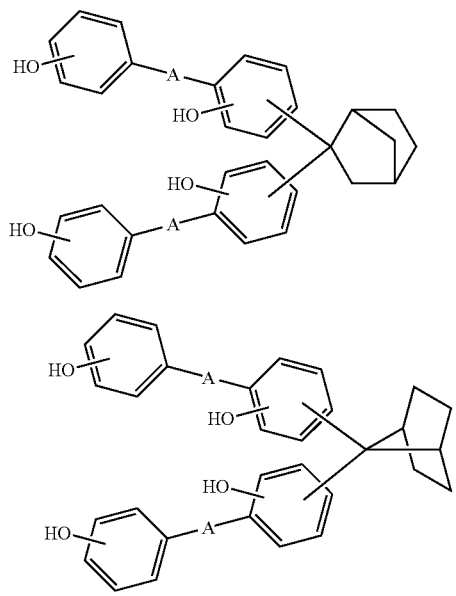
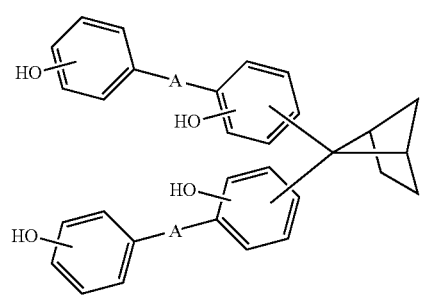
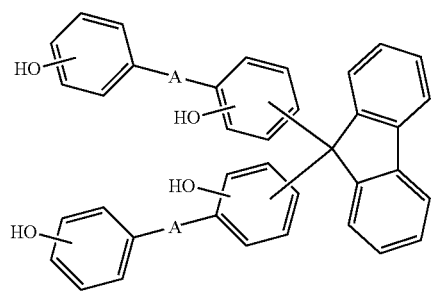
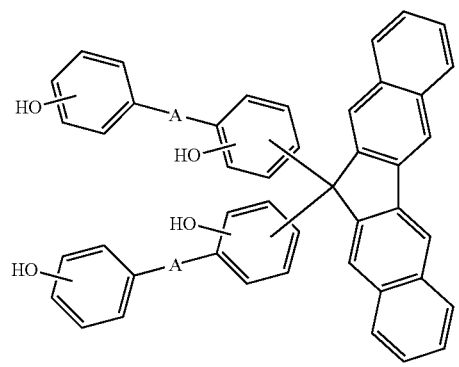
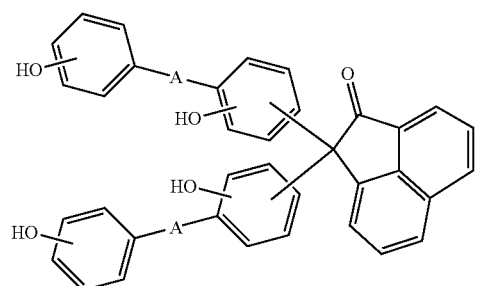
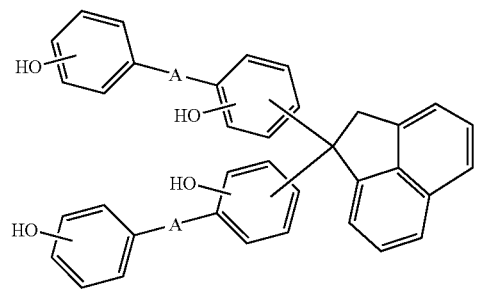

-continued
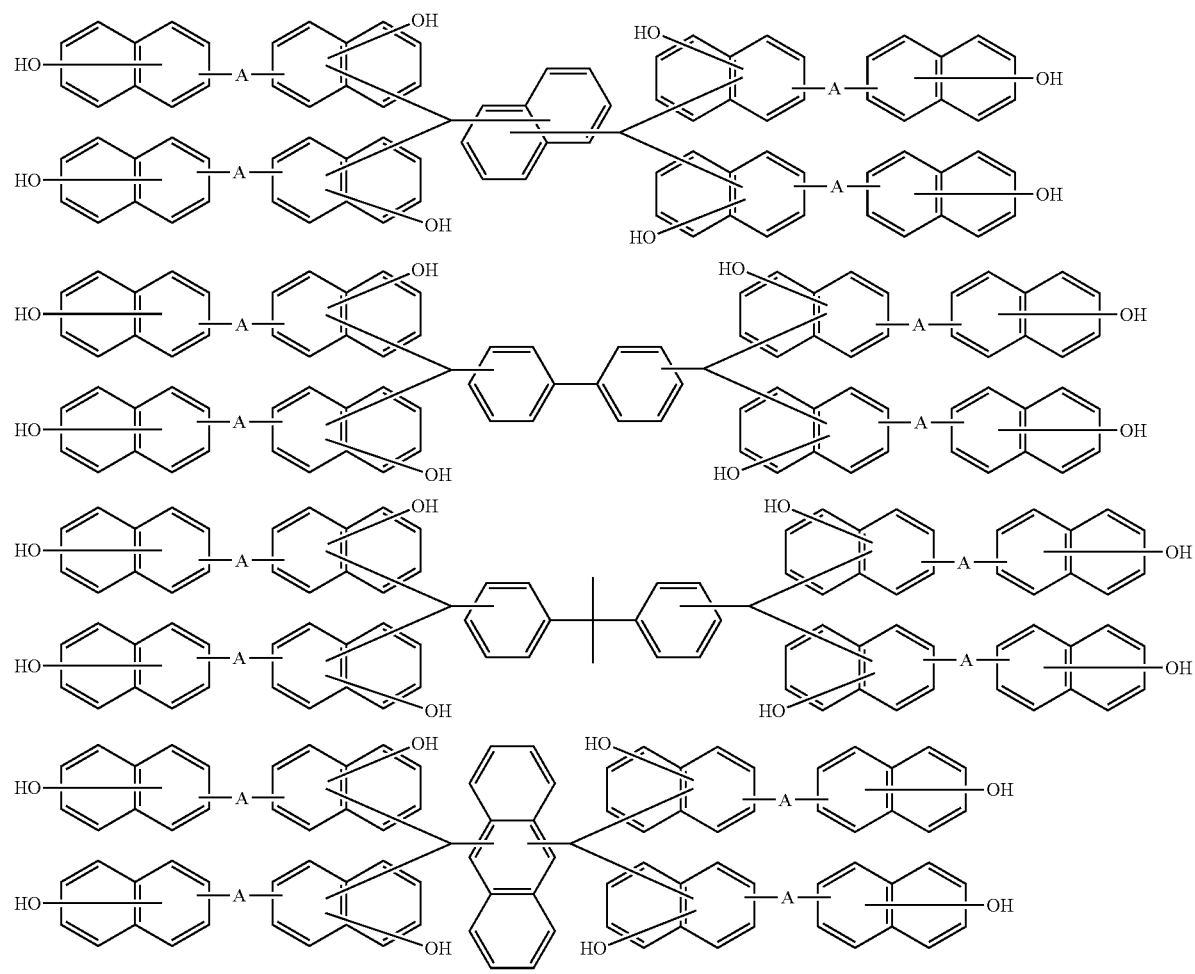

-continued
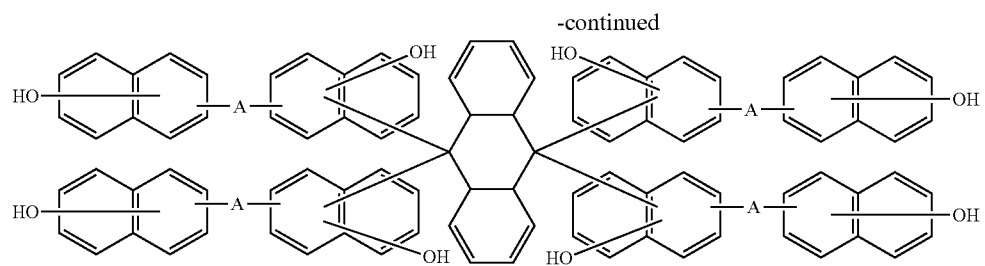
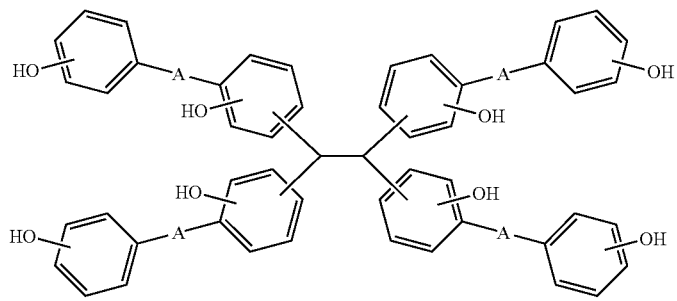
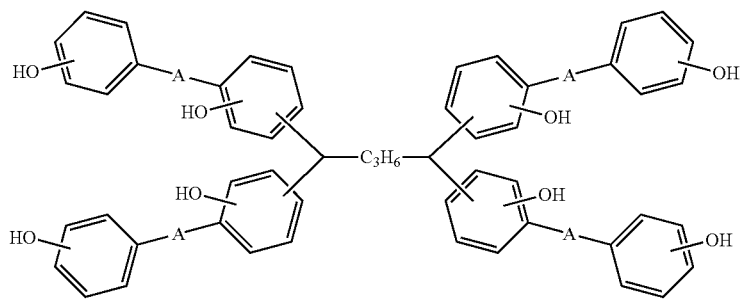
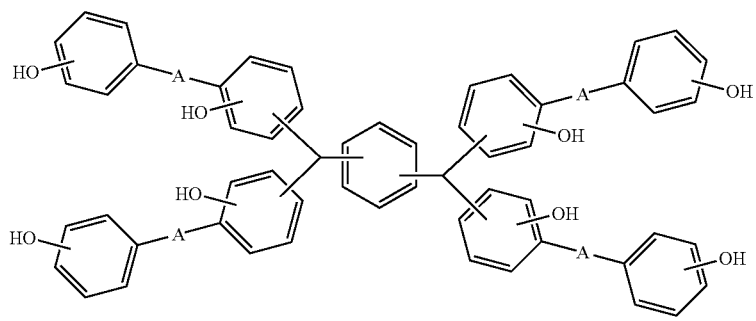
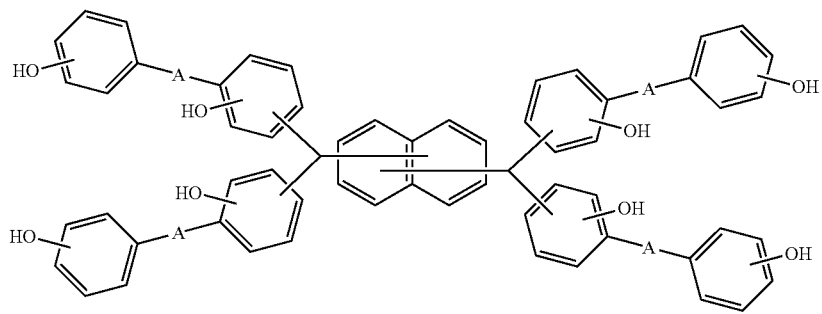

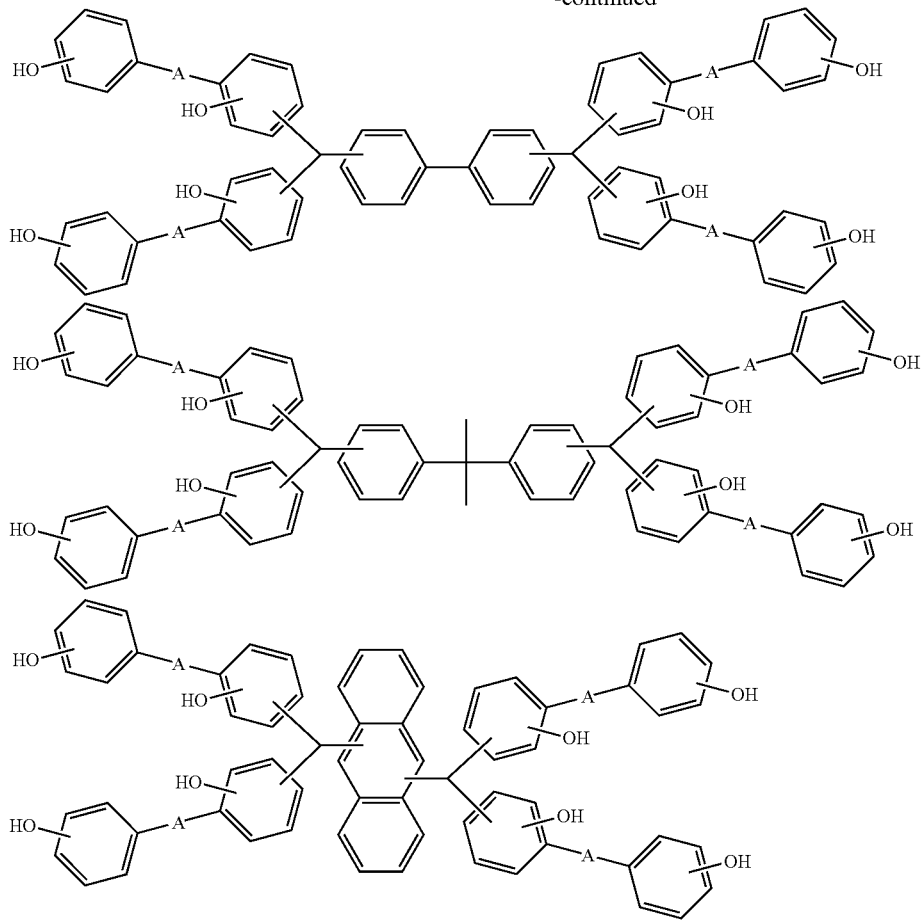

In each of the above formulas, A is as defined in A in the above formula (1).

Examples of the method for synthesizing the compound represented by the formula (1) include the following method. That is, the compound represented by the above formula (1) is obtained through a polycondensation reaction among the compound represented by the following formula (1-x), the compound represented by the following formula (1-y), and the compound represented by the following formula (z1) or the following formula (z2) in the presence of an acid catalyst or base catalyst at normal pressure. If necessary, the above reaction may be carried out under increased pressure.

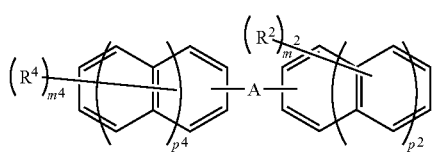

(1-x)

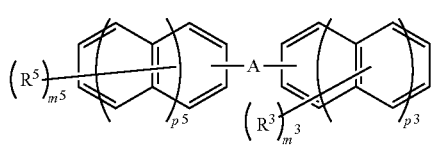

(1-y)

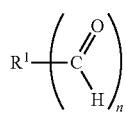

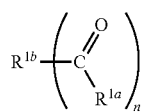

In the above formula (1-x), A, $R^2$, $R^4$, $m^2$, $m^4$, $p^2$ and $p^4$ are as defined in A, $R^2$, $R^4$, $m^2$, $m^4$, $p^2$ and $p^4$ in the formula (1), respectively; in the above formula (1-y), A, $R^3$, $R^5$, $m^3$, $m^5$, $p^3$ and $p^5$ are as defined in A, $R^3$, $R^5$, $m^3$, m, $p^3$ and $p^5$ in the formula (1), respectively; and the compound represented by the above formula (1-x) may be the same as the compound represented by the above formula (1-y).

In the above formula (z1), $R^1$ and n are as defined in $R^1$ and n in the above formula (1), respectively, and in the above formula (z2), $R^{1a}$, $R^{1b}$ and n are as defined in $R^{1a}$, $R^{1b}$ and n in the above formula (1), respectively.

As a specific example of the above polycondensation reaction, the compound represented by the above formula (1) is obtained through a polycondensation reaction between a dihydroxyphenyl ether, a dihydroxyphenyl thioether, a dihydroxynaphthyl ether, a dihydroxynthyl thioether, a dihydroxyanthracyl ether or a dihydroxyanthracyl thioether and a corresponding aldehyde or ketone in the presence of an acid catalyst or base catalyst.

Examples of the dihydroxyphenyl ether include, without particular limitations, dihydroxyphenyl ether, methyldihydroxyphenyl ether and methoxydihydroxyphenyl ether. These dihydroxyphenyl ethers are used alone as one kind or in combination of two or more kinds. Among them, it is preferable to use dihydroxyphenyl ether from the viewpoint of the stable supply of raw materials.

Examples of the dihydroxyphenyl thioether include, without particular limitations, dihydroxyphenyl thioether, methyldihydroxyphenyl thioether and methoxydihydroxyphenyl thioether. These dihydroxyphenyl thioethers are used alone as one kind or in combination of two or more kinds. Among them, it is preferable to use dihydroxyphenyl thioether from the viewpoint of the stable supply of raw materials.

Examples of the dihydroxynaphthyl ether include, without particular limitations, dihydroxynaphthyl ether, methyldihydroxynaphthyl ether and methoxydihydroxynaphthyl ether. These dihydroxynaphthyl ethers are used alone as one kind or in combination of two or more kinds. Among them, it is preferable to use dihydroxynaphthyl ether from the viewpoint of increasing a carbon atom concentration and improving heat resistance.

Examples of the dihydroxynaphthyl thioether include, without particular limitations, dihydroxynaphthyl thioether, methyldihydroxynaphthyl thioether and methoxydihydroxynaphthyl thioether. These dihydroxynaphthyl thioethers are used alone as one kind or in combination of two or more kinds. Among them, it is preferable to use dihydroxynaphthyl thioether from the viewpoint of increasing a carbon atom concentration and improving heat resistance.

Examples of the aldehyde include, without particular limitations, formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, dimethylbenzaldehyde, trimethylbenzaldehyde, ethylbenzaldehyde, propylbenzaldehyde, butylbenzaldehyde, pentabenzaldehyde, butylmethylbenzaldehyde, hydroxybenzaldehyde, dihydroxybenzaldehyde, fluoromethylbenzaldehyde, cyclopropylaldehyde, cyclobutylaldehyde, cyclohexylaldehyde, cyclodecylaldehyde, cycloundecylaldehyde, cyclopropylbenzaldehyde, cyclobutylbenzaldehyde, cyclohexylbenzaldehyde, cyclodecylbenzaldehyde, cycloundecylbenzaldehyde, biphenylaldehyde, naphthaldehyde, anthracenecarbaldehyde, phenanthrenecarbaldehyde, pyrenecarbaldehyde, and furfural. These aldehydes are used alone as one kind or in combination of two or more kinds. Among them, it is preferable to use one or more selected from the group consisting of benzaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, cyclohexylbenzaldehyde, biphenylaldehyde, naphthaldehyde, anthracenecarbaldehyde, phenanthrenecarbaldehyde, pyrenecarbaldehyde and furfural from the viewpoint that high heat resistance can be exhibited, and it is more preferable to use one or more selected from the group consisting of benzaldehyde, hydroxybenzaldehyde, chlorobenzaldehyde, nitrobenzaldehyde, methylbenzaldehyde, ethylbenzaldehyde, butylbenzaldehyde, cyclohexylbenzaldehyde, biphenylaldehyde, naphthaldehyde, anthracenecarbaldehyde, phenanthrenecarbaldehyde, pyrenecarbaldehyde and furfural from the viewpoint of improving etching resistance.

Examples of the ketone include, without particular limitations, acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, anthraquinone, acetophenone, diacetylbenzene, triacetylbenzene, acetonaphthone, acetylmethylbenzene, acetyldimethylbenzene, acetyltrimethylbenzene, acetylethylbenzene, acetylpropylbenzene, acetylbutylbenzene, acetylpentabenzene, acetylbutylmethylbenzene, acetylhydroxybenzene, acetyldihydroxybenzene, acetylfluoromethylbenzene, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl, and diphenylcarbonylbiphenyl. These ketones are used alone as one kind or in combination of two or more kinds. Among them, it is preferable to use one or more selected from the group consisting of cyclopentanone, cyclohexanone, norbornanone, tricyclohexanone, tricyclodecanone, adamantanone, fluorenone, benzofluorenone, acenaphthenequinone, acenaphthenone, anthraquinone, acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl and diphenylcarbonylbiphenyl from the viewpoint that high heat resistance can be exhibited, and it is more preferable to use one or more selected from the group consisting of acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl and diphenylcarbonylbiphenyl from the viewpoint of improving etching resistance.

As the aldehyde or the ketone, an aldehyde or a ketone having an aromatic ring is preferably used from the viewpoint that both high heat resistance and high etching resistance are achieved.

Examples of the acid catalyst to be used in the above reaction include, without particular limitations, an inorganic acid such as hydrochloric acid, sulfuric acid, phosphoric acid, hydrobromic acid, and hydrofluoric acid; an organic acid such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; a Lewis acid such as zinc chloride, aluminum chloride, iron chloride, and boron trifluoride; and a solid acid such as tungstosilicic acid, tungstophosphoric acid, silicomolybdic acid, and phosphomolybdic acid. These acid catalysts are used alone as one kind or in combination of two or more kinds. Among them, organic acids and solid acids are preferable from the viewpoint of production, and it is preferable to use hydrochloric acid or sulfuric acid from the viewpoint of production such as easy availability and handleability. The amount of the acid catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials.

Examples of the base catalyst to be used in the above reaction include, without particular limitations, a metal alkoxide (for example, an alkali metal or alkaline earth metal alkoxide such as sodium methoxide, sodium ethoxide, potassium methoxide and potassium ethoxide), a metal hydroxide (for example, an alkali metal or alkaline earth metal carbonate such as sodium hydroxide and potassium hydroxide), an alkali metal or alkaline earth bicarbonate such as sodium bicarbonate and potassium bicarbonate, and an organic base of an amine (for example, a tertiary amine (a trialkylamine such as triethylamine, an aromatic tertiary amine such as N,N-dimethylaniline, and a heterocyclic tertiary amine such as 1-methylimidazole), and a metal carboxylate (for example, an alkali metal or alkaline earth metal acetate such as sodium acetate and calcium acetate). These base catalysts are used alone as one kind or in combination of two or more kinds. Among them, metal alkoxides, metal hydroxides and amines are preferable from the viewpoint of production, and it is preferable to use sodium hydroxide from the viewpoint of production such as easy availability and handleability. The amount of the base catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials.

Upon the above reaction, a reaction solvent may be used. Examples of the reaction solvent include, without particular limitations, water, methanol, ethanol, propanol, butanol, tetrahydrofuran, dioxane, ethylene glycol dimethyl ether, and ethylene glycol diethyl ether. These solvents are used alone as one kind or in combination of two or more kinds.

The amount of the solvent used can be arbitrarily set according to, for example, the kind of the raw materials used and the catalyst used and moreover the reaction conditions and is not particularly limited, but is preferably in the range of 0 to 2000 parts by mass based on 100 parts by mass of the reaction raw materials. Furthermore, the reaction temperature in the above reaction can be arbitrarily selected according to the reactivity of the reaction raw materials and is not particularly limited, but is usually within the range of 10 to 200° C.

In order to obtain the compound represented by the formula (1) of the present embodiment, a higher reaction temperature is preferable. Specifically, the range of 60 to 200° C. is preferable. Although the reaction method is not particularly limited, for example, the raw materials (reactants) and the catalyst may be fed in a batch, or the raw materials (reactants) may be dripped successively in the presence of the catalyst. After the polycondensation reaction terminates, isolation of the obtained compound can be carried out according to a conventional method, and is not particularly limited. For example, by adopting a commonly used approach in which the temperature of the reaction vessel is elevated to 130 to 230° C. in order to remove unreacted raw materials, catalyst, etc. present in the system, and volatile portions are removed at about 1 to 50 mmHg, the compound that is the target compound can be obtained.

Examples of the preferable reaction conditions include conditions under which the reaction proceeds by using 1.0 mol to an excess of the compound represented by the above formula (1-x) and the compound represented by the above formula (1-y) based on 1 mol of the aldehyde or the ketone represented by the above formula (z1) or (z2), further using 0.001 to 1 mol of the acid catalyst, and reacting them at 50 to 150° C. at normal pressure for about 20 minutes to 100 hours.

The target compound can be isolated by a publicly known method after the reaction terminates. The compound represented by the above formula (1) which is the target compound can be obtained by, for example, concentrating the reaction liquid, precipitating the reaction product by the addition of pure water, cooling the reaction liquid to room temperature, then separating the precipitates by filtration, filtering and drying the obtained solid matter, then separating and purifying the solid matter from by-products by column chromatography, and distilling off the solvent, followed by filtration and drying.

[Resin]

The resin of the present embodiment is a resin obtained using the compound represented by the above formula (1) as a monomer. That is, the resin of the present embodiment contains the compound represented by the above formula (1) as a monomer component. Specific examples of the resin of the present embodiment include a resin having a structure represented by the formula (2).

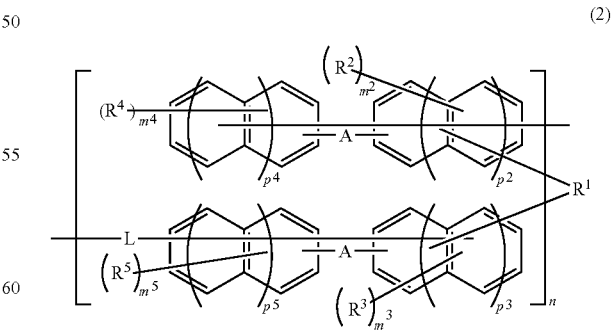

(2)

In the above formula (2), A, $R^1$ to $R^5$, $m^2$ to $m^5$, n, and $p^2$ to $p^5$ are as defined in A, $R^1$ to $R^5$, $m^2$ to m, n, and $p^2$ to $p^5$ in the above formula (1), respectively; and L is a single bond or a linking group.

Examples of the above linking group include a residue derived from the crosslinking compound, which will be mentioned later.

The resin of the present embodiment is obtained by reacting the compound represented by the above formula (1) with a crosslinking compound.

The crosslinking compound may be any compound as long as it can oligomerize or polymerize the compound represented by the above formula (1), and examples thereof include an aldehyde, a ketone, a carboxylic acid, a carboxylic acid halide, a halogen containing compound, an amino compound, an imino compound, an isocyanate compound, and an unsaturated hydrocarbon group containing compound.

Specific examples of the resin of the present embodiment include a resin that has been made novolac obtained through, for example, a condensation reaction between the compound represented by the above formula (1) and an aldehyde or ketone, which is a crosslinking compound.

Here, examples of the aldehyde to be used upon making the compound represented by the above formula (1) novolac include, without particular limitations, formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural. These aldehydes are used alone as one kind or in combination of two or more kinds. Among them, it is preferable to use one or more selected from the group consisting of benzaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, cyclohexylbenzaldehyde, biphenylaldehyde, naphthaldehyde, anthracenecarbaldehyde, phenanthrenecarbaldehyde, pyrenecarbaldehyde and furfural from the viewpoint that high heat resistance can be exhibited; it is preferable to use one or more selected from the group consisting of benzaldehyde, hydroxybenzaldehyde, chlorobenzaldehyde, nitrobenzaldehyde, methylbenzaldehyde, ethylbenzaldehyde, butylbenzaldehyde, cyclohexylbenzaldehyde, biphenylaldehyde, naphthaldehyde, anthracenecarbaldehyde, phenanthrenecarbaldehyde, pyrenecarbaldehyde and furfural from the viewpoint of improving etching resistance; and it is more preferable to use formaldehyde. The amount of the aldehyde used is not particularly limited, but is preferably 0.2 to 5 mol and more preferably 0.5 to 2 mol based on 1 mol of the compound represented by the above formula (1).

Examples of the ketone to be used upon making the compound represented by the above formula (1) novolac include, without particular limitations, acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, anthraquinone, acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl, and diphenylcarbonylbiphenyl. These ketones are used alone as one kind or in combination of two or more kinds. Among them, it is preferable to use one or more selected from the group consisting of cyclopentanone, cyclohexanone, norbornanone, tricyclohexanone, tricyclodecanone, adamantanone, fluorenone, benzofluorenone, acenaphthenequinone, acenaphthenone, anthraquinone, acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl and diphenylcarbonylbiphenyl from the viewpoint that high heat resistance can be exhibited, and it is more preferable to use one or more selected from the group consisting of acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl and diphenylcarbonylbiphenyl from the viewpoint of improving etching resistance. The amount of the ketone used is not particularly limited, but is preferably 0.2 to 5 mol and more preferably 0.5 to 2 mol based on 1 mol of the compound represented by the above formula (1).

A catalyst can also be used in the condensation reaction between the compound represented by the above formula (1) and the aldehyde or ketone. The acid catalyst or base catalyst to be used herein can be arbitrarily selected for use from publicly known catalysts and is not particularly limited. Examples of such an acid catalyst include, without particular limitations, an inorganic acid such as hydrochloric acid, sulfuric acid, phosphoric acid, hydrobromic acid, and hydrofluoric acid; an organic acid such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; a Lewis acid such as zinc chloride, aluminum chloride, iron chloride, and boron trifluoride; and a solid acid such as tungstosilicic acid, tungstophosphoric acid, silicomolybdic acid, and phosphomolybdic acid. These catalysts are used alone as one kind or in combination of two or more kinds. Among them, organic acids and solid acids are preferable from the viewpoint of production, and hydrochloric acid or sulfuric acid is preferable from the viewpoint of production such as easy availability and handleability. The amount of the acid catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials.

However, in the case of a copolymerization reaction with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborn-2-ene, α-pinene, β-pinene and limonene, the aldehyde or ketone is not necessarily needed.

A reaction solvent can also be used in the condensation reaction between the compound represented by the above formula (1) and the aldehyde or ketone. The reaction solvent in the polycondensation can be arbitrarily selected for use from publicly known solvents and is not particularly limited, and examples thereof include water, methanol, ethanol, propanol, butanol, tetrahydrofuran, dioxane, and a mixed solvent thereof. These solvents are used alone as one kind or in combination of two or more kinds.

The amount of the solvent used can be arbitrarily set according to, for example, the kind of the raw materials used and the catalyst used and moreover the reaction conditions and is not particularly limited, but is preferably in the range of 0 to 2000 parts by mass based on 100 parts by mass of the reaction raw materials. Furthermore, the reaction temperature can be arbitrarily selected according to the reactivity of the reaction raw materials and is not particularly limited, but is usually within the range of 10 to 200° C. Examples of the reaction method include a method in which the compound represented by the above formula (1), the aldehyde and/or ketone, and the catalyst are fed in a batch, or a method in which the compound represented by the above formula (1) and the aldehyde and/or ketone are dripped successively in the presence of the catalyst.

After the polycondensation reaction terminates, isolation of the obtained compound can be carried out according to a conventional method, and is not particularly limited. For example, by adopting a commonly used approach in which the temperature of the reaction vessel is elevated to 130 to 230° C. in order to remove unreacted raw materials, catalyst, etc. present in the system, and volatile portions are removed at about 1 to 50 mmHg, the target compound (for example, the resin that has been made novolac) can be obtained.

The resin of the present embodiment is also obtained upon the synthesis reaction of the compound represented by the above formula (1). This corresponds to the case where the same aldehyde or ketone is used upon polymerizing the compound represented by the above formula (1) as that used in the synthesis of the compound of the above formula (1).

Here, the resin of the present embodiment may be a homopolymer of the compound represented by the above formula (1), or may be a copolymer with a further phenol. Here, examples of the copolymerizable phenol include, without particular limitations, phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol.

In addition, the resin of the present embodiment may be a copolymer with a polymerizable monomer other than the further phenol mentioned above. Examples of the copolymerization monomer include, without particular limitations, naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornene, pinene, and limonene. The resin of the present embodiment may be a copolymer of two or more components (for example, a binary to quaternary system) composed of the compound represented by the above formula (1) and the above phenol, may be a copolymer of two or more components (for example, a binary to quaternary system) composed of the compound represented by the above formula (1) and the above copolymerization monomer, or may be a copolymer of three or more components (for example, a tertiary to quaternary system) composed of the compound represented by the above formula (1), the above phenol, and the above copolymerization monomer.

The weight average molecular weight (Mw) of the resin of the present embodiment is not particularly limited, and is, in terms of polystyrene through GPC measurement, preferably 500 to 30,000 and more preferably 750 to 20,000. In addition, the resin of the present embodiment preferably has dispersibility (weight average molecular weight Mw/number average molecular weight Mn) within the range of 1.2 to 7 from the viewpoint of enhancing crosslinking efficiency while suppressing volatile components during baking.

It is preferable that the compound represented by the above formula (1) and/or the resin obtained using the compound represented by the formula (1) as a monomer have high solubility in a solvent from the viewpoint of easier application to a wet process, etc. More specifically, in the case of using 1-methoxy-2-propanol (PGME) and/or propylene glycol monomethyl ether acetate (PGMEA) as a solvent, it is preferable that the compound and/or resin have a solubility of 10% by mass or more in the solvent. Here, the solubility in PGME and/or PGMEA is defined as "mass of the resin/(mass of the resin+mass of the solvent)×100 (% by mass)". For example, 10 g of the compound represented by the above formula (1) and/or the resin obtained using the compound as a monomer is evaluated as being dissolved in 90 g of PGMEA when the solubility of the compound represented by the formula (1) and/or the resin obtained using the compound as a monomer in PGMEA is "10% by mass or more"; and 10 g of the compound and/or the resin is evaluated as being not dissolved in 90 g of PGMEA when the solubility is "less than 10% by mass".

[Composition]

The composition of the present embodiment contains one or more selected from the group consisting of the compound represented by the formula (1) and the resin obtained using the compound represented by the formula (1) as a monomer.

The composition of the present embodiment contains the compound and/or the resin of the present embodiment, and is thus applicable to a wet process and is useful as a composition for forming a film for lithography that is excellent in heat resistance and etching resistance (that is, a "film forming composition for lithography"). The composition of the present embodiment contains the compound or the resin with a specific structure having high heat resistance and solvent solubility, and can therefore form a film for lithography that is prevented from being deteriorated upon baking at a high temperature and is excellent in etching resistance against plasma etching or the like, compared to a photoresist layer. Furthermore, when an underlayer film is formed, the composition of the present embodiment is also excellent in adhesiveness to a resist layer and can therefore form an excellent resist pattern. In addition, the composition of the present embodiment has high refractive index ascribable to its high aromatic ring density and is also prevented from being stained by heat treatment in a wide range from a low temperature to a high temperature. Therefore, the composition of the present embodiment is also used suitably in optical component formation.

As used herein, a film forming composition for lithography used to form a photoresist layer may be referred to as a "resist composition". Also, a film forming composition for lithography used to form a resist underlayer film may be referred to as an "underlayer film forming composition for lithography".

[Film Forming Composition for Lithography]

The film forming composition for lithography according to the present embodiment can be suitably used as a resist composition, an underlayer film forming composition for lithography, and a resist permanent film forming composition.

[Resist Composition]

The resist composition of the present embodiment contains one or more components (hereinafter, may also be referred to as a "component (A)") selected from the group consisting of the compound represented by the above formula (1) and the resin obtained using such a compound as a monomer.

It is preferable that the resist composition of the present embodiment should contain a solvent. Examples of the solvent can include, but not particularly limited to, an ethylene glycol monoalkyl ether acetate such as ethylene glycol monomethyl ether acetate, ethylene glycol monoethyl ether acetate, ethylene glycol mono-n-propyl ether acetate, and ethylene glycol mono-n-butyl ether acetate; an ethylene glycol monoalkyl ether such as ethylene glycol monomethyl ether and ethylene glycol monoethyl ether; a propylene glycol monoalkyl ether acetate such as propylene glycol monomethyl ether acetate (PGMEA), propylene glycol monoethyl ether acetate, propylene glycol mono-n-propyl ether acetate, and propylene glycol mono-n-butyl ether acetate; a propylene glycol monoalkyl ethers such as propylene glycol monomethyl ether (PGME) and propylene glycol monoethyl ether; a lactate ester such as methyl lactate, ethyl lactate, n-propyl lactate, n-butyl lactate, and n-amyl lactate; an aliphatic carboxylic acid ester such as methyl acetate, ethyl acetate, n-propyl acetate, n-butyl acetate, n-amyl acetate, n-hexyl acetate, methyl propionate, and ethyl propionate; another ester such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutyl acetate, 3-methyl-3-methoxybutyl acetate, butyl 3-methoxy-3-methylpropionate, butyl 3-methoxy-3-methylbutyrate, methyl acetoacetate, methyl pyruvate, and ethyl pyruvate; an aromatic hydrocarbon such as toluene and xylene; a ketone such as 2-heptanone, 3-heptanone, 4-heptanone, cyclopentanone (CPN), and cyclohexanone (CHN); an amide such as N,N-dimethylformamide, N-methylacetamide, N,N-dimethylacetamide, and N-methylpyrrolidone; and a lactone such as γ-lactone. These solvents can be used alone or in combination of two or more kinds.

The solvent used in the present embodiment is preferably a safe solvent, more preferably at least one selected from PGMEA, PGME, CHN, CPN, 2-heptanone, anisole, butyl acetate, ethyl propionate, and ethyl lactate, and still more preferably at least one selected from PGMEA, PGME, and CHN.

In the present embodiment, the amount of the solid components and the amount of the solvent are not particularly limited, but preferably the solid components are 1 to 80% by mass and the solvent is 20 to 99% by mass, more preferably the solid components are 1 to 50% by mass and the solvent is 50 to 99% by mass, still more preferably the solid components are 2 to 40% by mass and the solvent is 60 to 98% by mass, and particularly preferably the solid components are 2 to 10% by mass and the solvent is 90 to 98% by mass, based on 100% by mass of the total mass of the amount of the solid components and the solvent.

[Other Components]

The resist composition of the present embodiment may contain other components, such as an acid generating agent and a crosslinking agent, in addition to the component (A) and the solvent mentioned above, if required. Hereinafter, these optional components will be described.

[Acid Generating Agent (C)]

The resist composition of the present embodiment preferably contains one or more acid generating agents (C) generating an acid directly or indirectly by irradiation of any radiation selected from visible light, ultraviolet, excimer laser, electron beam, extreme ultraviolet (EUV), X-ray, and ion beam. The acid generating agent (C) is not particularly limited, and, for example, an acid generating agent described in International Publication No. WO 2013/024778 can be used. The acid generating agent (C) can be used alone or in combination of two or more kinds.

The amount of the acid generating agent (C) used is preferably 0.001 to 49% by mass of the total weight of the solid components, more preferably 1 to 40% by mass, still more preferably 3 to 30% by mass, and particularly preferably 10 to 25% by mass. By using the acid generating agent (C) within the above range, a pattern profile with high sensitivity and low edge roughness is obtained. In the present embodiment, the acid generation method is not limited as long as an acid is generated in the system. By using excimer laser instead of ultraviolet such as g-ray and i-ray, finer processing is possible, and also by using electron beam, extreme ultraviolet, X-ray or ion beam as a high energy ray, further finer processing is possible.

[Acid Crosslinking Agent (G)]

In the present embodiment, the resist composition preferably contains one or more acid crosslinking agents (G). The acid crosslinking agent (G) is a compound capable of intramolecularly or intermolecularly crosslinking the component (A) in the presence of the acid generated from the acid generating agent (C). Examples of such an acid crosslinking agent (G) can include a compound having one or more groups (hereinafter, referred to as a "crosslinkable group") capable of crosslinking the component (A).

Examples of such a crosslinkable group can include, but not particularly limited to, (i) a hydroxyalkyl group such as a hydroxy (C1-C6 alkyl group), a C1-C6 alkoxy (C1-C6 alkyl group), and an acetoxy (C1-C6 alkyl group), or a group derived therefrom; (ii) a carbonyl group such as a formyl group and a carboxy (C1-C6 alkyl group), or a group derived therefrom; (iii) a nitrogenous group-containing group such as a dimethylaminomethyl group, a diethylaminomethyl group, a dimethylolaminomethyl group, a diethylolaminomethyl group, and a morpholinomethyl group; (iv) a glycidyl group-containing group such as a glycidyl ether group, a glycidyl ester group, and a glycidylamino group; (v) a group derived from an aromatic group such as a C1-C6 allyloxy (C1-C6 alkyl group) and a C1-C6 aralkyloxy (C1-C6 alkyl group) such as a benzyloxymethyl group and a benzoyloxymethyl group; and (vi) a polymerizable multiple bond-containing group such as a vinyl group and an isopropenyl group. As the crosslinkable group of the acid crosslinking agent (G) according to the present embodiment, a hydroxyalkyl group and an alkoxyalkyl group or the like are preferable, and an alkoxymethyl group is particularly preferable.

The acid crosslinking agent (G) having the above crosslinkable group is not particularly limited, and, for example, an acid crosslinking agent described in International Publication No. WO 2013/024778 can be used. The acid crosslinking agent (G) can be used alone or in combination of two or more kinds.

In the present embodiment, the amount of the acid crosslinking agent (G) used is preferably 0.5 to 49% by mass of the total weight of the solid components, more preferably 0.5 to 40% by mass, still more preferably 1 to 30% by mass, and particularly preferably 2 to 20% by mass. When the amount of the above acid crosslinking agent (G) used is 0.5% by mass or more, there is a tendency that the inhibiting effect of the solubility of a resist film in an alkaline developing solution is improved and that a decrease in the film remaining rate, as well as occurrence of swelling and meandering of a pattern, can be inhibited. On the other hand, when the amount is 49% by mass or less, there is a tendency that a decrease in heat resistance as a resist can be inhibited.

[Acid Diffusion Controlling Agent (E)]

In the present embodiment, the resist composition may contain an acid diffusion controlling agent (E) having a function of controlling diffusion of an acid generated from an acid generating agent by radiation irradiation in a resist film to inhibit any unpreferable chemical reaction in an unexposed region or the like. By using such an acid diffusion controlling agent (E), the storage stability of a resist composition is improved. Also, along with the improvement of the resolution, the line width change of a resist pattern due to variation in the post exposure delay time before radiation irradiation and the post exposure delay time after radiation irradiation can be inhibited, and the composition has extremely excellent process stability. Such an acid diffusion controlling agent (E) is not particularly limited, and examples thereof include a radiation degradable basic compound such as a nitrogen atom-containing basic compound, a basic sulfonium compound, and a basic iodonium compound.

The above acid diffusion controlling agent (E) is not particularly limited, and, for example, an acid diffusion controlling agent described in International Publication No. WO 2013/024778 can be used. The acid diffusion controlling agent (E) can be used alone or in combination of two or more kinds.

The content of the acid diffusion controlling agent (E) is preferably 0.001 to 49% by mass of the total weight of the solid components, more preferably 0.01 to 10% by mass, still more preferably 0.01 to 5% by mass, and particularly preferably 0.01 to 3% by mass. Within the above range, there is a tendency that a decrease in resolution, and deterioration of the pattern shape and the dimension fidelity or the like can be prevented. Moreover, even though the post exposure delay time from electron beam irradiation to heating after radiation irradiation becomes longer, there is a tendency that deterioration of the shape of the pattern upper layer portion can be prevented. Also, when the content is 10% by mass or less, there is a tendency that a decrease in sensitivity, and developability of the unexposed portion or the like can be prevented. By using such an acid diffusion controlling agent, there is a tendency that the storage stability of a resist composition is improved, that the resolution is also improved, that the line width change of a resist pattern due to variation in the post exposure delay time before radiation irradiation and the post exposure delay time after radiation irradiation can be inhibited, and that the composition has extremely excellent process stability.

[Further Component (F)]

To the resist composition of the present embodiment, if required, as the further component (F), one kind or two or more kinds of various additive agents such as a dissolution promoting agent, a dissolution controlling agent, a sensitizing agent, a surfactant, and an organic carboxylic acid or an oxo acid of phosphor or derivative thereof can be added.

[Dissolution Promoting Agent]

A low molecular weight dissolution promoting agent is a component having a function of increasing the solubility of the component (A) of the present embodiment in a developing solution to moderately increase the dissolution rate of the component (A) upon developing, when the solubility of the component is too low. The low molecular weight dissolution promoting agent can be used, if required. Examples of the above dissolution promoting agent can include a phenolic compound having a low molecular weight, such as a bisphenol and a tris(hydroxyphenyl)methane. These dissolution promoting agents can be used alone or in mixture of two or more kinds.

The content of the dissolution promoting agent, which is arbitrarily adjusted according to the kind of the component (A) to be used, is preferably 0 to 49% by mass of the total weight of the solid components, more preferably 0 to 5% by mass, still more preferably 0 to 1% by mass, and particularly preferably 0% by mass.

[Dissolution Controlling Agent]

The dissolution controlling agent is a component having a function of controlling the solubility of the component (A) of the present embodiment in a developing solution to moderately decrease the dissolution rate upon developing, when the solubility of the component is too high. As such a dissolution controlling agent, the one which does not chemically change in steps such as calcination of resist coating, radiation irradiation, and development is preferable.

The dissolution controlling agent is not particularly limited, and examples thereof can include an aromatic hydrocarbon such as phenanthrene, anthracene and acenaphthene; a ketone such as acetophenone, benzophenone and phenyl naphthyl ketone; and a sulfone such as methyl phenyl sulfone, diphenyl sulfone and dinaphthyl sulfone. These dissolution controlling agents can be used alone or in combination of two or more kinds.

The content of the dissolution controlling agent, which is arbitrarily adjusted according to the kind of the component (A) to be used, is preferably 0 to 49% by mass of the total weight of the solid components, more preferably 0 to 5% by mass, still more preferably 0 to 1% by mass, and particularly preferably 0% by mass.

[Sensitizing Agent]

The sensitizing agent is a component having a function of absorbing irradiated radiation energy, transmitting the energy to the acid generating agent (C), and thereby increasing the acid production amount, and improving the apparent sensitivity of a resist. Examples of such a sensitizing agent can include, but not particularly limited to, a benzophenone, a biacetyl, a pyrene, a phenothiazine and a fluorene. These sensitizing agents can be used alone or in combination of two or more kinds.

The content of the sensitizing agent, which is arbitrarily adjusted according to the kind of the component (A) to be used, is preferably 0 to 49% by mass of the total weight of the solid components, more preferably 0 to 5% by mass, still more preferably 0 to 1% by mass, and particularly preferably 0% by mass.

[Surfactant]

The surfactant is a component having a function of improving coatability and striation of the resist composition of the present embodiment, and developability of a resist or the like. Such a surfactant may be any of anionic, cationic, nonionic, and amphoteric surfactants. A preferable surfactant is a nonionic surfactant. The nonionic surfactant has a good affinity with a solvent used in production of resist compositions and more effects. Examples of the nonionic surfactant include, but not particularly limited to, a polyoxyethylene higher alkyl ether, a polyoxyethylene higher alkyl phenyl ether, and a higher fatty acid diester of polyethylene glycol. Examples of the commercially available product thereof can include, but not particularly limited to, hereinafter by trade name, EFTOP (manufactured by Jemco Inc.), MEGAFAC (manufactured by DIC Corporation), Fluorad (manufactured by Sumitomo 3M Limited), Asahi-Guard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Chemical Co., Ltd.).

The content of the surfactant, which is arbitrarily adjusted according to the kind of the component (A) to be used, is preferably 0 to 49% by mass of the total weight of the solid components, more preferably 0 to 5% by mass, still more preferably 0 to 1% by mass, and particularly preferably 0% by mass.

[Organic Carboxylic Acid or Oxo Acid of Phosphor or Derivative Thereof]

For the purpose of prevention of sensitivity deterioration or improvement of a resist pattern shape and post exposure delay stability or the like, and as an additional optional component, the resist composition of the present embodiment can contain an organic carboxylic acid or an oxo acid of phosphor or derivative thereof. The organic carboxylic acid or the oxo acid of phosphor or derivative thereof can be used in combination with the acid diffusion controlling agent, or may be used alone. Suitable examples of the organic carboxylic acid include malonic acid, citric acid, malic acid, succinic acid, benzoic acid and salicylic acid. Examples of the oxo acid of phosphor or derivative thereof include phosphoric acid or derivative thereof such as ester including phosphoric acid, di-n-butyl phosphate and diphenyl phosphate; phosphonic acid or derivative thereof such as ester including phosphonic acid, dimethyl phosphonate, di-n-butyl phosphonate, phenylphosphonic acid, diphenyl phosphonate and dibenzyl phosphonate; and phosphinic acid and derivative thereof such as ester including phosphinic acid and phenylphosphinic acid. Among them, phosphonic acid is particularly preferable.

The organic carboxylic acid or the oxo acid of phosphor or derivative thereof can be used alone or in combination of two or more kinds. The content of the organic carboxylic acid or the oxo acid of phosphor or derivative thereof, which is arbitrarily adjusted according to the kind of the component (A) to be used, is preferably 0 to 49% by mass of the total weight of the solid components, more preferably 0 to 5% by mass, still more preferably 0 to 1% by mass, and particularly preferably 0% by mass.

[Further Additive Agent Other than Above Additive Agents (Dissolution Promoting Agent, Dissolution Controlling Agent, Sensitizing Agent, Surfactant, and Organic Carboxylic Acid or Oxo Acid of Phosphor or Derivative Thereof)]

Furthermore, the resist composition of the present embodiment can contain one kind or two or more kinds of additive agents other than the above dissolution controlling agent, sensitizing agent, surfactant, and organic carboxylic acid or oxo acid of phosphor or derivative thereof if required. Examples of such an additive agent include a dye, a pigment, and an adhesion aid. For example, when the composition contains the dye or the pigment, a latent image of the exposed portion is visualized and influence of halation upon exposure can be alleviated, which is preferable. In addition, when the composition contains the adhesion aid, adhesiveness to a substrate can be improved, which is preferable. Furthermore, examples of other additive agent can include, but not particularly limited to, a halation preventing agent, a storage stabilizing agent, a defoaming agent, and a shape improving agent. Specific examples thereof can include 4-hydroxy-4'-methylchalkone.

In the resist composition of the present embodiment, the total content of the optional component (F) is preferably 0 to 99% by mass of the total weight of the solid components, more preferably 0 to 49% by mass, still more preferably 0 to 10% by mass, further preferably 0 to 5% by mass, still further preferably 0 to 1% by mass, and particularly preferably 0% by mass.

[Content Ratio of Each Component in Resist Composition]

In the resist composition of the present embodiment, the content of the component (A) of the present embodiment is not particularly limited, but is preferably 50 to 99.4% by mass of the total mass of the solid components (summation of solid components including the component (A), and optionally used components such as acid generating agent (C), acid crosslinking agent (G), acid diffusion controlling agent (E), and further component (F) (also referred to as "optional component (F)"), hereinafter the same), more preferably 55 to 90% by mass, still more preferably 60 to 80% by mass, and particularly preferably 60 to 70% by mass. In the case of the above content, there is a tendency that resolution is further improved and that line edge roughness (LER) is further decreased. When both the compound and the resin of the present embodiment are contained, the above content refers to the total amount of the compound and the resin of the present embodiment.

In the resist composition of the present embodiment, the content ratio of the compound and/or the resin of the present embodiment (component (A)), the acid generating agent (C), the acid crosslinking agent (G), the acid diffusion controlling agent (E), and the optional component (F) (the component (A)/the acid generating agent (C)/the acid crosslinking agent (G)/the acid diffusion controlling agent (E)/the optional component (F)) is preferably 50 to 99.4% by mass/0.001 to 49% by mass/0.5 to 49% by mass/0.001 to 49% by mass/0 to 49% by mass based on 100% by mass of the solid content of the resist composition, more preferably 55 to 90% by mass/i to 40% by mass/0.5 to 40% by mass/0.01 to 10% by mass/0 to 5% by mass, still more preferably 60 to 80% by mass/3 to 30% by mass/i to 30% by mass/0.01 to 5% by mass/0 to 1% by mass, and particularly preferably 60 to 70% by mass/10 to 25% by mass/2 to 20% by mass/0.01 to 3% by mass/0% by mass. The content ratio of each component is selected from each range so that the summation thereof is 100% by mass. By the above content ratio, performance such as sensitivity, resolution, and developability tends to be further excellent. The "solid content" refers to components except for the solvent. "100% by mass of the solid content" refer to 100% by mass of the components except for the solvent.

The resist composition of the present embodiment is generally prepared by dissolving each component in a solvent upon use into a homogeneous solution, and then if required, filtering through a filter or the like with a pore diameter of about 0.2 μm, for example.

The resist composition of the present embodiment can contain an additional resin other than the resin of the present embodiment, if required. Examples of the additional resin include, but not particularly limited to, a novolac resin, a polyvinyl phenol, a polyacrylic acid, a polyvinyl alcohol, a styrene-maleic anhydride resin, and a polymer containing acrylic acid, vinyl alcohol or vinylphenol as a monomeric unit, and derivatives thereof. The content of the above resin is not particularly limited and is arbitrarily adjusted according to the kind of the component (A) to be used, and is preferably 30 parts by mass or less based on 100 parts by mass of the component (A), more preferably 10 parts by mass or less, still more preferably 5 parts by mass or less, and particularly preferably 0 parts by mass.

[Physical Properties and the Like of Resist Composition]

The resist composition of the present embodiment can form an amorphous film by spin coating. Also, the resist composition can be applied to a general semiconductor production process. Any of positive type and negative type resist patterns can be individually prepared depending on the kind of a developing solution to be used.

In the case of a positive type resist pattern, the dissolution rate of the amorphous film formed by spin coating with the resist composition of the present embodiment in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film easily forms a resist. When the amorphous film has a dissolution rate of 0.0005 angstrom/sec or more, the resolution tends to be improved. It is presumed that this is because due to the change in the solubility before and after exposure of the component (A), contrast at the interface between the exposed portion being dissolved in a developing solution and the unexposed portion not being dissolved in a developing solution is increased. Also, effects of reducing LER and defects are easily obtained.

In the case of a negative type resist pattern, the dissolution rate of the amorphous film formed by spin coating with the resist composition of the present embodiment in a developing solution at 23° C. is preferably 10 angstrom/sec or more. When the dissolution rate is 10 angstrom/sec or more, the amorphous film more easily dissolves in a developing solution, and is further suitable as a resist. When the amorphous film has a dissolution rate of 10 angstrom/sec or more, the resolution tends to be improved. It is presumed that this is because the micro surface portion of the component (A) dissolves, and LER is reduced. Also, effects of reducing defects are easily obtained.

The above dissolution rate can be determined by immersing the amorphous film in a developing solution for a predetermined period of time at 23° C. and then measuring the film thickness before and after the immersion by a publicly known method such as visual inspection, ellipsometry, or cross-sectional observation with a scanning electron microscope.

In the case of a positive type resist pattern, the dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 10 angstrom/sec or more. When the dissolution rate is 10 angstrom/sec or more, the amorphous film more easily dissolves in a developing solution, and is further suitable as a resist. When the amorphous film has a dissolution rate of 10 angstrom/sec or more, the resolution tends to be improved. It is presumed that this is because the micro surface portion of the component (A) dissolves, and LER is reduced. Also, effects of reducing defects are easily obtained.

In the case of a negative type resist pattern, the dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film easily forms a resist. When the amorphous film has a dissolution rate of 0.0005 angstrom/sec or more, the resolution tends to be improved. It is presumed that this is because due to the change in the solubility before and after exposure of the component (A), contrast at the interface between the unexposed portion being dissolved in a developing solution and the exposed portion not being dissolved in a developing solution is increased. Also, effects of reducing LER and defects are easily obtained.

[Radiation-Sensitive Composition]

The radiation-sensitive composition of the present embodiment contains the component (A) of the present embodiment, an optically active diazonaphthoquinone compound (B) and a solvent, and the content of the solvent is preferably 20 to 99% by mass based on 100% by mass in total of the radiation-sensitive composition whereas the content of components except for the solvent is preferably 1 to 80% by mass based on 100% by mass in total of the radiation-sensitive composition.

The component (A) to be contained in the radiation-sensitive composition of the present embodiment is used in combination with the optically active diazonaphthoquinone compound (B), which will be mentioned later, and is useful as a base material for positive type resists that becomes a compound easily soluble in a developing solution by irradiation with g-ray, h-ray, i-ray, KrF excimer laser, ArF excimer laser, extreme ultraviolet, electron beam, or X-ray. Although the properties of the component (A) are not largely altered by g-ray, h-ray, i-ray, KrF excimer laser, ArF excimer laser, extreme ultraviolet, electron beam, or X-ray, the optically active diazonaphthoquinone compound (B) poorly soluble in a developing solution is converted to an easily soluble compound so that a resist pattern can be formed in a development step.

Since the component (A) to be contained in the radiation-sensitive composition of the present embodiment is a compound having a relatively low molecular weight, the obtained resist pattern has very small roughness.

The glass transition temperature of the component (A) to be contained in the radiation-sensitive composition of the present embodiment is preferably 100° C. or higher, more preferably 120° C. or higher, still more preferably 140° C. or higher, and particularly preferably 150° C. or higher. The upper limit of the glass transition temperature of the component (A) is not particularly limited and is, for example, 400° C. When the glass transition temperature of the component (A) falls within the above range, the resulting radiation-sensitive composition has heat resistance capable of maintaining a pattern shape in a semiconductor lithography process, and improves performance such as high resolution.

The heat of crystallization determined by the differential scanning calorimetry of the glass transition temperature of the component (A) to be contained in the radiation-sensitive composition of the present embodiment is preferably less than 20 J/g. Also, (Crystallization temperature)−(Glass transition temperature) is preferably 70° C. or more, more preferably 80° C. or more, still more preferably 100° C. or more, and particularly preferably 130° C. or more. When the heat of crystallization is less than 20 J/g or when (Crystallization temperature)−(Glass transition temperature) falls within the above range, there is a tendency that the radiation-sensitive composition easily forms an amorphous film by spin coating, can maintain film formability necessary for a resist over a long period, and can improve resolution.

In the present embodiment, the above heat of crystallization, crystallization temperature, and glass transition temperature can be determined by differential scanning calorimetry using "DSC/TA-50WS" manufactured by Shimadzu Corp. For example, about 10 mg of a sample is placed in an unsealed container made of aluminum, and the temperature is raised to the melting point or more at a temperature increase rate of 20° C./min in a nitrogen gas stream (50 mL/min). After quenching, again the temperature is raised to the melting point or more at a temperature increase rate of 20° C./min in a nitrogen gas stream (30 mL/min). After further quenching, again the temperature is raised to 400° C. at a temperature increase rate of 20° C./min in a nitrogen gas stream (30 mL/min). The temperature at the middle point (where the specific heat is changed into the half) of steps in the baseline shifted in a step-like pattern is defined as the glass transition temperature (Tg). The temperature of the subsequently appearing exothermic peak is defined as the crystallization temperature. The heat is determined from the area of a region surrounded by the exothermic peak and the baseline and defined as the heat of crystallization.

The component (A) to be contained in the radiation-sensitive composition of the present embodiment is preferably low sublimable at 100 or lower, preferably 120° C. or lower, more preferably 130° C. or lower, still more preferably 140° C. or lower, and particularly preferably 150° C. or lower at normal pressure. The low sublimability means that in thermogravimetry, weight reduction when the resist base material is kept at a predetermined temperature for 10 minutes is 10% or less, preferably 5% or less, more preferably 3% or less, still more preferably 1% or less, and particularly preferably 0.1% or less. The low sublimability can prevent an exposure apparatus from being contaminated by outgassing upon exposure. In addition, there is a tendency that a good pattern shape with low roughness can be obtained.

The component (A) to be contained in the radiation-sensitive composition of the present embodiment dissolves at preferably 1% by mass or more, more preferably 5% by mass or more, and still more preferably 10% by mass or more at 23° C. in a solvent that is selected from propylene glycol monomethyl ether acetate (PGMEA), propylene glycol monomethyl ether (PGME), cyclohexanone (CHN), cyclopentanone (CPN), 2-heptanone, anisole, butyl acetate, ethyl propionate, and ethyl lactate and exhibits the highest ability to dissolve the component (A). Further preferably, the component (A) dissolves at 20% by mass or more at 23° C. in a solvent that is selected from PGMEA, PGME, and CHN and exhibits the highest ability to dissolve the component (A). Particularly preferably, the component (A) dissolves at 20% by mass or more at 23° C. in PGMEA. When the above conditions are met, there is a tendency that the radiation-sensitive composition can be used in a semiconductor production process at a full production scale.

[Optically Active Diazonaphthoquinone Compound (B)]

The optically active diazonaphthoquinone compound (B) to be contained in the radiation-sensitive composition of the present embodiment is a diazonaphthoquinone substance including a polymer or non-polymer optically active diazonaphthoquinone compound and is not particularly limited as long as it is generally used as a photosensitive component (sensitizing agent) in positive type resist compositions. One kind or two or more kinds can be optionally selected and used.

Such a sensitizing agent is preferably a compound obtained by reacting naphthoquinonediazide sulfonic acid chloride, benzoquinonediazide sulfonic acid chloride, or the like with a low molecular weight compound or a high molecular weight compound having a functional group condensable with these acid chlorides. Here, examples of the above functional group condensable with the acid chlorides include, but not particularly limited to, a hydroxy group and an amino group. Particularly, a hydroxy group is suitable. Examples of the compound containing a hydroxy group condensable with the acid chlorides can include, but not particularly limited to, hydroquinone; resorcin; hydroxybenzophenones such as 2,4-dihydroxybenzophenone, 2,3,4-trihydroxybenzophenone, 2,4,6-trihydroxybenzophenone, 2,4,4'-trihydroxybenzophenone, 2,3,4,4'-tetrahydroxybenzophenone, 2,2',4,4'-tetrahydroxybenzophenone, and 2,2',3,4,6'-pentahydroxybenzophenone; hydroxyphenylalkanes such as bis(2,4-dihydroxyphenyl)methane, bis(2,3,4-trihydroxyphenyl)methane, and bis(2,4-dihydroxyphenyl)propane; and hydroxytriphenylmethanes such as 4,4',3",4"-tetrahydroxy-3,5,3',5'-tetramethyltriphenylmethane and 4,4',2",3",4"-pentahydroxy-3,5,3',5'-tetramethyltriphenylmethane.

Also, preferable examples of the acid chloride such as naphthoquinonediazide sulfonic acid chloride or benzoquinonediazide sulfonic acid chloride include 1,2-naphthoquinonediazide-5-sulfonyl chloride and 1,2-naphthoquinonediazide-4-sulfonyl chloride.

The radiation-sensitive composition of the present embodiment is preferably prepared by, for example, dissolving each component in a solvent upon use into a homogeneous solution, and then if required, filtering through a filter or the like with a pore diameter of about 0.2 μm, for example.

[Solvent]

Examples of the solvent that can be used in the radiation-sensitive composition of the present embodiment include, but not particularly limited to, propylene glycol monomethyl ether acetate, propylene glycol monomethyl ether, cyclohexanone, cyclopentanone, 2-heptanone, anisole, butyl acetate, ethyl propionate, and ethyl lactate. Among them, propylene glycol monomethyl ether acetate, propylene glycol monomethyl ether, or cyclohexanone is preferable. The solvent may be used alone as one kind or may be used in combination of two or more kinds.

The content of the solvent is 20 to 99% by mass based on 100% by mass in total of the radiation-sensitive composition, preferably 50 to 99% by mass, more preferably 60 to 98% by mass, and particularly preferably 90 to 98% by mass.

The content of components except for the solvent (solid components) is 1 to 80% by mass based on 100% by mass in total of the radiation-sensitive composition, preferably 1 to 50% by mass, more preferably 2 to 40% by mass, and particularly preferably 2 to 10% by mass.

[Properties of Radiation-Sensitive Composition]

The radiation-sensitive composition of the present embodiment can form an amorphous film by spin coating. Also, the radiation-sensitive composition of the present embodiment can be applied to a general semiconductor production process. Any of positive type and negative type resist patterns can be individually prepared depending on the kind of a developing solution to be used.

In the case of a positive type resist pattern, the dissolution rate of the amorphous film formed by spin coating with the radiation-sensitive composition of the present embodiment in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film easily forms a resist. When the amorphous film has a dissolution rate of 0.0005 angstrom/sec or more, the resolution tends to be improved. It is presumed that this is because due to the change in the solubility before and after exposure of the component (A), contrast at the interface between the exposed portion being dissolved in a developing solution and the unexposed portion not being dissolved in a developing solution is increased. Also, effects of reducing LER and defects are easily obtained.

In the case of a negative type resist pattern, the dissolution rate of the amorphous film formed by spin coating with the radiation-sensitive composition of the present embodiment in a developing solution at 23° C. is preferably 10 angstrom/sec or more. When the dissolution rate is 10 angstrom/sec or more, the amorphous film more easily dissolves in a developing solution, and is further suitable as a resist. When the amorphous film has a dissolution rate of 10 angstrom/sec or more, the resolution tends to be improved. It is presumed that this is because the micro surface portion of the component (A) dissolves, and LER is reduced. Also, effects of reducing defects are easily obtained.

The above dissolution rate can be determined by immersing the amorphous film in a developing solution for a predetermined period of time at 23° C. and then measuring the film thickness before and after the immersion by a publicly known method such as visual inspection, ellipsometry, or QCM method.

In the case of a positive type resist pattern, the dissolution rate of the exposed portion after irradiation with radiation such as KrF excimer laser, extreme ultraviolet, electron beam or X-ray, or after heating at 20 to 500° C., of the amorphous film formed by spin coating with the radiation-sensitive composition of the present embodiment, in a developing solution at 23° C. is preferably 10 angstrom/sec or more, more preferably 10 to 10000 angstrom/sec, and still more preferably 100 to 1000 angstrom/sec. When the dissolution rate is 10 angstrom/sec or more, the amorphous film more easily dissolves in a developing solution, and is further suitable as a resist. When the amorphous film has a dissolution rate of 10000 angstrom/sec or less, the resolution tends to be improved. It is presumed that this is because the micro surface portion of the component (A) dissolves, and LER is reduced. Also, effects of reducing defects are easily obtained.

In the case of a negative type resist pattern, the dissolution rate of the exposed portion after irradiation with radiation such as KrF excimer laser, extreme ultraviolet, electron beam or X-ray, or after heating at 20 to 500° C., of the amorphous film formed by spin coating with the radiation-sensitive composition of the present embodiment, in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film easily forms a resist. When the amorphous film has a dissolution rate of 0.0005 angstrom/sec or more, the resolution tends to be improved. It is presumed that this is because due to the change in the solubility before and after exposure of the component (A), contrast at the interface between the unexposed portion being dissolved in a developing solution and the exposed portion not being dissolved in a developing solution is increased. Also, effects of reducing LER and defects are easily obtained.

[Content Ratio of Each Component in Radiation-Sensitive Composition]

In the radiation-sensitive composition of the present embodiment, the content of the component (A) is preferably 1 to 99% by mass based on the total weight of the solid components (summation of the component (A), the optically active diazonaphthoquinone compound (B), and optionally used solid components such as further component (D), hereinafter the same), more preferably 5 to 95% by mass, still more preferably 10 to 90% by mass, and particularly preferably 25 to 75% by mass. When the content of the component (A) falls within the above range, there is a tendency that the radiation-sensitive composition of the present embodiment can produce a pattern with high sensitivity and low roughness.

In the radiation-sensitive composition of the present embodiment, the content of the optically active diazonaphthoquinone compound (B) is preferably 1 to 99% by mass based on the total weight of the solid components (summation of the component (A), the optically active diazonaphthoquinone compound (B), and optionally used solid components such as further component (D), hereinafter the same), more preferably 5 to 95% by mass, still more preferably 10 to 90% by mass, and particularly preferably 25 to 75% by mass. When the content of the optically active diazonaphthoquinone compound (B) falls within the above range, there is a tendency that the radiation-sensitive composition of the present embodiment can produce a pattern with high sensitivity and low roughness.

[Further Component (D)]

To the radiation-sensitive composition of the present embodiment, if required, as a component other than the component (A) and the optically active diazonaphthoquinone compound (B), one kind or two or more kinds of various additive agents such as the above acid generating agent, acid crosslinking agent, acid diffusion controlling agent, dissolution promoting agent, dissolution controlling agent, sensitizing agent, surfactant, and organic carboxylic acid or oxo acid of phosphor or derivative thereof can be added. In the present specification, the further component (D) is also referred to as an optional component (D).

The content ratio of the component (A), the optically active diazonaphthoquinone compound (B), and the further optional component (D) that may be optionally contained in the radiation-sensitive composition ((A)/(B)/(D)) is preferably 1 to 99% by mass/99 to 1% by mass/0 to 98% by mass based on 100% by mass of the solid content of the radiation-sensitive composition, more preferably 5 to 95% by mass/95 to 5% by mass/0 to 49% by mass, still more preferably 10 to 90% by mass/90 to 10% by mass/0 to 10% by mass, particularly preferably 20 to 80% by mass/80 to 20% by mass/0 to 5% by mass, and most preferably 25 to 75% by mass/75 to 25% by mass/0% by mass.

The content ratio of each component is selected from each range so that the summation thereof is 100% by mass. When the content ratio of each component falls within the above range, the radiation-sensitive composition of the present embodiment tends to be excellent in performance such as sensitivity and resolution, in addition to roughness.

The radiation-sensitive composition of the present embodiment may contain a resin other than that of the present embodiment. Examples of such a resin include a novolac resin, a polyvinyl phenol, a polyacrylic acid, a polyvinyl alcohol, a styrene-maleic anhydride resin, and a polymer containing acrylic acid, vinyl alcohol or vinylphenol as a monomeric unit, and derivatives thereof. The content of these resins, which is arbitrarily adjusted according to the kind of the component (A) to be used, is preferably 30 parts by mass or less based on 100 parts by mass of the component (A), more preferably 10 parts by mass or less, still more preferably 5 parts by mass or less, and particularly preferably 0 parts by mass.

[Method for Producing Amorphous Film]

The method for producing an amorphous film of the present embodiment comprises the step of forming an amorphous film on a substrate using the above radiation-sensitive composition.

[Resist Pattern Formation Method Using Radiation-Sensitive Composition]

A resist pattern formation method using the radiation-sensitive composition of the present embodiment includes the steps of: forming a resist film on a substrate using the above radiation-sensitive composition; exposing at least a portion of the formed resist film; and developing the exposed resist film, thereby forming a resist pattern. Specifically, the same operation as in the following resist pattern formation method using the resist composition can be performed.

[Resist Pattern Formation Method Using Resist Composition]

A resist pattern formation method using the resist composition of the present embodiment includes the steps of: forming a resist film on a substrate using the above resist composition of the present embodiment; exposing at least a portion of the formed resist film; and developing the exposed resist film, thereby forming a resist pattern. The resist pattern according to the present embodiment can also be formed as an upper layer resist in a multilayer process. Also, the resist pattern formation method of the present embodiment can also be applied as a method for forming a resist permanent film, which will be mentioned later.

Examples of the resist pattern formation method include, but not particularly limited to, the following method. A resist film is formed by coating a conventionally publicly known substrate with the above resist composition of the present embodiment using a coating means such as spin coating, flow casting coating, and roll coating. Examples of the conventionally publicly known substrate can include, but not particularly limited to, a substrate for electronic components, and the one having a predetermined wiring pattern formed thereon, or the like. More specific examples thereof include, but not particularly limited to, a silicon wafer, a substrate made of a metal such as copper, chromium, iron and aluminum, and a glass substrate. Examples of the wiring pattern material include, but not particularly limited to, copper, aluminum, nickel and gold. Also if required, the substrate may be a substrate having an inorganic and/or organic film provided thereon. Examples of the inorganic film include, but not particularly limited to, an inorganic antireflection film (inorganic BARC). Examples of the organic film include, but not particularly limited to, an organic antireflection film (organic BARC). The substrate may be subjected to surface treatment with hexamethylene disilazane or the like.

Next, the coated substrate is heated if required. The heating conditions vary according to the compounding composition of the resist composition, or the like, but are preferably 20 to 250° C., and more preferably 20 to 150° C. By heating, the adhesiveness of a resist to a substrate may be improved, which is preferable. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like are arbitrarily selected according to the compounding composition of the resist composition, or the like. In the present embodiment, in order to stably form a fine pattern with a high degree of accuracy in exposure, the resist film is preferably heated after radiation irradiation.

Next, by developing the exposed resist film in a developing solution, a predetermined resist pattern is formed. As the above developing solution, it is preferable to select a solvent having a solubility parameter (SP value) close to that of the component (A) to be used. A polar solvent such as a ketone-based solvent, an ester-based solvent, an alcohol-based solvent, an amide-based solvent and an ether-based solvent; and a hydrocarbon-based solvent, or an alkaline aqueous solution can be used.

Examples of the ketone-based solvent can include, but not particularly limited to, 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

Examples of the ester-based solvent can include, but not particularly limited to, methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

Examples of the alcohol-based solvent can include, but not particularly limited to, an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include, but not particularly limited to, dioxane and tetrahydrofuran in addition to the above glycol ether-based solvent.

Examples of the amide-based solvent to be used include, but not particularly limited to, N-methyl-2-pyrrolidone, N,N-dimethylacetamide, N,N-dimethylformamide, phosphoric hexamethyltriamide, and 1,3-dimethyl-2-imidazolidinone.

Examples of the hydrocarbon-based solvent include, but not particularly limited to, an aromatic hydrocarbon-based solvent such as toluene and xylene; and an aliphatic hydrocarbon-based solvent such as pentane, hexane, octane, and decane.

A plurality of above solvents may be mixed, or the solvent may be used by mixing the solvent with a solvent other than those described above or water within the range having performance. In order to sufficiently exhibit the effect of the present invention, the water content ratio as the whole developing solution is preferably less than 70% by mass, more preferably less than 50% by mass, still more preferably less than 30% by mass, and further preferably less than 10% by mass. Particularly preferably, the developing solution is substantially moisture free. That is, the content of the organic solvent in the developing solution is preferably 30% by mass or more and 100% by mass or less based on the total amount of the developing solution, more preferably 50% by mass or more and 100% by mass or less, still more preferably 70% by mass or more and 100% by mass or less, further preferably 90% by mass or more and 100% by mass or less, and particularly preferably 95% by mass or more and 100% by mass or less.

Examples of the alkaline aqueous solution include, but not particularly limited to, an alkaline compound such as mono-, di- or tri-alkylamine, mono-, di- or tri-alkanolamine, heterocyclic amine, tetramethyl ammonium hydroxide (TMAH), and choline.

Particularly, the developing solution containing at least one kind of solvent selected from a ketone-based solvent, an ester-based solvent, an alcohol-based solvent, an amide-based solvent, and an ether-based solvent improves resist performance such as resolution and roughness of the resist pattern, which is preferable.

To the developing solution, a surfactant can be added in an appropriate amount, if required.

The surfactant is not particularly limited but, for example, an ionic or nonionic fluorine-based and/or silicon-based surfactant can be used. Examples of the fluorine-based and/or silicon-based surfactant can include the surfactants described in Japanese Patent Laid-Open Nos. 62-36663, 61-226746, 61-226745, 62-170950, 63-34540, 7-230165, 8-62834, 9-54432, and 9-5988, and U.S. Pat. Nos. 5,405, 720, 5,360,692, 5,529,881, 5,296,330, 5,436,098, 5,576,143, 5,294,511, and 5,824,451. The surfactant is preferably a nonionic surfactant. The nonionic surfactant is not particularly limited, but a fluorine-based surfactant or a silicon-based surfactant is further preferably used.

The amount of the surfactant used is usually 0.001 to 5% by mass based on the total amount of the developing solution, preferably 0.005 to 2% by mass, and further preferably 0.01 to 0.5% by mass.

For the development method, without particular limitations, for example, a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method), or the like may be applied. The time for conducting the pattern development is not particularly limited, but is preferably 10 seconds to 90 seconds.

After the step of conducting development, a step of stopping the development by the replacement with another solvent may be practiced.

A step of rinsing the resist film with a rinsing solution containing an organic solvent is preferably provided after the development.

The rinsing solution used in the rinsing step after development is not particularly limited as long as the rinsing solution does not dissolve the resist pattern cured by cross-linking. A solution containing a general organic solvent or water may be used as the rinsing solution. As the foregoing rinsing solution, a rinsing solution containing at least one kind of organic solvent selected from a hydrocarbon-based solvent, a ketone-based solvent, an ester-based solvent, an alcohol-based solvent, an amide-based solvent, and an ether-based solvent is preferably used. More preferably, after development, a step of rinsing the film by using a rinsing solution containing at least one kind of organic solvent selected from the group consisting of a ketone-based solvent, an ester-based solvent, an alcohol-based solvent and an amide-based solvent is conducted. Still more preferably, after development, a step of rinsing the film by using a rinsing solution containing an alcohol-based solvent or an ester-based solvent is conducted. Still more preferably, after development, a step of rinsing the film by using a rinsing solution containing a monohydric alcohol is conducted. Particularly preferably, after development, a step of rinsing the film by using a rinsing solution containing a monohydric alcohol having 5 or more carbon atoms is conducted. The time for rinsing the pattern is not particularly limited, but is preferably 10 seconds to 90 seconds.

Here, examples of the monohydric alcohol to be used in the rinsing step after development include a linear, branched or cyclic monohydric alcohol. Specifically, without particular limitations, for example, 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, 4-octanol or the like can be used. As the particularly preferable monohydric alcohol having 5 or more carbon atoms, 1-hexanol, 2-hexanol, 4-methyl-2-pentanol, 1-pentanol, 3-methyl-1-butanol or the like can be used.

A plurality of these components may be mixed, or the component may be used by mixing the component with an organic solvent other than those described above.

The water content ratio in the rinsing solution is preferably 10% by mass or less, more preferably 5% by mass or less, and particularly preferably 3% by mass or less. When the water content ratio is 10% by mass or less, there is a tendency that a better development characteristic can be obtained.

The rinsing solution may also be used after adding an appropriate amount of a surfactant to the rinsing solution.

In the rinsing step, the wafer after development is rinsed using the above organic solvent-containing rinsing solution. The method of rinsing treatment is not particularly limited. However, for example, a method for continuously ejecting a rinsing solution on a substrate rotating at a constant speed (spin coating method), a method for dipping a substrate in a bath filled with a rinsing solution for a fixed time (dipping method), a method for spraying a rinsing solution on a substrate surface (spraying method), or the like can be applied. Above all, it is preferable to conduct the rinsing treatment by the spin coating method and after the rinsing, spin the substrate at a rotational speed of 2,000 rpm to 4,000 rpm, to remove the rinsing solution from the substrate surface.

After forming the resist pattern, a pattern wiring substrate is obtained by etching. Etching can be conducted by a publicly known method such as dry etching using plasma gas, and wet etching with an alkaline solution, a cupric chloride solution, and a ferric chloride solution or the like.

After forming the resist pattern, plating can also be conducted. Examples of the above plating method include copper plating, solder plating, nickel plating, and gold plating.

The remaining resist pattern after the etching can be stripped with an organic solvent. Examples of the above organic solvent include, but not particularly limited to, PGMEA (propylene glycol monomethyl ether acetate), PGME (propylene glycol monomethyl ether), and EL (ethyl lactate). Examples of the above stripping method include, but not particularly limited to, a dipping method and a spraying method. In addition, a wiring substrate having a resist pattern formed thereon may be a multilayer wiring substrate, and may have a small diameter through hole.

The wiring substrate obtained in the present embodiment can also be formed by a method for forming a resist pattern, then depositing a metal in vacuum, and subsequently dissolving the resist pattern in a solution, i.e., a liftoff method.

[Underlayer Film Forming Composition for Lithography]

The underlayer film forming composition for lithography of the present embodiment may contain an organic solvent, a crosslinking agent, an acid generating agent, and a further component, in addition to the compound or the resin of the present embodiment, if required. Hereinafter, these optional components will be described.

[Solvent]

The underlayer film forming composition for lithography of the present embodiment may contain a solvent. The solvent is not particularly limited as long as it is a solvent that can dissolves the compound or the resin of the present embodiment. Here, the compound or the resin of the present embodiment has excellent solubility in an organic solvent, as mentioned above, and therefore, various organic solvents are suitably used.

Examples of the solvent include, but not particularly limited to: a ketone-based solvent such as acetone, methyl ethyl ketone, methyl isobutyl ketone, and cyclohexanone; a cellosolve-based solvent such as propylene glycol monomethyl ether and propylene glycol monomethyl ether acetate; an ester-based solvent such as ethyl lactate, methyl acetate, ethyl acetate, butyl acetate, isoamyl acetate, ethyl lactate, methyl methoxypropionate, and methyl hydroxyisobutyrate; an alcohol-based solvent such as methanol, ethanol, isopropanol, and 1-ethoxy-2-propanol; and an aromatic hydrocarbon such as toluene, xylene, and anisole. These solvents are used alone as one kind or in combination of two or more kinds.

Among the above solvents, from the viewpoint of safety, one or more selected from the group consisting of cyclohexanone, propylene glycol monomethyl ether, propylene glycol monomethyl ether acetate, ethyl lactate, methyl hydroxyisobutyrate and anisole are preferable.

The content of the solvent is not particularly limited and is preferably 100 to 10,000 parts by mass based on 100 parts by mass of the film forming material for lithography, more preferably 200 to 5,000 parts by mass, and still more preferably 200 to 1,000 parts by mass, from the viewpoint of solubility and film formation.

[Crosslinking Agent]

The underlayer film forming composition for lithography of the present embodiment may contain a crosslinking agent from the viewpoint of, for example, suppressing intermixing. The crosslinking agent is not particularly limited, but a crosslinking agent described in, for example, International Publication No. WO 2013/024779 can be used.

Examples of the crosslinking agent include, but not particularly limited to, a phenol compound, an epoxy compound, a cyanate compound, an amino compound, a benzoxazine compound, an acrylate compound, a melamine compound, a guanamine compound, a glycoluril compound, a urea compound, an isocyanate compound, and an azide compound. These crosslinking agents are used alone as one kind or in combination of two or more kinds. Among them, one or more selected from the group consisting of a benzoxazine compound, an epoxy compound and a cyanate compound are preferable, and a benzoxazine compound is more preferable from the viewpoint of improvement in etching resistance.

As the phenol compound, a publicly known compound can be used. Examples of the phenol include phenol as well as an alkylphenol such as a cresol and a xylenol, a polyhydric phenol such as hydroquinone, a polycyclic phenol such as a naphthol and a naphthalenediol, a bisphenol such as bisphenol A and bisphenol F, and a polyfunctional phenol compound such as phenol novolac and a phenol aralkyl resin. These phenol compounds are used alone as one kind or in combination of two or more kinds. Among them, an aralkyl-based phenol resin is preferable from the viewpoint of heat resistance and solubility.

As the epoxy compound, a publicly known compound can be used and is selected from those having two or more epoxy groups in one molecule. Examples of the epoxy compound include, but not particularly limited to, epoxidation products of a dihydric phenol such as bisphenol A, bisphenol F, 3,3',5,5'-tetramethyl-bisphenol F, bisphenol S, fluorene bisphenol, 2,2'-biphenol, 3,3',5,5'-tetramethyl-4,4'-dihydroxybiphenol, resorcin, and a naphthalenediol; epoxidation products of a trihydric or higher phenol such as tris-(4-hydroxyphenyl)methane, 1,1,2,2-tetrakis(4-hydroxyphenyl) ethane, tris(2,3-epoxypropyl) isocyanurate, trimethylolmethane triglycidyl ether, trimethylolpropane triglycidyl ether, triethyloethane triglycidyl ether, phenol novolac, and o-cresol novolac; epoxidation products of a co-condensed resin of dicyclopentadiene and a phenol; epoxidation products of a phenol aralkyl resin synthesized from a phenol and paraxylylene dichloride; epoxidation products of a biphenyl aralkyl-based phenolic resin synthesized from a phenol and bischloromethylbiphenyl; and epoxidation products of a naphthol aralkyl resin synthesized from a naphthol and paraxylylene dichloride. These epoxy compounds are used alone as one kind or in combination of two or more kinds. Among them, an epoxy resin that is in a solid state at normal temperature, such as an epoxy resin obtained from a phenol aralkyl resin or a biphenyl aralkyl resin is preferable from the viewpoint of heat resistance and solubility.

The cyanate compound is not particularly limited as long as the compound has two or more cyanate groups in one molecule, and a publicly known compound can be used. Examples of the cyanate compound include those having a structure in which hydroxy groups of a compound having two or more hydroxy groups in one molecule are replaced with cyanate groups. Also, the cyanate compound preferably has an aromatic group, and those having a structure in which a cyanate group is directly bonded to the aromatic group can be suitably used. Examples of such a cyanate compound include those having a structure in which hydroxy groups of bisphenol A, bisphenol F, bisphenol M, bisphenol P, bisphenol E, a phenol novolac resin, a cresol novolac resin, a dicyclopentadiene novolac resin, tetramethylbisphenol F, a bisphenol A novolac resin, a brominated bisphenol A, a brominated phenol novolac resin, a trifunctional phenol, a tetrafunctional phenol, a naphthalene-based phenol, a biphenyl-based phenol, a phenol aralkyl resin, a biphenyl aralkyl resin, a naphthol aralkyl resin, a dicyclopentadiene aralkyl resin, an alicyclic phenol, a phosphorus-containing phenol, or the like are replaced with cyanate groups. These cyanate compounds are used alone as one kind or in combination of two or more kinds. Also, the above cyanate compound may be in any form of a monomer, an oligomer and a resin.

Examples of the amino compound include, but not particularly limited to, m-phenylenediamine, p-phenylenediamine, 4,4'-diaminodiphenylmethane, 4,4'-diaminodiphenylpropane, 4,4'-diaminodiphenyl ether, 3,4'-diaminodiphenyl ether, 3,3'-diaminodiphenyl ether, 4,4'-diaminodiphenylsulfone, 3,4'-diaminodiphenylsulfone, 3,3'-diaminodiphenylsulfone, 4,4'-diaminodiphenyl sulfide, 3,4'-diaminodiphenyl sulfide, 3,3'-diaminodiphenyl sulfide, 1,4-bis(4-aminophenoxy)benzene, 1,3-bis(4-aminophenoxy)benzene, 1,4-bis(3-aminophenoxy)benzene, 1,3-bis(3-aminophenoxy)benzene, bis[4-(4-aminophenoxy)phenyl]sulfone, 2,2-bis[4-(4-aminophenoxy)phenyl]propane, 2,2-bis[4-(3-aminophenoxy)phenyl]propane, 4,4'-bis(4- aminophenoxy)biphenyl, 4,4'-bis(3-aminophenoxy) biphenyl, bis[4-(4-aminophenoxy)phenyl] ether, bis[4-(3-aminophenoxy)phenyl] ether, 9,9-bis(4-aminophenyl) fluorene, 9,9-bis(4-amino-3-chlorophenyl)fluorene, 9,9-bis (4-amino-3-fluorophenyl)fluorene, 0-tolidine, m-tolidine, 4,4'-diaminobenzanilide, 2,2'-bis(trifluoromethyl)-4,4'-diaminobiphenyl, 4-aminophenyl-4-aminobenzoate, and 2-(4-aminophenyl)-6-aminobenzoxazole. These amino compounds are used alone as one kind or in combination of two or more kinds. Among them, preferable are one or more selected from the group consisting of an aromatic amine such as 4,4'-diaminodiphenylmethane, 4,4'-diaminodiphenylpropane, 4,4'-diaminodiphenyl ether, 3,4'-diaminodiphenyl ether, 3,3'-diaminodiphenyl ether, 4,4'-diaminodiphenylsulfone, 3,3'-diaminodiphenylsulfone, 1,4-bis(4-aminophenoxy)benzene, 1,3-bis(4-aminophenoxy)benzene, 1,4-bis(3-aminophenoxy)benzene, 1,3-bis(3-aminophenoxy)benzene, bis[4-(4-aminophenoxy)phenyl]sulfone, 2,2-bis[4-(4-aminophenoxy)phenyl]propane, 2,2-bis[4-(3-aminophenoxy)phenyl]propane, 4,4'-bis(4-aminophenoxy) biphenyl, 4,4'-bis(3-aminophenoxy)biphenyl, bis[4-(4-aminophenoxy)phenyl] ether, and bis[4-(3-aminophenoxy) phenyl] ether; an alicyclic amine such as diaminocyclohexane, diaminodicyclohexylmethane, dimethyl-diaminodicyclohexylmethane, tetramethyl-diaminodicyclohexylmethane, diaminodicyclohexylpropane, diaminobicyclo[2.2.1]heptane, bis(aminomethyl)-bicyclo[2.2.1] heptane, 3(4),8(9)-bis(aminomethyl)tricyclo[5.2.1.02,6] decane, 1,3-bisaminomethylcyclohexane, and isophoronediamine; and an aliphatic amine such as ethylenediamine, hexamethylenediamine, octamethylenediamine, decamethylenediamine, diethylenetriamine, and triethylenetetramine.

Examples of the benzoxazine compound include a P-d-based benzoxazine obtained from a difunctional diamine and a monofunctional phenol, and a F-a-based benzoxazine obtained from a monofunctional diamine and a difunctional phenol. These benzoxazine compounds are used alone as one kind or in combination of two or more kinds.

Examples of the melamine compound include hexamethylolmelamine, hexamethoxymethylmelamine, a compound in which 1 to 6 methylol groups of hexamethylolmelamine are methoxymethylated or a mixture thereof, hexamethoxyethylmelamine, hexaacyloxymethylmelamine, and a compound in which 1 to 6 methylol groups of hexamethylolmelamine are acyloxymethylated or a mixture thereof. These melamine compounds are used alone as one kind or in combination of two or more kinds.

Examples of the guanamine compound include tetramethylolguanamine, tetramethoxymethylguanamine, a compound in which 1 to 4 methylol groups of tetramethylolguanamine are methoxymethylated or a mixture thereof, tetramethoxyethylguanamine, tetraacyloxyguanamine, and a compound in which 1 to 4 methylol groups of tetramethylolguanamine are acyloxymethylated or a mixture thereof. These guanamine compounds are used alone as one kind or in combination of two or more kinds.

Examples of the glycoluril compound include tetramethylolglycoluril, tetramethoxyglycoluril, tetramethoxymethylglycoluril, a compound in which 1 to 4 methylol groups of tetramethylolglycoluril are methoxymethylated or a mixture thereof, and a compound in which 1 to 4 methylol groups of tetramethylolglycoluril are acyloxymethylated or a mixture thereof. These glycoluril compounds are used alone as one kind or in combination of two or more kinds.

Examples of the urea compound include tetramethylolurea, tetramethoxymethylurea, a compound in which 1 to 4 methylol groups of tetramethylolurea are methoxymethylated or a mixture thereof, and tetramethoxyethylurea. These urea compounds are used alone as one kind or in combination of two or more kinds.

In the underlayer film forming composition for lithography of the present embodiment, a crosslinking agent having at least one allyl group may be used from the viewpoint of improvement in crosslinkability. Examples of the crosslinking agent having at least one allyl group include, but not particularly limited to, an allylphenol such as 2,2-bis(3-allyl-4-hydroxyphenyl)propane, 1,1,1,3,3,3-hexafluoro-2,2-bis (3-allyl-4-hydroxyphenyl)propane, bis(3-allyl-4-hydroxyphenyl)sulfone, bis(3-allyl-4-hydroxyphenyl) sulfide, and bis(3-allyl-4-hydroxyphenyl) ether; an allyl cyanate such as 2,2-bis(3-allyl-4-cyanatophenyl)propane, 1,1,1,3,3,3-hexafluoro-2,2-bis(3-allyl-4-cyanatophenyl)propane, bis(3-allyl-4-cyanatophenyl)sulfone, bis(3-allyl-4-cyanatophenyl) sulfide, and bis(3-allyl-4-cyanatophenyl) ether; diallyl phthalate, diallyl isophthalate, diallyl terephthalate, triallyl isocyanurate, trimethylolpropane diallyl ether, and pentaerythritol allyl ether. These crosslinking agents are used alone as one kind or in combination of two or more kinds. Among them, an allylphenol such as 2,2-bis(3-allyl-4-hydroxyphenyl)propane, 1,1,1,3,3,3-hexafluoro-2,2-bis(3-allyl-4-hydroxyphenyl)propane, bis(3-allyl-4-hydroxyphenyl) sulfone, bis(3-allyl-4-hydroxyphenyl) sulfide, or bis(3-allyl-4-hydroxyphenyl) ether is preferable.

In the present embodiment, the content of the crosslinking agent is not particularly limited and is preferably 0.1 to 100 parts by mass based on 100 parts by mass of the film forming material for lithography, more preferably 5 to 50 parts by mass, and still more preferably 10 to 40 parts by mass. By setting the content of the crosslinking agent to the above range, occurrence of a mixing event with a resist layer tends to be prevented. Also, an antireflection effect is enhanced, and film formability after crosslinking tends to be enhanced.

[Crosslinking Promoting Agent]

The underlayer film forming composition for lithography of the present embodiment may contain a crosslinking promoting agent for accelerating crosslinking reaction (curing reaction), if required. Examples of the crosslinking promoting agent include a radical polymerization initiator.

The radical polymerization initiator may be a photopolymerization initiator that initiates radical polymerization by light, or may be a thermal polymerization initiator that initiates radical polymerization by heat. Examples of the radical polymerization initiator include at least one selected from the group consisting of a ketone-based photopolymerization initiator, an organic peroxide-based polymerization initiator and an azo-based polymerization initiator.

Examples of such a radical polymerization initiator include, without particular limitations, a ketone-based photopolymerization initiator such as 1-hydroxy cyclohexyl phenyl ketone, benzyl dimethyl ketal, 2-hydroxy-2-methyl-1-phenylpropan-1-one, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methylpropan-1-one, 2,4,6-trimethylbenzoyl-diphenylphosphine oxide, and bis(2,4,6-trimethylbenzoyl)-phenylphosphine oxide; and an organic peroxide-based polymerization initiator such as methyl ethyl ketone peroxide, cyclohexanone peroxide, methylcyclohexanone peroxide, methyl acetoacetate peroxide, acetyl acetate peroxide, 1,1-bis(t-hexylperoxy)-3,3,5-trimethylcyclohexane, 1,1-bis (t-hexylperoxy)-cyclohexane, 1,1-bis(t-butylperoxy)-3,3,5-trimethylcyclohexane, 1,1-bis(t-butylperoxy)-2-methylcyclohexane, 1,1-bis(t-butylperoxy)-cyclohexane, 1,1-bis(t- butylperoxy)cyclododecane, 1,1-bis(t-butylperoxy)butane, 2,2-bis(4,4-di-t-butylperoxycyclohexyl)propane, p-menthane hydroperoxide, diisopropylbenzene hydroperoxide, 1,1,3,3-tetramethylbutyl hydroperoxide, cumene hydroperoxide, t-hexyl hydroperoxide, t-butyl hydroperoxide, α,α'-bis(t-butylperoxy)diisopropylbenzene, dicumyl peroxide, 2,5-dimethyl-2,5-bis(t-butylperoxy)hexane, t-butylcumyl peroxide, di-t-butyl peroxide, 2,5-dimethyl-2,5-bis(t-butylperoxy)hexyne-3, isobutyryl peroxide, 3,5,5-trimethylhexanoyl peroxide, octanoyl peroxide, lauroyl peroxide, stearoyl peroxide, succinic acid peroxide, m-toluoyl benzoyl peroxide, benzoyl peroxide, di-n-propyl peroxydicarbonate, diisopropyl peroxydicarbonate, bis(4-t-butylcyclohexyl) peroxydicarbonate, di-2-ethoxyethyl peroxydicarbonate, di-2-ethoxyhexyl peroxydicarbonate, di-3-methoxybutyl peroxydicarbonate, di-s-butyl peroxydicarbonate, di(3-methyl-3-methoxybutyl) peroxydicarbonate, α,α'-bis(neodecanoylperoxy)diisopropylbenzene, cumyl peroxyneodecanoate, 1,1,3,3-tetramethylbutyl peroxyneodecanoate, 1-cyclohexyl-1-methylethyl peroxyneodecanoate, t-hexyl peroxyneodecanoate, t-butyl peroxyneodecanoate, t-hexyl peroxypivalate, t-butyl peroxypivalate, 1,1,3,3-tetramethylbutyl peroxy-2-ethylhexanoate, 2,5-dimethyl-2,5-bis(2-ethylhexanoylperoxy)hexanoate, 1-cyclohexyl-1-methylethyl peroxy-2-ethylhexanoate, t-hexyl peroxy-2-ethylhexanoate, t-butyl peroxy-2-ethylhexanoate, t-hexyl peroxyisopropylmonocarbonate, t-butyl peroxyisobutyrate, t-butyl peroxymalate, t-butyl peroxy-3,5,5-trimethylhexanoate, t-butyl peroxylaurate, t-butyl peroxyisopropylmonocarbonate, t-butyl peroxy-2-ethylhexylmonocarbonate, t-butyl peroxyacetate, t-butyl peroxy-m-toluylbenzoate, t-butyl peroxybenzoate, bis(t-butylperoxy) isophthalate, 2,5-dimethyl-2,5-bis(n-toluylperoxy)hexane, t-hexyl peroxybenzoate, 2,5-dimethyl-2,5-bis(benzoylperoxy)hexane, t-butyl peroxyallylmonocarbonate, t-butyltrimethylsilyl peroxide, 3,3',4,4'-tetra(t-butylperoxycarbonyl)benzophenone, and 2,3-dimethyl-2,3-diphenylbutane.

Further examples thereof include an azo-based polymerization initiator such as 2-phenylazo-4-methoxy-2,4-dimethylvaleronitrile, 1-[(1-cyano-1-methylethyl)azo]formamide, 1,1'-azobis(cyclohexane-1-carbonitrile), 2,2'-azobis(2-methylbutyronitrile), 2,2'-azobisisobutyronitrile, 2,2'-azobis(2,4-dimethylvaleronitrile), 2,2'-azobis(2-methylpropionamidine) dihydrochloride, 2,2'-azobis(2-methyl-N-phenylpropionamidine) dihydrochloride, 2,2'-azobis[N-(4-chlorophenyl)-2-methylpropionamide]dihydride chloride, 2,2'-azobis[N-(4-hydrophenyl)-2-methylpropionamidine] dihydrochloride, 2,2'-azobis[2-methyl-N-(phenylmethyl) propionamidine]dihydrochloride, 2,2'-azobis[2-methyl-N-(2-propenyl)propionamidine] dihydrochloride, 2,2'-azobis[N-(2-hydroxyethyl)-2-methylpropionamidine] dihydrochloride, 2,2'-azobis[2-(5-methyl-2-imidazolin-2-yl)propane]dihydrochloride, 2,2'-azobis[2-(2-imidazolin-2-yl)propane] dihydrochloride, 2,2'-azobis[2-(4,5,6,7-tetrahydro-1H-1,3-diazepin-2-yl)propane] dihydrochloride, 2,2'-azobis[2-(3,4,5,6-tetrahydropyrimidin-2-yl)propane] dihydrochloride, 2,2'-azobis[2-(5-hydroxy-3,4,5,6-tetrahydropyrimidin-2-yl)propane] dihydrochloride, 2,2'-azobis[2-[1-(2-hydroxyethyl)-2-imidazolin-2-yl]propane] dihydrochloride, 2,2'-azobis[2-(2-imidazolin-2-yl)propane], 2,2'-azobis[2-methyl-N-[1,1-bis(hydroxymethyl)-2-hydroxyethyl]propionamide], 2,2'-azobis[2-methyl-N-[1,1-bis (hydroxymethyl)ethyl]propionamide], 2,2'-azobis[2-methyl-N-(2-hydroxyethyl)propionamide], 2,2'-azobis(2-methylpropionamide), 2,2'-azobis(2,4,4-trimethylpentane), 2,2'-azobis(2-methylpropane), dimethyl-2,2-azobis(2-methylpropionate), 4,4'-azobis(4-cyanopentanoic acid), and 2,2'-azobis[2-(hydroxymethyl)propionitrile].

These radical polymerization initiators are used alone as one kind or in combination of two or more kinds.

[Acid Generating Agent]

The underlayer film forming composition for lithography of the present embodiment may contain an acid generating agent from the viewpoint of, for example, further accelerating crosslinking reaction by heat. An acid generating agent that generates an acid by thermal decomposition, an acid generating agent that generates an acid by light irradiation, and the like are known, any of which can be used. For example, an acid generating agent described in International Publication No. WO 2013/024779 can be used.

The content of the acid generating agent in the film forming composition for lithography is not particularly limited and is preferably 0.1 to 50 parts by mass, and more preferably 0.5 to 40 parts by mass, based on 100 parts by mass of the film forming material for lithography. By setting the content of the acid generating agent to the above range, crosslinking reaction tends to be enhanced and occurrence of a mixing event with a resist layer tends to be prevented.

[Basic Compound]

The underlayer film forming composition for lithography of the present embodiment may also contain a basic compound from the viewpoint of, for example, improving storage stability.

The basic compound plays a role to prevent crosslinking reaction from proceeding due to a trace amount of an acid generated from the acid generating agent, that is, a role as a quencher against the acid. Examples of such a basic compound include, but not particularly limited to, those described in International Publication No. WO 2013/024779.

The content of the basic compound in the underlayer film forming composition for lithography of the present embodiment is not particularly limited and is preferably 0.001 to 2 parts by mass, and more preferably 0.01 to 1 part by mass, based on 100 parts by mass of the film forming material for lithography. By setting the content of the basic compound to the above range, storage stability tends to be enhanced without excessively deteriorating crosslinking reaction.

[Further Additive Agent]

The underlayer film forming composition for lithography of the present embodiment may also contain an additional resin and/or compound for the purpose of conferring thermosetting or light curing properties or controlling absorbance. Examples of such an additional resin and/or compound include, without particular limitations, a naphthol resin, a xylene resin naphthol-modified resin, a phenol-modified resin of a naphthalene resin; a polyhydroxystyrene, a dicyclopentadiene resin, a resin containing (meth)acrylate, dimethacrylate, trimethacrylate, tetramethacrylate, a naphthalene ring such as vinylnaphthalene or polyacenaphthylene, a biphenyl ring such as phenanthrenequinone or fluorene, or a heterocyclic ring having a heteroatom such as thiophene or indene, and a resin containing no aromatic ring; and a resin or compound containing an alicyclic structure, such as a rosin-based resin, a cyclodextrin, an adamantine (poly)ol, a tricyclodecane(poly)ol, and a derivative thereof. The underlayer film forming composition for lithography of the present embodiment may also contain a publicly known additive agent. Examples of the publicly known additive agent include, but not limited to, a thermal and/or light curing catalyst, a polymerization inhibitor, a flame retardant, a filler, a coupling agent, a thermosetting resin, a light curable resin, a dye, a pigment, a thickener, a lubricant, an antifoaming agent, a leveling agent, an ultraviolet absorber, a surfactant, a colorant, and a nonionic surfactant.

[Underlayer Film for Lithography]

The underlayer film for lithography of the present embodiment is formed from the film forming composition for lithography of the present embodiment. The formation method is not particularly limited and a publicly known method can be applied. The underlayer film can be formed by, for example, applying the film forming composition for lithography of the present embodiment onto a substrate by a publicly known coating method or printing method such as spin coating or screen printing, and then removing an organic solvent by volatilization or the like.

It is preferable to perform baking in the formation of the underlayer film, for preventing occurrence of a mixing event with a resist upper layer film while accelerating crosslinking reaction. In this case, the baking temperature is not particularly limited and is preferably in the range of 80 to 450° C., and more preferably 200 to 400° C. The baking time is not particularly limited and is preferably in the range of 10 to 300 seconds. The thickness of the underlayer film can be arbitrarily selected according to required performance and is not particularly limited, but is preferably 30 to 20,000 nm, and more preferably 50 to 15,000 nm.

After preparing the underlayer film, it is preferable to prepare a silicon-containing resist layer or a single-layer resist made of hydrocarbon on the underlayer film in the case of a two-layer process, and to prepare a silicon-containing intermediate layer on the underlayer film and further prepare a silicon-free single-layer resist layer on the silicon-containing intermediate layer in the case of a three-layer process. In this case, a publicly known photoresist material can be used for forming this resist layer.

For the silicon-containing resist material for a two-layer process, a silicon atom-containing polymer such as a polysilsesquioxane derivative or a vinylsilane derivative is used as a base polymer, and a positive type photoresist material further containing an organic solvent, an acid generating agent, and if required, a basic compound or the like is preferably used, from the viewpoint of oxygen gas etching resistance. Here, a publicly known polymer that is used in this kind of resist material can be used as the silicon atom-containing polymer.

A polysilsesquioxane-based intermediate layer is preferably used as the silicon-containing intermediate layer for a three-layer process. By imparting effects as an antireflection film to the intermediate layer, there is a tendency that reflection can be effectively suppressed. For example, use of a material containing a large amount of an aromatic group and having high substrate etching resistance as the underlayer film in a process for exposure at 193 nm tends to increase a k value and enhance substrate reflection. However, the intermediate layer suppresses the reflection so that the substrate reflection can be 0.5% or less. The intermediate layer having such an antireflection effect is not limited, and polysilsesquioxane that crosslinks by an acid or heat in which a light absorbing group having a phenyl group or a silicon-silicon bond is introduced is preferably used for exposure at 193 nm.

Alternatively, an intermediate layer formed by chemical vapour deposition (CVD) may be used. The intermediate layer highly effective as an antireflection film prepared by CVD is not limited, and, for example, a SiON film is known. In general, the formation of an intermediate layer by a wet process such as spin coating or screen printing is more convenient and more advantageous in cost than CVD. The upper layer resist for a three-layer process may be positive type or negative type, and the same as a single-layer resist generally used can be used.

The underlayer film according to the present embodiment can also be used as an antireflection film for usual single-layer resists or an underlying material for suppression of pattern collapse. The underlayer film is excellent in etching resistance for an underlying process and can be expected to also function as a hard mask for an underlying process.

In the case of forming a resist layer from the above photoresist material, a wet process such as spin coating or screen printing is preferably used, as in the case of forming the above underlayer film. After coating with the resist material by spin coating or the like, prebaking is generally performed. This prebaking is preferably performed at 80 to 180° C. in the range of 10 to 300 seconds. Then, exposure, post-exposure baking (PEB), and development can be performed according to a conventional method to obtain a resist pattern. The thickness of the resist film is not particularly limited, and in general, is preferably 30 to 500 nm and more preferably 50 to 400 nm.

The exposure light can be arbitrarily selected and used according to the photoresist material to be used. General examples thereof can include a high energy ray having a wavelength of 300 nm or less, specifically, excimer laser of 248 nm, 193 nm, or 157 nm, soft x-ray of 3 to 20 nm, electron beam, and X-ray.

In a resist pattern formed by the above method, pattern collapse is suppressed by the underlayer film. Therefore, use of the underlayer film according to the present embodiment can produce a finer pattern and can reduce an exposure amount necessary for obtaining the resist pattern.

Next, etching is performed with the obtained resist pattern as a mask. Gas etching is preferably used as the etching of the underlayer film in a two-layer process. The gas etching is suitably etching using oxygen gas. In addition to oxygen gas, an inert gas such as He or Ar, or $CO$, $CO_2$, $NH_3$, $SO_2$, $N_2$, $NO_2$, or $H_2$ gas may be added. Alternatively, the gas etching may be performed with $CO$, $CO_2$, $NH_3$, $N_2$, $NO_2$, or $H_2$ gas without the use of oxygen gas. Particularly, the latter gas is preferably used for side wall protection in order to prevent the undercut of pattern side walls.

On the other hand, gas etching is also preferably used as the etching of the intermediate layer in a three-layer process. The same gas etching as described in the above two-layer process is applicable. Particularly, it is preferable to process the intermediate layer in a three-layer process by using chlorofluorocarbon-based gas and using the resist pattern as a mask. Then, as mentioned above, for example, the underlayer film can be processed by oxygen gas etching with the intermediate layer pattern as a mask.

Here, in the case of forming an inorganic hard mask intermediate layer film as the intermediate layer, a silicon oxide film, a silicon nitride film, or a silicon oxynitride film (SiON film) is formed by CVD, ALD, or the like. A method for forming the nitride film is not limited, and for example, a method described in Japanese Patent Laid-Open No. 2002-334869 (Patent Literature 9) or WO 2004/066377 (Patent Literature 10) can be used. Although a photoresist film can be formed directly on such an intermediate layer film, an organic antireflection film (BARC) may be formed on the intermediate layer film by spin coating and a photoresist film may be formed thereon.

A polysilsesquioxane-based intermediate layer is suitably used as the intermediate layer. By imparting effects as an antireflection film to the resist intermediate layer film, there is a tendency that reflection can be effectively suppressed. A specific material for the polysilsesquioxane-based intermediate layer is not limited, and, for example, a material described in Japanese Patent Laid-Open No. 2007-226170 (Patent Literature 11) or Japanese Patent Laid-Open No. 2007-226204 (Patent Literature 12) can be used.

The subsequent etching of the substrate can also be performed by a conventional method. For example, the substrate made of $SiO_2$ or SiN can be etched mainly using chlorofluorocarbon-based gas, and the substrate made of p-Si, Al, or W can be etched mainly using chlorine- or bromine-based gas. In the case of etching the substrate with chlorofluorocarbon-based gas, the silicon-containing resist of the two-layer resist process or the silicon-containing intermediate layer of the three-layer process is stripped at the same time with substrate processing. On the other hand, in the case of etching the substrate with chlorine- or bromine-based gas, the silicon-containing resist layer or the silicon-containing intermediate layer is separately stripped and in general, stripped by dry etching using chlorofluorocarbon-based gas after substrate processing.

A feature of the underlayer film of the present embodiment is that it is excellent in etching resistance of the substrates. The substrate can be arbitrarily selected for use from publicly known ones and is not particularly limited. Examples thereof include Si, α-Si, p-Si, $SiO_2$, SiN, SiON, W, TiN, and Al. The substrate may be a laminate having a film to be processed (substrate to be processed) on a base material (support). Examples of such a film to be processed include various low-k films such as Si, $SiO_2$, SiON, SiN, p-Si, α-Si, W, W—Si, Al, Cu, and Al—Si, and stopper films thereof. A material different from that for the base material (support) is generally used. The thickness of the substrate to be processed or the film to be processed is not particularly limited and is generally preferably about 50 to 1,000,000 nm, and more preferably 75 to 50,000 nm.

[Resist Pattern Formation Method]

The resist pattern formation method of the present embodiment comprises: an underlayer film formation step of forming an underlayer film on a substrate using the composition of the present embodiment; a photoresist layer formation step of forming at least one photoresist layer on the underlayer film formed through the underlayer film formation step; and a step of irradiating a predetermined region of the photoresist layer formed through the photoresist layer formation step with radiation for development. The resist pattern formation method of the present embodiment can be used for forming various patterns, and is preferably a method for forming an insulating film pattern.

[Circuit Pattern Formation Method]

The circuit pattern formation method of the present embodiment comprises: an underlayer film formation step of forming an underlayer film on a substrate using the composition of the present embodiment; an intermediate layer film formation step of forming an intermediate layer film on the underlayer film formed through the underlayer film formation step; a photoresist layer formation step of forming at least one photoresist layer on the intermediate layer film formed through the intermediate layer film formation step; a resist pattern formation step of irradiating a predetermined region of the photoresist layer formed through the photoresist layer formation step with radiation for development, thereby forming a resist pattern; an intermediate layer film pattern formation step of etching the intermediate layer film with the resist pattern formed through the resist pattern formation step as a mask, thereby forming an intermediate layer film pattern; an underlayer film pattern formation step of etching the underlayer film with the intermediate layer film pattern formed through the intermediate layer film pattern formation step as a mask, thereby forming an underlayer film pattern; and a substrate pattern formation step of etching the substrate with the underlayer film pattern formed through the underlayer film pattern formation step as a mask, thereby forming a pattern on the substrate.

[Resist Permanent Film]

The resist permanent film of the present embodiment contains the composition of the present embodiment. The resist permanent film prepared by coating with the composition of the present embodiment is suitable as a permanent film that also remains in a final product, if required, after formation of a resist pattern. Specific examples of the permanent film include, in relation to semiconductor devices, a solder resist, a package material, an underfill material, a package adhesive layer for circuit elements and the like, and an adhesive layer between integrated circuit elements and circuit substrates, and in relation to thin displays, a thin film transistor protecting film, a liquid crystal color filter protecting film, a black matrix, and a spacer.

Particularly, the resist permanent film containing the composition of the present embodiment is excellent in heat resistance and humidity resistance and furthermore, also has the excellent advantage that contamination by sublimable components is reduced. Particularly, for a display material, a material that achieves all of high sensitivity, high heat resistance, and hygroscopic reliability with reduced deterioration in image quality due to significant contamination can be obtained.

In the case of using the composition of the present embodiment for resist permanent film purposes, a curing agent as well as, if required, various additive agents such as an additional resin, a surfactant, a dye, a filler, a crosslinking agent, and a dissolution promoting agent can be added and dissolved in an organic solvent to prepare a composition for resist permanent films.

The composition of the present embodiment can be prepared by adding each of the above components and mixing them using a stirrer or the like. When the composition of the present embodiment contains a filler or a pigment, it can be prepared by dispersion or mixing using a dispersion apparatus such as a dissolver, a homogenizer, and a three-roll mill.

[Method for Purifying Compound or Resin]

The method for purifying the compound or the resin of the present embodiment comprises: an extraction step of bringing a solution containing the compound or the resin of the present embodiment and an organic solvent that does not inadvertently mix with water into contact with an acidic aqueous solution, thereby carrying out extraction. More specifically, in the purification method of the present embodiment, the compound or the resin of the present embodiment is dissolved in an organic solvent that does not inadvertently mix with water; the resultant solution is brought into contact with an acidic aqueous solution to carry out an extraction treatment, thereby transferring metals contained in the solution (A) containing the compound or the resin of the present embodiment and the organic solvent to the aqueous phase; and then the organic phase and the aqueous phase are separated and purified. Through the purification method of the present embodiment, the content of various metals in the compound or the resin of the present embodiment can be significantly reduced.

In the present embodiment, the "organic solvent that does not inadvertently mix with water" means that the solubility is less than 50% by mass in water at 20 to 90° C., and preferably less than 25% by mass from the viewpoint of productivity. The organic solvent that does not inadvertently mix with water is not particularly limited, but is preferably an organic solvent that is safely applicable to semiconductor manufacturing processes. Normally, the amount of the organic solvent used is approximately 1 to 100 times by weight relative to the compound or the resin of the present embodiment.

Specific examples of the solvent to be used include those described in International Publication No. WO 2015/080240. These solvents are used alone as one kind or in combination of two or more kinds. Among them, toluene, 2-heptanone, cyclohexanone, cyclopentanone, methyl isobutyl ketone, propylene glycol monomethyl ether acetate, ethyl acetate, and the like are preferable, and cyclohexanone and propylene glycol monomethyl ether acetate are particularly preferable.

The acidic aqueous solution to be used is appropriately selected from aqueous solutions in which generally known organic or inorganic compounds are dissolved in water. Examples thereof also include those described in International Publication No. WO 2015/080240. These acidic aqueous solutions are used alone as one kind or in combination of two or more kinds. Among them, an aqueous solution of sulfuric acid, nitric acid, and a carboxylic acid such as acetic acid, oxalic acid, tartaric acid and citric acid are preferable; an aqueous solution of sulfuric acid, oxalic acid, tartaric acid and citric acid are still more preferable; and an aqueous solution of oxalic acid is particularly preferable. It is considered that a polyvalent carboxylic acid such as oxalic acid, tartaric acid and citric acid coordinates with metal ions and provides a chelating effect, and thus is capable of removing more metals. In addition, as the water used herein, water, the metal content of which is small, such as ion exchanged water, is suitably used according to the purpose of the present invention.

The pH of the acidic aqueous solution to be used in the present embodiment is not particularly limited, but when the acidity of the aqueous solution is too high, it may have a negative influence on the compound represented by the formula (1) or the resin obtained using the compound as a monomer, which is not preferable. Normally, the pH range is about 0 to 5, and is more preferably about pH 0 to 3.

The amount of the acidic aqueous solution to be used in the present embodiment is not particularly limited, but when the amount is too small, it is required to increase the number of extraction treatments for removing metals, and on the other hand, when the amount of the aqueous solution is too large, the entire fluid volume becomes large, which may cause operational problems. The amount of the aqueous solution used is usually 10 to 200% by mass, and preferably 20 to 100% by mass, based on the solution of the compound or the resin of the present embodiment dissolved in an organic solvent.

In the present embodiment, for example, by bringing the acidic aqueous solution as described above into contact with the solution (A) containing the compound or the resin of the present embodiment and the organic solvent that does not inadvertently mix with water, metals are extracted.

The temperature when extraction treatment is carried out is generally in the range of 20 to 90° C., and preferably 30 to 80° C. The extraction operation is carried out, for example, by thoroughly mixing the solution (S) and the acidic aqueous solution by stirring or the like and then leaving the obtained mixed solution to stand still. Thereby, metals contained in the solution containing the compound or the resin of the present embodiment and the organic solvent are transferred to the aqueous phase. Also, by this operation, the acidity of the solution is lowered, and the degradation of the compound or the resin of the present embodiment can be suppressed.

The obtained mixture is separated into an aqueous phase and a solution phase containing the compound or the resin of the present embodiment and the organic solvent, and thus the solution containing the compound or the resin of the present embodiment and the organic solvent is recovered by decantation or the like. The time for leaving the mixed solution to stand still is not particularly limited, but when the time for leaving the mixed solution to stand still is too short, separation of the solution phase containing the organic solvent and the aqueous phase becomes poor, which is not preferable. Normally, the time for leaving the mixed solution to stand still is 1 minute or longer, more preferably 10 minutes or longer, and still more preferably 30 minutes or longer. While the extraction treatment may be carried out only once, it is also effective to repeat mixing, leaving-to-stand-still, and separating operations multiple times.

When such an extraction treatment is carried out using the acidic aqueous solution, after the treatment, it is preferable to further subject the recovered solution (A), which has been extracted from the aqueous solution and contains the compound or the resin of the present embodiment and the organic solvent, to an extraction treatment with water. The extraction operation is carried out by thoroughly mixing the solution (A) and water by stirring or the like and then leaving the obtained mixed solution to stand still. The resultant solution is separated into an aqueous phase and a solution phase containing the compound or the resin of the present embodiment and the organic solvent, and thus the solution phase containing the compound or the resin of the present embodiment and the organic solvent is recovered by decantation or the like. In addition, as the water used herein, water, the metal content of which is small, such as ion exchanged water, is preferable according to the purpose of the present invention. While the extraction treatment may be carried out only once, it is also effective to repeat mixing, leaving-to-stand-still, and separating operations multiple times. The proportions of both used in the extraction treatment and the temperature, time, and other conditions are not particularly limited, and may be the same as those of the previous contact treatment with the acidic aqueous solution.

Water that is present in the thus-obtained solution containing the compound or the resin of the present embodiment and the organic solvent can be easily removed by performing vacuum distillation or a like operation. Also, if required, the concentration of the compound or the resin of the present embodiment can be regulated to be any concentration by adding an organic solvent.

For the method for obtaining the compound or the resin of the present embodiment alone from the obtained solution containing the compound or the resin of the present embodiment and the organic solvent, a publicly known method can be carried out, such as reduced-pressure removal, separation by reprecipitation, and a combination thereof. A publicly known treatment such as concentration operation, filtration operation, centrifugation operation and drying operation can be carried out, if required.

EXAMPLES

The present embodiment will be described in more detail with reference to synthesis examples and examples below. However, the present embodiment is not limited to these examples by any means.

(Carbon Concentration and Oxygen Concentration)

The carbon concentration and the oxygen concentration (% by mass) of the compound or the resin were measured by organic elemental analysis by using a product manufactured by Yaic. Yanaco, "CHN Coder MT-6".

(Nmr Measurement)

$^1$H-NMR measurement was carried out under the following conditions by using "Advance 60011 spectrometer" manufactured by Bruker Corp.

Frequency: 400 MHz
Solvent: d6-DMSO
Internal standard: TMS
Measurement temperature: 23° C.

(Molecular Weight)

The molecular weight of the compound or the resin was measured through LC-MS analysis by using a product manufactured by Waters Corp., "Acquity UPLC/MALDI-Synapt HDMS".

(Evaluation of Solubility)

At 23° C., the compound or the resin was dissolved in propylene glycol monomethyl ether (PGME) to form a 5 mass % solution. Subsequently, the solubility after leaving the solution to stand still at 5° C. for 30 days was evaluated according to the following criteria.

Evaluation A: no precipitate was visually confirmed
Evaluation C: precipitates were visually confirmed (Evaluation of Heat Resistance)

EXSTAR 6000 TG/DTA apparatus manufactured by SII NanoTechnology Inc. was used. About 5 mg of a sample was placed in an unsealed container made of aluminum, and the temperature was raised to 500° C. at a temperature increase rate of 10° C./min in a nitrogen gas stream (30 m$^1$/min). The temperature at which a decrease in baseline appeared was defined as the thermal decomposition temperature (Tg) The heat resistance was evaluated according to the following criteria.

Evaluation A: The thermal decomposition temperature was ≥150° C.
Evaluation C: The thermal decomposition temperature was <150° C.

(Synthesis Working Example 1) Synthesis of BiP-1

To a container (internal capacity: 300 mL) equipped with a stirrer, a condenser tube, and a burette, 10 g of 4,4'-bisphenol ether (a reagent manufactured by Sigma-Aldrich), 0.3 g of sulfuric acid, 3.0 g of 4-biphenylaldehyde (a product manufactured by Mitsubishi Gas Chemical Company, Inc.), 10 g of 1-methoxy-2-propanol were added, and the contents were reacted by being stirred at 90° C. for 6 hours to obtain a reaction liquid. The reaction liquid was cooled, and insoluble matter was filtered off. 10 g of 1-methoxy-2-propanol was added, and the reaction product was then crystallized by hexane and recovered by filtration. The recovered product was dissolved in 100 mL of ethyl acetate (manufactured by Kanto Chemical Co., Inc.) and 50 mL of pure water was added thereto, followed by extraction with ethyl acetate. Next, the mixture was separated until neutral by the addition of pure water, and then dehydrated and concentrated to obtain a solution. The obtained solution was separated by column chromatography to obtain 1.0 g of the objective compound (BiP-1) represented by the following formula (BiP-1).

As a result of measuring the molecular weight of the obtained compound (BiP-1) by the above method, it was 568. In addition, the carbon concentration of the obtained compound (BiP-1) was 78.2% by mass, and the oxygen concentration thereof was 16.9% by mass.

The following peaks were found by $^1$H-NMR (500 MHz, DMSO-d$_6$) measurement performed on the obtained compound (BiP-1), and the compound was confirmed to have a chemical structure of the following formula (BiP-1). δ (ppm): 9.18 (4H, O—H), 6.60-7.62 (23H, Ph-H), 6.01 (1H, C—H)

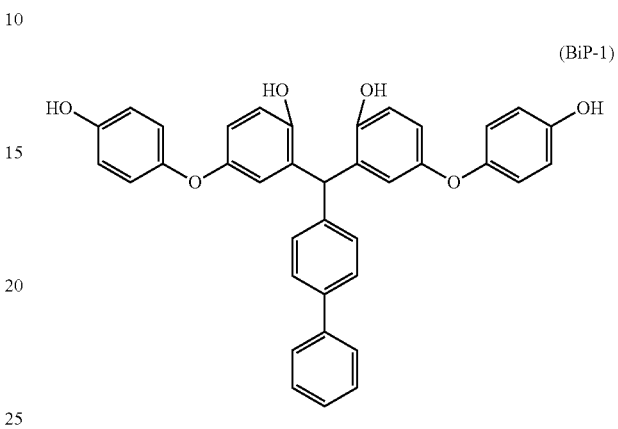

(BiP-1)

(Synthesis Working Example 2) Synthesis of BiP-2

In the same reaction as in Synthesis Working Example 1 except that 4,4'-thiobisphenol was used instead of 4,4'-bisphenol ether, 0.5 g of the objective compound (BiP-2) represented by the following formula (BiP-2) was obtained.

As a result of measuring the molecular weight of the obtained compound (BiP-2) by the above method, it was 600. In addition, the carbon concentration of the obtained compound (BiP-2) was 73.4% by mass, and the oxygen concentration thereof was 10.7% by mass.

The following peaks were found by $^1$H-NMR (500 MHz, DMSO-d$_6$) measurement performed on the obtained compound (BiP-2), and the compound was confirmed to have a chemical structure of the following formula (BiP-2). δ (ppm): 9.18 (4H, O—H), 6.61-7.75 (23H, Ph-H), 6.01 (1H, C—H)

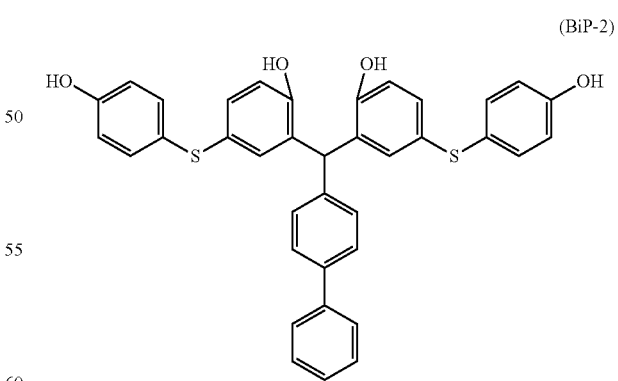

(BiP-2)

(Synthesis Working Example 3) Synthesis of RBiP-1

In the same reaction as in Synthesis Working Example 1 except that BiP-1 obtained in Synthesis Working Example 1 was used instead of 4,4′-bisphenol ether, 10.0 g of the objective resin (RBiP-1) represented by the following formula (RBiP-1) was obtained.

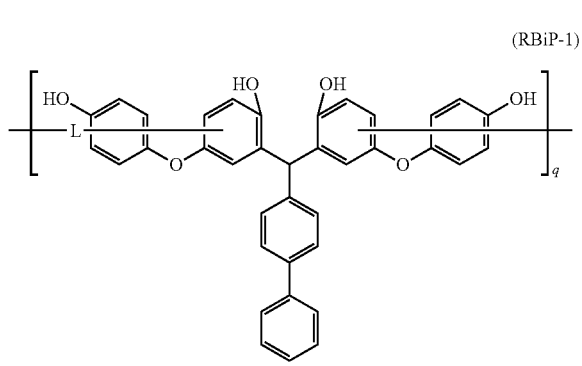

(RBiP-1)

(In the formula (RBiP-1), L represents a residue derived from 4-biphenylaldehyde and q represents the number of repeat units.)

(Synthesis Working Example 4) Synthesis of RBiP-2

In the same reaction as in Synthesis Working Example 2 except that Bip-2 obtained in Synthesis Working Example 2 was used instead of 4,4′-bisphenol ether, 8.0 g of the objective resin (RBiP-2) represented by the following formula (RBiP-2) was obtained.

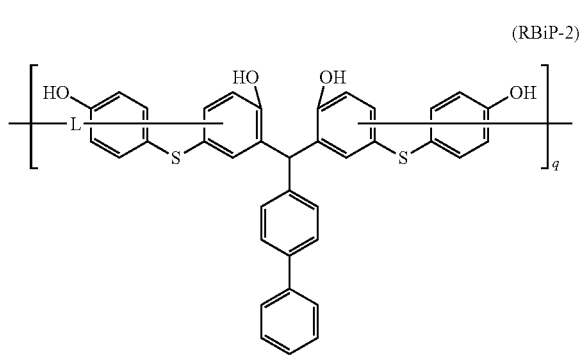

(RBiP-2)

(In the formula (RBiP-2), L represents a residue derived from 4-biphenylaldehyde and q represents the number of repeat units.)

(Synthesis Working Example 5) Synthesis of BiP-3

In the same reaction as in Synthesis Working Example 1 except that bis(4-hydroxyphenyl)sulfone was used instead of 4,4′-bisphenol ether, 1.2 g of the objective compound (BiP-3) represented by the following formula (BiP-3) was obtained.

As a result of measuring the molecular weight of the obtained compound (BiP-3) by the above method, it was 665. In addition, the carbon concentration of the obtained compound (BiP-3) was 66.9% by mass, and the oxygen concentration thereof was 19.2% by mass.

The following peaks were found by $^1$H-NMR (500 MHz, DMSO-$d_6$) measurement performed on the obtained compound (BiP-3), and the compound was confirmed to have a chemical structure of the following formula (BiP-3). δ (ppm): 9.32 (4H, O—H), 6.71-7.95 (23H, Ph-H), 6.15 (1H, C—H)

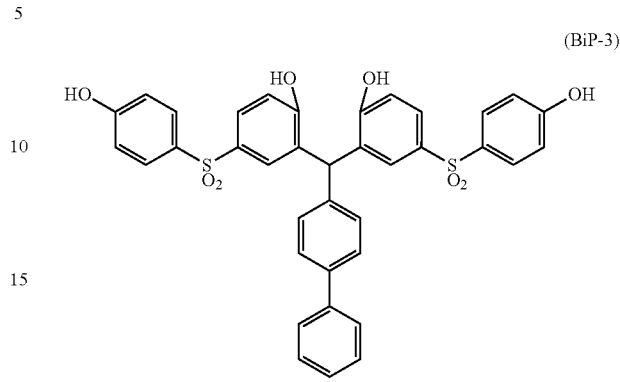

(BiP-3)

(Synthesis Working Example 6) Synthesis of RBiP-3

In the same reaction as in Synthesis Working Example 2 except that Bip-3 obtained in Synthesis Working Example 5 was used instead of 4,4′-bisphenol ether, 8.0 g of the objective resin (RBiP-3) represented by the following formula (RBiP-3) was obtained.

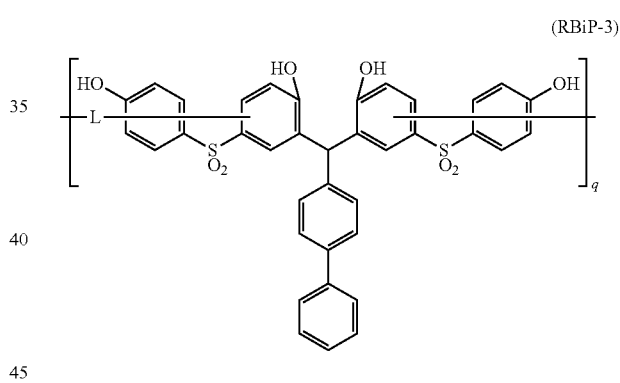

(RBiP-3)

(In the formula (RBiP-3), L represents a residue derived from 4-biphenylaldehyde and q represents the number of repeat units.)

(Synthesis Working Example 7) Synthesis of BiP-4

In the same reaction as in Synthesis Working Example 1 except that benzaldehyde was used instead of 4-biphenylaldehyde, 1.6 g of the objective compound (BiP-4) represented by the following formula (BiP-4) was obtained.

As a result of measuring the molecular weight of the obtained compound (BiP-4) by the above method, it was 492. In addition, the carbon concentration of the obtained compound (BiP-4) was 75.6% by mass, and the oxygen concentration thereof was 19.5% by mass.

The following peaks were found by $^1$H-NMR (500 MHz, DMSO-$d_6$) measurement performed on the obtained compound (BiP-4), and the compound was confirmed to have a chemical structure of the following formula (BiP-4). δ (ppm): 9.18 (4H, O—H), 6.61-7.46 (19H, Ph-H), 6.03 (1H, C—H)

(BiP-4)

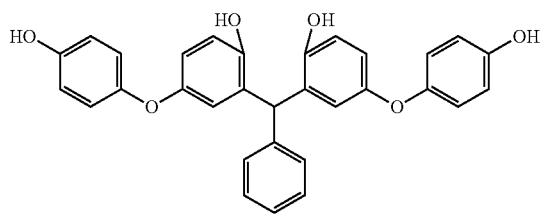

(Synthesis Working Example 8) Synthesis of RBiP-4

In the same reaction as in Synthesis Working Example 2 except that Bip-4 obtained in Synthesis Working Example 7 was used instead of 4,4'-bisphenol ether, 8.0 g of the objective resin (RBiP-4) represented by the following formula (RBiP-4) was obtained.

(RBiP-4)

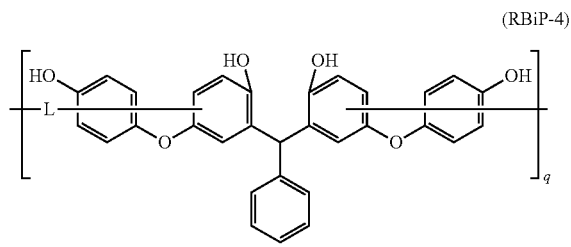

(In the formula (RBiP-4), L represents a residue derived from benzaldehyde and q represents the number of repeat units.)

(Synthesis Working Example 9) Synthesis of BiP-5

In the same reaction as in Synthesis Working Example 1 except that 2-naphthaldehyde was used instead of 4-biphenylaldehyde, 1.6 g of the objective compound (BiP-5) represented by the following formula (BiP-5) was obtained. As a result of measuring the molecular weight of the obtained compound (BiP-5) by the above method, it was 542. In addition, the carbon concentration of the obtained compound (BiP-5) was 77.5% by mass, and the oxygen concentration thereof was 17.7% by mass.

The following peaks were found by $^1$H-NMR (500 MHz, DMSO-$d_6$) measurement performed on the obtained compound (BiP-5), and the compound was confirmed to have a chemical structure of the following formula (BiP-5). δ (ppm): 9.18 (4H, O—H), 6.45-7.69 (21H, Ph-H), 6.08 (1H, C—H)

(BiP-5)

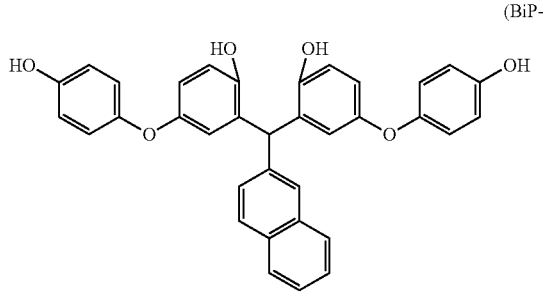

(Synthesis Working Example 10) Synthesis of RBiP-5

In the same reaction as in Synthesis Working Example 2 except that Bip-5 obtained in Synthesis Working Example 9 was used instead of 4,4'-bisphenol ether, 11.0 g of the objective resin (RBiP-5) represented by the following formula (RBiP-5) was obtained.

(RBiP-5)

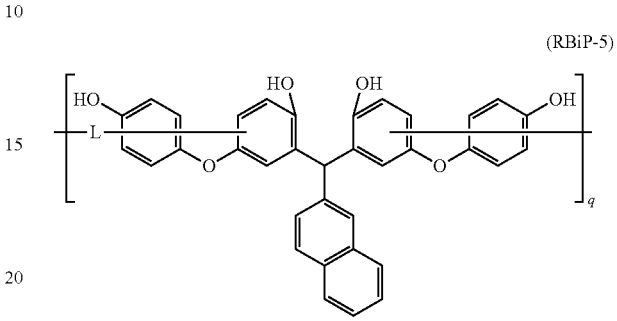

(In the formula (RBiP-5), L represents a residue derived from 2-naphthaldehyde and q represents the number of repeat units.)

(Synthesis Working Example 11) Synthesis of BiP-6

In the same reaction as in Synthesis Working Example 1 except that 2,2'-dimethylpropanal was used instead of 4-biphenylaldehyde, 0.5 g of the objective compound (BiP-6) represented by the following formula (BiP-6) was obtained.

As a result of measuring the molecular weight of the obtained compound (BiP-6) by the above method, it was 472. In addition, the carbon concentration of the obtained compound (BiP-6) was 73.7% by mass, and the oxygen concentration thereof was 20.3% by mass.

The following peaks were found by $^1$H-NMR (500 MHz, DMSO-$d_6$) measurement performed on the obtained compound (BiP-6), and the compound was confirmed to have a chemical structure of the following formula (BiP-6). δ (ppm): 9.04 (4H, O—H), 6.45-7.69 (21H, Ph-H), 5.98 (1H, C—H), 1.73-1.88 (9H, —C(CH3))

(BiP-6)

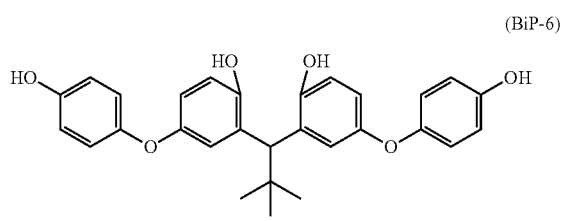 [SMILES: CC(C)(C)C(c1cc(Oc2ccc(O)cc2)ccc1O)c1cc(Oc2ccc(O)cc2)ccc1O]

(Synthesis Working Example 12) Synthesis of RBiP-6

In the same reaction as in Synthesis Working Example 2 except that Bip-6 obtained in Synthesis Working Example 11 was used instead of 4,4'-bisphenol ether, 5.5 g of the objective resin (RBiP-6) represented by the following formula (RBiP-6) was obtained.

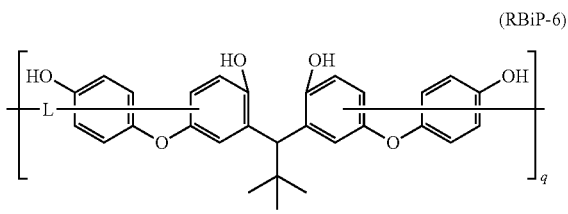

(RBiP-6)

(In the formula (RBiP-6), L represents a residue derived from 2,2'-dimethylpropanal and q represents the number of repeat units.)

Synthetic Example 1

A four necked flask (internal capacity: 10 L) equipped with a Dimroth condenser tube, a thermometer, and a stirring blade and having a detachable bottom was prepared. To this four necked flask, 1.09 kg (7 mol) of 1,5-dimethylnaphthalene (manufactured by Mitsubishi Gas Chemical Company, Inc.), 2.1 kg (28 mol as formaldehyde) of a 40 mass % aqueous formalin solution (manufactured by Mitsubishi Gas Chemical Company, Inc.), and 0.97 mL of a 98 mass % sulfuric acid (manufactured by Kanto Chemical Co., Inc.) were added in a nitrogen stream, and the mixture was reacted for 7 hours while refluxed at 100° C. at normal pressure. Subsequently, 1.8 kg of ethylbenzene (special grade reagent manufactured by Wako Pure Chemical Industries, Ltd.) was added as a diluting solvent to the reaction liquid, and the mixture was left to stand still, followed by removal of an aqueous phase as a lower phase. Neutralization and washing with water were further performed, and ethylbenzene and unreacted 1,5-dimethylnaphthalene were distilled off under reduced pressure to obtain 1.25 kg of a dimethylnaphthalene formaldehyde resin as a light brown solid. The molecular weight of the obtained dimethylnaphthalene formaldehyde was Mn: 562.

Then, a four necked flask (internal capacity: 0.5 L) equipped with a Dimroth condenser tube, a thermometer, and a stirring blade was prepared. To this four necked flask, 100 g (0.51 mol) of the dimethylnaphthalene formaldehyde resin obtained as described above, and 0.05 g of p-toluenesulfonic acid were added in a nitrogen stream, and the temperature was raised to 190° C. at which the mixture was then heated for 2 hours, followed by stirring. Subsequently, 52.0 g (0.36 mol) of 1-naphthol was further added thereto, the temperature was further elevated to 220° C., and the mixture was reacted for 2 hours. After dilution with a solvent, neutralization and washing with water were performed, and the solvent was distilled off under reduced pressure to obtain 126.1 g of a modified resin (CR-1) as a black-brown solid.

The obtained resin (CR-1) had Mn: 885, Mw: 2220, and Mw/Mn: 4.17. In addition, the carbon concentration of the obtained resin (CR-1) was 89.1% by mass, and the oxygen concentration thereof was 4.5% by mass. Note that the Mn, Mw and Mw/Mn of the resin (CR-1) were determined by gel permeation chromatography (GPC) analysis under the following measurement conditions in terms of polystyrene.

Apparatus: Shodex GPC-101 model (a product manufactured by Showa Denko K.K.)
Column: KF-80M x 3
Eluent: 1 mL/min THF
Temperature: 40° C.

Examples 1 to 14 and Comparative Example 1

For the above BiP-1 to BiP-6, RBiP-1 to RBiP-6 and CR-1, solubility test was carried out. The results are shown in Table 1. Also, underlayer film forming materials for lithography (underlayer film forming compositions for lithography) were each prepared according to the compositions shown in Table 1. Next, a silicon substrate was spin coated with each of these underlayer film forming materials for lithography, and then baked at 240° C. for 60 seconds and further at 400° C. for 120 seconds to prepare each underlayer film with a film thickness of 200 nm. The following acid generating agent, crosslinking agent, and organic solvent were used.

Acid generating agent: a product manufactured by Midori Kagaku Co., Ltd., "di-tertiary butyl diphenyliodonium nonafluoromethanesulfonate" (in the table, designated as "DTDPI")

Crosslinking agent: a product manufactured by Sanwa Chemical Co., Ltd., "NIKALAC MX270" (in the table, designated as "NIKALAC")

Organic solvent: Propylene glycol monomethyl ether acetate acetate (in the table, designated as "PGMEA")

For each of the obtained underlayer films, etching test was carried out under the following conditions to evaluate etching resistance. The evaluation results are shown in Table 1.

[Etching test]

Etching apparatus: a product manufactured by Samco International, Inc., "RIE-10NR"

Output: 50 W

Pressure: 20 Pa

Time: 2 min

Etching gas

Ar gas flow rate:$CF_4$ gas flow rate:$O_2$ gas flow rate=50:5:5 (sccm)

[Evaluation of Etching Resistance]

The evaluation of etching resistance was carried out by the following procedures.

First, an underlayer film containing a phenol novolac resin was prepared under the same conditions as in Example 1 except that a phenol novolac resin (PSM4357 manufactured by Gunei Chemical Industry Co., Ltd.) was used instead of the compound (BiP-1) used in Example 1. Then, the above etching test was carried out for this underlayer film containing a phenol novolac resin, and the etching rate (etching speed) was measured. Next, for each of the underlayer films of Examples and Comparative Example, the above etching test was carried out, and the etching rate was measured. Then, the etching resistance for each of Examples and Comparative Example was evaluated according to the following evaluation criteria on the basis of the etching rate of the underlayer film containing a phenol novolac resin.

[Evaluation Criteria]

Evaluation A: The etching rate was less than −10% as compared with the underlayer film of novolac.

Evaluation B: The etching rate was −10% to +5% as compared with the underlayer film of novolac.

Evaluation C: The etching rate was more than +5% as compared with the underlayer film of novolac.

TABLE 1

| | Compound or resin (parts by mass) | Solvent (parts by mass) | Acid generating agent (parts by mass) | Crosslinking agent (parts by mass) | Evaluation of solubility | Evaluation of etching resistance |
|---|---|---|---|---|---|---|
| Example 1 | BiP-1 (10) | PGMEA (90) | — | — | A | A |
| Example 2 | BiP-1 (10) | PGMEA (90) | DTDPI (0.5) | NIKALAC (0.5) | A | A |
| Example 3 | RBiP-1 (10) | PGMEA (90) | — | — | A | A |
| Example 4 | RBiP-1 (10) | PGMEA (90) | DTDPI (0.5) | NIKALAC (0.5) | A | A |
| Example 5 | BiP-2 (10) | PGMEA (90) | DTDPI (0.5) | NIKALAC (0.5) | A | A |
| Example 6 | RBiP-2 (10) | PGMEA (90) | DTDPI (0.5) | NIKALAC (0.5) | A | A |
| Example 7 | BiP-3 (10) | PGMEA (90) | DTDPI (0.5) | NIKALAC (0.5) | A | A |
| Example 8 | RBiP-3 (10) | PGMEA (90) | DTDPI (0.5) | NIKALAC (0.5) | A | A |
| Example 9 | BiP-4 (10) | PGMEA (90) | DTDPI (0.5) | NIKALAC (0.5) | A | A |
| Example 10 | RBiP-4 (10) | PGMEA (90) | DTDPI (0.5) | NIKALAC (0.5) | A | A |
| Example 11 | BiP-5 (10) | PGMEA (90) | DTDPI (0.5) | NIKALAC (0.5) | A | A |
| Example 12 | RBiP-5 (10) | PGMEA (90) | DTDPI (0.5) | NIKALAC (0.5) | A | A |
| Example 13 | BiP-6 (10) | PGMEA (90) | DTDPI (0.5) | NIKALAC (0.5) | A | A |
| Example 14 | RBiP-6 (10) | PGMEA (90) | DTDPI (0.5) | NIKALAC (0.5) | A | A |
| Comparative Example 1 | CR-1 (10) | PGMEA (90) | DTDPI (0.5) | NIKALAC (0.5) | A | C |

Examples 15 to 28

A SiO$_2$ substrate with a film thickness of 300 nm was coated with the solution of the underlayer film forming material for lithography prepared in each of the above Examples 1 to 14, and baked at 240° C. for 60 seconds and further at 400° C. for 120 seconds to form each underlayer film with a film thickness of 70 nm. This underlayer film was coated with a resist solution for ArF and baked at 130° C. for 60 seconds to form a photoresist layer with a film thickness of 140 nm. The ArF resist solution used was prepared by compounding 5 parts by mass of a compound represented by the formula (11) given below, 1 part by mass of triphenylsulfonium nonafluoromethanesulfonate, 2 parts by mass of tributylamine, and 92 parts by mass of PGMEA. For the compound represented by the formula (11) given below, 4.15 g of 2-methyl-2-methacryloyloxyadamantane, 3.00 g of methacryloyloxy-γ-butyrolactone, 2.08 g of 3-hydroxy-1-adamantyl methacrylate, and 0.38 g of azobisisobutyronitrile were dissolved in 80 mL of tetrahydrofuran to prepare a reaction solution. This reaction solution was polymerized for 22 hours with the reaction temperature kept at 63° C. in a nitrogen atmosphere. Then, the reaction solution was added dropwise into 400 mL of n-hexane. The product resin thus obtained was solidified and purified, and the resulting white powder was filtered and dried overnight at 40° C. under reduced pressure to obtain a compound represented by the following formula.

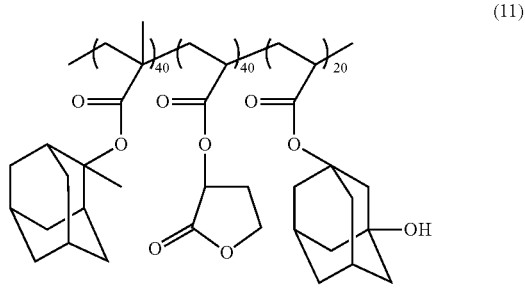

(11)

The numbers in the above formula (11) indicate the ratio of each constitutional unit.

Subsequently, the photoresist layer was exposed using an electron beam lithography system (manufactured by ELIONIX INC.; ELS-7500, 50 keV), baked (PEB) at 115° C. for 90 seconds, and developed for 60 seconds in a 2.38 mass % tetramethylammonium hydroxide (TMAH) aqueous solution to obtain a positive type resist pattern.

Defects of the obtained resist patterns of 55 nm L/S (1:1) and 80 nm L/S (1:1) were observed, and the results are shown in Table 2. In the table, "good" means that no major defects were found in the formed resist pattern, and "poor" means that major defects were found in the formed resist pattern.

Also, for the resolution, a value of the minimum line width (the finest pattern) where the resist pattern shape forms a good rectangle and no defects are seen, measured by using a scanning electron microscope (S-4800 manufactured by Hitachi High-Technologies), is given. The sensitivity indicates the exposure intensity upon giving the minimum line width, which means that the smaller the exposure intensity, the higher the sensitivity.

Comparative Example 2

The same operations as in Example 15 were performed except that no underlayer film was formed so that a photoresist layer was formed directly on a $SiO_2$ substrate to obtain a positive type resist pattern. The results are shown in Table 2.

TABLE 2

| | Underlayer film forming material | Resolution (nm L/S) | Sensitivity (μC/cm$^2$) | Resist pattern shape after development |
|---|---|---|---|---|
| Example 15 | Example 1 | 55 | 10 | Good |
| Example 16 | Example 2 | 55 | 10 | Good |
| Example 17 | Example 3 | 55 | 10 | Good |
| Example 18 | Example 4 | 55 | 10 | Good |
| Example 19 | Example 5 | 55 | 10 | Good |
| Example 20 | Example 6 | 55 | 10 | Good |
| Example 21 | Example 7 | 55 | 10 | Good |
| Example 22 | Example 8 | 55 | 10 | Good |
| Example 23 | Example 9 | 55 | 10 | Good |
| Example 24 | Example 10 | 55 | 10 | Good |
| Example 25 | Example 11 | 55 | 10 | Good |
| Example 26 | Example 12 | 55 | 10 | Good |
| Example 27 | Example 13 | 55 | 10 | Good |
| Example 28 | Example 14 | 55 | 10 | Good |
| Comparative Example 2 | — | 80 | 26 | Poor |

As is evident from Table 1, Examples 1 to 14 using any of the compounds or the resins of the present embodiment, BiP-1 to BiP-6 and RBiP-1 to RBiP-6, were confirmed to be good in terms of both solubility and etching resistance. On the other hand, Comparative Example 1 using CR-1 (phenol-modified dimethylnaphthaleneformaldehyde resin) resulted in poor etching resistance.

As is evident from Table 2, Examples 15 to 28 using any of the compounds or the resins of the present embodiment, BiP-1 to BiP-6 and RBiP-1 to RBiP-6, were confirmed to have a good resist pattern shape after development and have no major defects found. Furthermore, each of Examples 15 to 28 was confirmed to be significantly superior to Comparative Example 2, in which no underlayer film was formed, in both resolution and sensitivity.

Here, a good resist pattern shape after development indicates that the underlayer film forming materials for lithography used in Examples 15 to 28 have good adhesiveness to a resist material (photoresist material and the like).

Examples 29 to 42

A $SiO_2$ substrate with a film thickness of 300 nm was coated with the solution of the underlayer film forming material for lithography according to each of Examples 1 to 14, and baked at 240° C. for 60 seconds and further at 400° C. for 120 seconds to form each underlayer film with a film thickness of 80 nm. This underlayer film was coated with a silicon-containing intermediate layer material and baked at 200° C. for 60 seconds to form an intermediate layer film with a film thickness of 35 nm. This intermediate layer film was further coated with the above resist solution for ArF and baked at 130° C. for 60 seconds to form a photoresist layer with a film thickness of 150 nm. The silicon-containing intermediate layer material used was the silicon atom-containing polymer described in <Synthesis Example 1> of Japanese Patent Laid-Open No. 2007-226170. Subsequently, the photoresist layer was mask exposed using an electron beam lithography system (manufactured by ELIONIX INC.; ELS-7500, 50 keV), baked (PEB) at 115° C. for 90 seconds, and developed for 60 seconds in a 2.38 mass % tetramethylammonium hydroxide (TMAH) aqueous solution to obtain a 55 nm L/S (1:1) positive type resist pattern. Then, the silicon-containing intermediate layer film (SOG) was dry etched with the obtained resist pattern as a mask using RIE-10NR manufactured by Samco International, Inc. Subsequently, dry etching of the underlayer film with the obtained silicon-containing intermediate layer film pattern as a mask and dry etching of the $SiO_2$ film with the obtained underlayer film pattern as a mask were performed in order.

Respective etching conditions are as shown below.
Conditions for etching of resist intermediate layer film with resist pattern
  Output: 50 W
  Pressure: 20 Pa
  Time: 1 min
  Etching gas
  Ar gas flow rate:$CF_4$ gas flow rate:$O_2$ gas flow rate=50:8:2 (sccm)
Conditions for etching of resist underlayer film with resist intermediate film pattern
  Output: 50 W
  Pressure: 20 Pa
  Time: 2 min
  Etching gas
  Ar gas flow rate:$CF_4$ gas flow rate:$O_2$ gas flow rate=50:5:5 (sccm)
Conditions for etching of $SiO_2$ film with resist underlayer film pattern
  Output: 50 W
  Pressure: 20 Pa
  Time: 2 min
  Etching gas
  Ar gas flow rate:$CsF_{12}$ gas flow rate:$C_2F_6$ gas flow rate:$O_2$ gas flow rate
  =50:4:3:1 (sccm)

[Evaluation]

The pattern cross section (that is, the shape of the $SiO_2$ film after etching) obtained as described above was observed by using a product manufactured by Hitachi, Ltd., "electron microscope (S-4800)". The observation results are shown in Table 3. In the table, "good" means that no major defects were found in the formed pattern cross section, and "poor" means that major defects were found in the formed pattern cross section.

TABLE 3

| | Underlayer film forming material | Shape of SiO2 film | Appearance |
|---|---|---|---|
| Example 29 | Example 1 | Rectangle | Good |
| Example 30 | Example 2 | Rectangle | Good |
| Example 31 | Example 3 | Rectangle | Good |
| Example 32 | Example 4 | Rectangle | Good |
| Example 33 | Example 5 | Rectangle | Good |
| Example 34 | Example 6 | Rectangle | Good |
| Example 35 | Example 7 | Rectangle | Good |
| Example 36 | Example 8 | Rectangle | Good |
| Example 37 | Example 9 | Rectangle | Good |
| Example 38 | Example 10 | Rectangle | Good |
| Example 39 | Example 11 | Rectangle | Good |

TABLE 3-continued

| | Underlayer film forming material | Shape of SiO2 film | Appearance |
|---|---|---|---|
| Example 40 | Example 12 | Rectangle | Good |
| Example 41 | Example 13 | Rectangle | Good |
| Example 42 | Example 14 | Rectangle | Good |

Examples 43 to 48

A SiO$_2$ substrate with a film thickness of 300 nm was coated with the solution of the optical component forming composition having the same composition as that of the solution of the underlayer film forming material for lithography prepared in each of the above Examples 1 to 6, and baked at 260° C. for 300 seconds to form each optical component forming film with a film thickness of 100 nm. Then, tests for the refractive index and the transparency at a wavelength of 633 nm were carried out by using a vacuum ultraviolet with variable angle spectroscopic ellipsometer (VUV-VASE) manufactured by J.A. Woollam Japan, and the refractive index and the transparency were evaluated according to the following criteria. The evaluation results are shown in Table 4.

[Evaluation Criteria for Refractive Index]
A: The refractive index is 1.60 or more.
C: The refractive index is less than 1.60.

[Evaluation Criteria for Transparency]
A: The absorption coefficient is less than 0.03.
C: The absorption coefficient is 0.03 or more.

TABLE 4

| | Underlayer film forming material | Refractive index | Transparency |
|---|---|---|---|
| Example 43 | Example 1 | A | A |
| Example 44 | Example 2 | A | A |
| Example 45 | Example 3 | A | A |
| Example 46 | Example 4 | A | A |
| Example 47 | Example 5 | A | A |
| Example 48 | Example 6 | A | A |

Examples 49 to 52 and Comparative Example 3

(Heat Resistance and Resist Performance)

By using the compounds or the resins obtained in Synthesis Working Example 1 to Synthesis Working Example 4, a test for heat resistance and evaluation of resist performance were carried out, and the results thereof are shown in Table 5.

(Preparation of Resist Composition)

By using each of the compounds or resins synthesized as described above, a resist composition was prepared according to the recipe shown in Table 5. For the components of the resist compositions in Table 5, the following acid generating agent (C), acid diffusion controlling agent (E), and solvent were used.

Acid Generating Agent (C)
P-1: triphenylbenzenesulfonium trifluoromethanesulfonate (Midori Kagaku Co., Ltd.) Acid diffusion controlling agent (E)
Q-1: trioctylamine (Tokyo Kasei Kogyo Co., Ltd.) Solvent
S-1: propylene glycol monomethyl ether (Tokyo Kasei Kogyo Co., Ltd.)

(Method for Evaluating Resist Performance of Resist Composition)

A clean silicon wafer was spin coated with the homogeneous resist composition, and then prebaked (PB) before exposure in an oven of 110° C. to form a resist film with a thickness of 60 nm. The obtained resist film was irradiated with electron beams of 1:1 line and space setting with a 50 nm interval using an electron beam lithography system (ELS-7500 manufactured by ELIONIX INC.). After irradiation, the resist film was heated at each predetermined temperature for 90 seconds, and immersed in a 2.38 mass % TMAH alkaline developing solution for 60 seconds for development. Subsequently, the resist film was washed with ultrapure water for 30 seconds, and dried to form a positive type resist pattern. Concerning the formed resist pattern, the line and space were observed by a scanning electron microscope (S-4800 manufactured by Hitachi High-Technologies Corporation) to evaluate the reactivity by electron beam irradiation of the resist composition.

In the table, "good" means that the resist pattern shape forms a rectangle and no defects are found, and "poor" means that the pattern does not form a rectangle or defects are found.

TABLE 5

| | Compound/ resin | Evaluation of heat resistance | Resist composition | | | | Evaluation of resist performance |
|---|---|---|---|---|---|---|---|
| | | | Resin [g] | P-1 [g] | Q-1 [g] | S-1 [g] | |
| Example 49 | BiP-1 | A | 1.0 | 0.3 | 0.03 | 50.0 | Good |
| Example 50 | BiP-2 | A | 1.0 | 0.3 | 0.03 | 50.0 | Good |
| Example 51 | RBiP-1 | A | 1.0 | 0.3 | 0.03 | 50.0 | Good |
| Example 52 | RBiP-2 | A | 1.0 | 0.3 | 0.03 | 50.0 | Good |
| Comparative Example 3 | CR-1 | C | 1.0 | 0.3 | 0.03 | 50.0 | Poor |

As is evident from Table 5, it was confirmed that each of the compounds or resins used in Example 49 to Example 52 has good heat resistance whereas the compound used in Comparative Example 3 is inferior in heat resistance.

Also, in the resist pattern evaluation, a good resist pattern was obtained by irradiation with electron beams of 1:1 line and space setting with a 50 nm interval in each of Examples 49 to Example 52. On the other hand, it was not possible to obtain a good resist pattern in Comparative Example 3.

Thus, the resins that satisfy the requirements of the present invention have high heat resistance and can impart a good shape to a resist pattern, as compared with the comparative compound (CR-1). As long as the above requirements of the present invention are met, compounds other than the resins described in Examples also exhibit the same effects.

Examples 53 to 56 and Comparative Example 4

(Preparation of Radiation-Sensitive Composition)

The components set forth in Table 6 were formulated and formed into homogeneous solutions, and the obtained homogeneous solutions were filtered through a Teflon® membrane filter with a pore diameter of 0.1 μm to prepare radiation-sensitive compositions. Each of the prepared radiation-sensitive compositions was evaluated as described below.

The following resist base material was used in Comparative Example 4.
PHS-1: polyhydroxystyrene Mw=8000 (Sigma-Aldrich)
The following optically active compound (B) was used.
B-1: naphthoquinonediazide-based sensitizing agent having the following chemical structural formula (G) (4NT-300, Toyo Gosei Co., Ltd.)

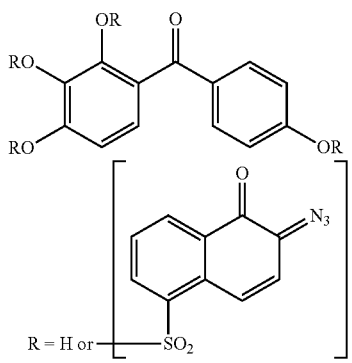

(G)

The following solvent was used.
S-1: propylene glycol monomethyl ether (Tokyo Kasei Kogyo Co., Ltd.)

TABLE 6

| | Composition | | |
|---|---|---|---|
| | Component (A) [g] | Optically active compound (B) [g] | Solvent [g] |
| Example 53 | BiP-1 0.5 | B-1 1.5 | S-1 30.0 |
| Example 54 | BiP-2 0.5 | B-1 1.5 | S-1 30.0 |
| Example 55 | RBiP-1 0.5 | B-1 1.5 | S-1 30.0 |
| Example 56 | RBiP-2 0.5 | B-1 1.5 | S-1 30.0 |
| Comparative Example 4 | PHS-1 0.5 | B-1 1.5 | S-1 30.0 |

(Evaluation of Resist Performance of Radiation-Sensitive Composition)

A clean silicon wafer was spin coated with the radiation-sensitive composition obtained as described above, and then prebaked (PB) before exposure in an oven of 110° C. to form a resist film with a thickness of 200 nm. The resist film was exposed to ultraviolet using an ultraviolet exposure apparatus (mask aligner MA-10 manufactured by Mikasa Co., Ltd.). The ultraviolet lamp used was a super high pressure mercury lamp (relative intensity ratio: g-ray:h-ray:i-ray:j-ray=100:80:90:60). After irradiation, the resist film was heated at 110° C. for 90 seconds, and immersed in a 2.38 mass % TMAH alkaline developing solution for 60 seconds for development. Subsequently, the resist film was washed with ultrapure water for 30 seconds, and dried to form a 5 μm positive type resist pattern.

The obtained line and space were observed in the formed resist pattern by a scanning electron microscope (S-4800 manufactured by Hitachi High-Technologies Corporation). As for the line edge roughness, a pattern having asperities of less than 50 nm was evaluated to be good.

In the case of using the radiation-sensitive composition according to each of Examples 53 to 56, a good resist pattern with a resolution of 5 μm was able to be obtained. The roughness of the pattern was also small and good.

On the other hand, in the case of using the radiation-sensitive composition according to Comparative Example 4, a good resist pattern with a resolution of 5 μm was able to be obtained. However, the roughness of the pattern was large and poor.

As described above, it was found that each of the radiation-sensitive compositions according to Example 53 to Example 56 can form a resist pattern that has small roughness and a good shape, as compared with the radiation-sensitive composition according to Comparative Example 4. As long as the above requirements of the present invention are met, radiation-sensitive compositions other than those described in Examples also exhibit the same effects.

Each of the compounds or resins obtained in Synthesis Working Example 1 to Synthesis Working Example 4 has a relatively low molecular weight and a low viscosity. As such, the embedding properties and film surface flatness of underlayer film forming materials for lithography containing these compounds or resins can be relatively advantageously enhanced. Furthermore, each of these compounds or resins has a thermal decomposition temperature of 150° C. or higher (evaluation A) and has high heat resistance. Therefore, they can be used even under high temperature baking conditions.

(Example 57) Purification of BiP-1 with Acid

In a four necked flask (capacity: 1000 mL, with a detachable bottom), 150 g of a solution (10% by mass) formed by dissolving BiP-1 obtained in Synthesis Working Example 1 in PGMEA was charged, and was heated to 80° C. with stirring. Then, 37.5 g of an aqueous oxalic acid solution (pH 1.3) was added thereto, and the resultant mixture was stirred for 5 minutes and then left to stand for 30 minutes. This separated the mixture into an oil phase and an aqueous phase, and the aqueous phase was thus removed. After repeating this operation once, 37.5 g of ultrapure water was charged to the obtained oil phase, and after stirring for 5 minutes, the mixture was left to stand for 30 minutes and the aqueous phase was removed. After repeating this operation three times, the residual water and PGMEA were concentrated and removed by heating to 80° C. and reducing the pressure in the flask to 200 hPa or less. By diluting with PGMEA of EL grade (a reagent manufactured by Kanto Chemical Co., Inc.) such that the concentration of BiP-1 in PGMEA solution was adjusted to 10% by mass, a PGMEA solution of BiP-1 with a reduced metal content was obtained.

(Comparative Example 5) Purification of BiP-1 with Ultrapure Water

In the same manner as of Example 57 except that ultrapure water was used instead of the aqueous oxalic acid solution, and by adjusting the concentration to 10% by mass, a PGMEA solution of BiP-1 was obtained.

For the 10 mass % BiP-1 solution in PGMEA before the treatment, and the solutions obtained in Example 57 and Comparative Example 5, the contents of various metals were measured by ICP-MS. The measurement results are shown in Table 7.

TABLE 7

| | Metal content (ppb) | | | | | |
|---|---|---|---|---|---|---|
| | Na | Mg | K | Fe | Cu | Zn |
| BiP-1 before treatment | >99 | 25.3 | >99 | >99 | 13.5 | 10.6 |
| Example 57 | 2.3 | 1.1 | 0.6 | 2.1 | 0.3 | 0.4 |
| Comparative Example 5 | 2.5 | 1.5 | 1.0 | >99 | 2.5 | 3.0 |

The compound and the resin of the present invention has high heat resistance, has high solvent solubility, and is applicable to a wet process. Therefore, a film forming material for lithography using the compound or the resin of the present invention, and a film for lithography thereof can be utilized widely and effectively in various applications that require such performances. Accordingly, the present invention can be utilized widely and effectively in, for example, electrical insulating materials, resins for resists, encapsulation resins for semiconductors, adhesives for printed circuit boards, electrical laminates mounted in electric equipment, electronic equipment, industrial equipment, and the like, matrix resins of prepregs mounted in electric equipment, electronic equipment, industrial equipment, and the like, buildup laminate materials, resins for fiber-reinforced plastics, resins for encapsulation of liquid crystal display panels, coating materials, various coating agents, adhesives, coating agents for semiconductors, resins for resists for semiconductors, resins for underlayer film formation, and the like. In particular, the present invention can be utilized particularly effectively in the field of films for lithography.

The invention claimed is:

1. A compound represented by the following formula (1-1):

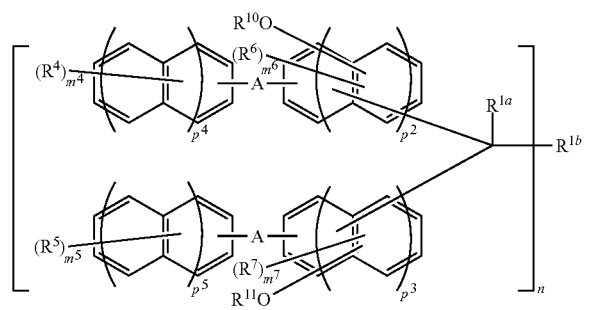

(1-1)

wherein A is sulfur, oxygen, or a sulfonyl group; $R^{1a}$ is a hydrogen atom or a monovalent group having 1 to 10 carbon atoms; $R^{1b}$ is an n-valent aromatic group having 6 to 30 carbon atoms and does not include a heteroatom; $R^4$ to $R^5$ are each independently a linear, branched or cyclic alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 1 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond and at least one $R^4$ and/or at least one $R^5$ is a hydroxy group and/or a thiol group; $R^6$ to $R^7$ are each independently an alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 2 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond; $R^{10}$ to $R^{11}$ are each a hydrogen atom; $m^4$ and $m^5$ are each independently an integer of 0 to 9; $m^6$ and $m^7$ are each independently an integer of 0 to 7; n is an integer of 1 to 4; and $p^2$ to $p^5$ are each independently an integer of 0 to 2.

2. The compound according to claim 1, wherein the compound represented by the above formula (1-1) is a compound represented by the following formula (1b):

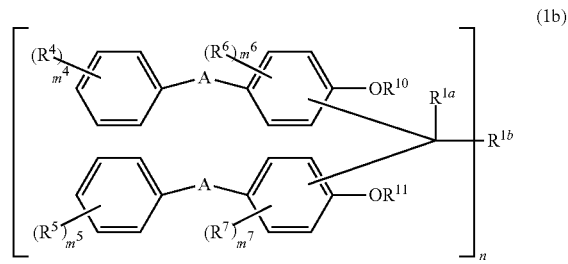

(1b)

wherein A, $R^4$, $R^5$, $R^6$, $R^7$, $R^{10}$, $R^{11}$, $R^{1a}$, $R^{1b}$, $m^4$ and $m^5$, and n are as defined in A, $R^4$, $R^5$, $R^6$, $R^7$, $R^{10}$, $R^{11}$, $R^{1a}$, $R^{1b}$, and n in the above formula (1-1), respectively; $m^4$ and $m^5$ are each independently an integer of 0 to 5; and $m^6$ and $m^7$ are each independently an integer of 0 to 4.

3. A compound represented by the following formula (1c):

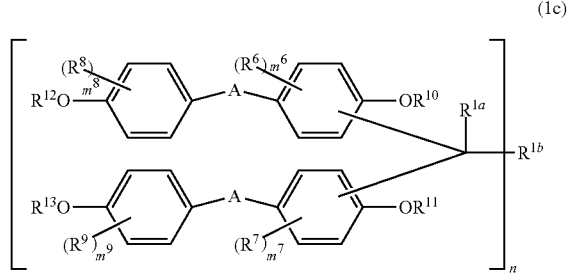

(1c)

wherein A is sulfur, oxygen, or a sulfonyl group; $R^{1a}$ is a hydrogen atom or a monovalent group having 1 to 10 carbon atoms; $R^{1b}$ is an n-valent aromatic group having 1 to 30 carbon atoms; $R^6$ and $R^7$ are each independently an alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 2 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond; $R^{10}$ and $R^{11}$ are each a hydrogen atom; $m^6$ and $m^7$ are each independently an integer of 0 to 4; $R^8$ and $R^9$ are each independently an alkyl group having 1 to 30 carbon atoms and optionally having a substituent, an aryl group having 6 to 30 carbon atoms and optionally having a substituent, an alkenyl group having 2 to 30 carbon atoms and optionally having a substituent, an alkynyl group having 2 to 30 carbon atoms and optionally having a substituent, an alkoxy group having 1 to 30 carbon atoms and optionally having a substituent, a halogen atom, a nitro group, an amino group, a carboxylic acid group, a crosslinkable group, a dissociation group, a thiol group or a hydroxy group, wherein the alkyl group, the aryl group, the alkenyl group and the alkoxy group each optionally contain an ether bond, a ketone bond or an ester bond; $R^{12}$ and $R^{13}$ are each independently a hydrogen atom; and $m^8$ and $m^9$ are each independently an integer of 0 to 4.

4. A resin obtained using the compound according to claim 1 as a monomer.

5. A composition comprising one or more selected from the group consisting of the compound according to claim 1 and a resin obtained using the compound as a monomer.

6. The composition according to claim 5, further comprising a solvent.

7. The composition according to claim 5, further comprising an acid generating agent.

8. The composition according to claim 5, further comprising a crosslinking agent.

9. The composition according to claim 5, wherein the composition is used in film formation for lithography.

10. The composition according to claim 9 used in film formation for lithography, wherein the composition is used in formation of a photoresist layer.

11. The composition according to claim 9 used in film formation for lithography, wherein the composition is used in formation of a resist underlayer film.

12. The composition according to claim 5, wherein the composition is used in optical component formation.

13. A method for forming a resist pattern, comprising the steps of:
forming a resist film on a substrate using the composition according to claim 10;
exposing at least a portion of the formed resist film; and
developing the exposed resist film, thereby forming a resist pattern.

14. A radiation-sensitive composition comprising a component (A), which is one or more kinds of the compound according to claim 1, an optically active diazonaphthoquinone compound (B), and a solvent,
wherein a content of the solvent is 20 to 99% by mass based on 100% by mass in total of the radiation-sensitive composition, and a content of components except for the solvent is 1 to 80% by mass based on 100% by mass in total of the radiation-sensitive composition.

15. The radiation-sensitive composition according to claim 14, wherein a content ratio among the component (A), the optically active diazonaphthoquinone compound (B) and a further optional component (D) optionally contained in the radiation-sensitive composition ((A)/(B)/(D)) is 1 to 99% by mass/99 to 1% by mass/0 to 98% by mass based on 100% by mass of a solid content of the radiation-sensitive composition.

16. A method for forming a resist pattern, comprising the steps of: forming a resist film on a substrate using the radiation-sensitive composition according to claim 14; exposing at least a portion of the formed resist film; and developing the exposed resist film, thereby forming a resist pattern.

17. The method for forming a resist pattern according to claim 16, wherein the method is a method for forming a resist permanent film.

18. A method for forming a resist pattern, comprising:
an underlayer film formation step of forming an underlayer film on a substrate using the composition according to claim 11;
a photoresist layer formation step of forming at least one photoresist layer on the underlayer film formed through the underlayer film formation step; and
a step of irradiating a predetermined region of the photoresist layer formed through the photoresist layer formation step with radiation for development.

19. A method for forming a circuit pattern, comprising:
an underlayer film formation step of forming an underlayer film on a substrate using the composition according to claim 11;
an intermediate layer film formation step of forming an intermediate layer film on the underlayer film formed through the underlayer film formation step;
a photoresist layer formation step of forming at least one photoresist layer on the intermediate layer film formed through the intermediate layer film formation step;
a resist pattern formation step of irradiating a predetermined region of the photoresist layer formed through the photoresist layer formation step with radiation for development, thereby forming a resist pattern;
an intermediate layer film pattern formation step of etching the intermediate layer film with the resist pattern formed through the resist pattern formation step as a mask, thereby forming an intermediate layer film pattern;
an underlayer film pattern formation step of etching the underlayer film with the intermediate layer film pattern formed through the intermediate layer film pattern formation step as a mask, thereby forming an underlayer film pattern; and
a substrate pattern formation step of etching the substrate with the underlayer film pattern formed through the underlayer film pattern formation step as a mask, thereby forming a pattern on the substrate.

20. A method for purifying the compound according to claim 1 or a resin obtained using the compound as a monomer, comprising:
an extraction step of bringing a solution containing the compound or the resin and an organic solvent that does not inadvertently mix with water into contact with an acidic aqueous solution, thereby carrying out extraction.

* * * * *